US007070957B2

(12) United States Patent
Olson et al.

(10) Patent No.: US 7,070,957 B2
(45) Date of Patent: Jul. 4, 2006

(54) STARS—A MUSCLE-SPECIFIC ACTIN-BINDING PROTEIN

(75) Inventors: Eric Olson, Dallas, TX (US); Akiko Arai, Mie (JP)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 10/644,659

(22) Filed: Aug. 20, 2003

(65) Prior Publication Data

US 2004/0086920 A1  May 6, 2004

Related U.S. Application Data

(60) Provisional application No. 60/404,706, filed on Aug. 20, 2002.

(51) Int. Cl.
  *C12P 21/06* (2006.01)
(52) U.S. Cl. ..................... 435/69.1; 536/23.1; 530/350
(58) Field of Classification Search ............... 536/23.1; 530/350; 514/12; 435/6, 7.1, 69.1
See application file for complete search history.

(56) References Cited

U.S. PATENT DOCUMENTS

2003/0236392 A1* 12/2003 Isogai et al. ............... 536/23.1

OTHER PUBLICATIONS

Akiko et al., STARS, a steated Muscle Activator of Rho Signaling and Serum Response Factor-dependent Transcription, Jul. 4, 2002, Journal of Bio. Chem. vol. 227, No. 27, pp. 24453-24459.*
Aikko et al. NCBI Submission Accesion No. AF503617.*
Isogai et al., (NCBI Submission Accession No. AK092694).*
Belaguli et al., "Cardiac tissue enriched factors serum reponse factor and GATA-4 are mutual coregulators," *Molecular and Cellular Biology*, 20(20):7550-7558, 2000.
Chen and Schwartz, "Recruitment of the tinman homolog Nkx-2.5 by serum response factor activates cardiac α-actin gene transcription," *Molecular and Cellular Biology*, 16(11):6372-6384, 1996.
Cooper and Schafer, "Control of actin assembly and disassembly at filament ends," *Curr. Opin. Cell. Biol.*, 12:97-103, 2000.
Kaibuchi et al., "Regulation of the cytoskeleton and cell adhesion by the Rho family GTPases in mammalian cells," *Annu. Rev. Biochem*, 68:459-486, 1999.

Mack et al., Smooth muscle differentiation marker gene expression is regulated by RhoA-mediated actin polymerization, *J. Biol. Chem.*, 276(1):341-347, 2001.
Maekawa et al., "Signaling from Rho to the actin cytoskeleton through protein kinases ROCK and LIM-kinase," *Sciences*, 285:895-898, 1999.
Morin et al., "Serum response factor-GATA ternary complex required for nuclear signaling by a G-proetin-coupled receptor," *Molecular and Cellular Biology*, 21(4):1036-1044, 2001.
Morton et al., Lantrunculin alters the actin-monomer subunit interface to prevent polymerization, *Nat. Cell. Biol.*, 2:376-378, 2000.
Narumiya et al., "Rho effectors and reorganization of actine cytoskeleton," *FEBS Letters*, 410:68-72, 1997.
Sotiropoulos et al., "Signal-regulated activation of serum response factor is mediated by changes in actin dynamics," *Cell*, 98:159-169, 1999.
Van Aelst and D'Souza-Schorey, "Rho GTPases and signaling networks," *Genes Dev.*, 11:2295-2322, 1997.
Wang et al., "Activation of cardiac gene expression by myocardin, a transcriptional cofactor for serum response factor," *Cell*, 105:851-862, 2001.
Wei et al., RhoA signaling via serum responses factor plays an obligatory role in myogenic differentiation, *J. Biol. Chem.*, 273(46):30287-30294, 1998.
Wei et al., "Betal integrin and organized actin filaments facilitate cardiomyocyte-specific RhoA-dependent activation of the skeletal alpha-actin promoter," *FASEB J.*, 785-796, 2001.
Yamamoto et al., "Phosphatidylinositol 4,5-biophosphated induces actin stress-fiber formation an dinhibits membrane ruffling in CV1 cells," *J. Cell. Biol.*, 152(5):867-876, 2001.

\* cited by examiner

*Primary Examiner*—Jon Weber
*Assistant Examiner*—Robert B. Mondesi
(74) *Attorney, Agent, or Firm*—Fulbright & Jaworski, LLP

(57) ABSTRACT

The present invention relates to a new polypeptide and the gene coding therefore, gene being an evolutionarily conserved actin-binding protein, called STARS (striated muscle activator of Rho signalin), that is expressed specifically in cardiac and skeletal muscle cells and is upregulated in response to calcineurin signaling during cardiac hypertrophy. STARS is localized to the thin filament of the sarcomere and to actin stress fibers where it promotes actin bundling. STARS stimulates the transcriptional activity of serum response factor (SRF) through a mechanism that requires actin bundling and Rho kinase activation. STARS provides a mechanism for selectively enhancing the transcriptional activity of SRF in muscle cells and for linking changes in actin dynamics to gene transcription. Also disclosed are methods of using the gene and protein in drug screening and therapy, including, for example, use of the gene in gene therapy to treat cardiovascular disease.

25 Claims, 7 Drawing Sheets

Figure 1

SEQUENCE LISTING

```
<160> NUMBER OF SEQ ID NOS: 15

<210> SEQ ID NO 1
<211> LENGTH: 1146
<212> TYPE: DNA
<213> ORGANISM: Homo sapiens
<220> FEATURE:
<221> NAME/KEY: CDS
<222> LOCATION: (1)..(1146)

<400> SEQUENCE: 1 atg gct ccg ggc gaa aag gaa agc ggg gag ggc cca gcc aag agc gcc        48
Met Ala Pro Gly Glu Lys Glu Ser Gly Glu Gly Pro Ala Lys Ser Ala
1               5                   10                  15 ctc cgg aag ata cgc aca gcc acc ctg gtc atc agc ttg gcc cga ggt        96
Leu Arg Lys Ile Arg Thr Ala Thr Leu Val Ile Ser Leu Ala Arg Gly
                20                  25                  30 tgg cag cag tgg gcg aat gag aac agc atc agg cag gcc cag gag cct       144
Trp Gln Gln Trp Ala Asn Glu Asn Ser Ile Arg Gln Ala Gln Glu Pro
            35                  40                  45 aca ggc tgg ctg ccg gga ggg acc cag gac tca cct caa gct cct aaa       192
Thr Gly Trp Leu Pro Gly Gly Thr Gln Asp Ser Pro Gln Ala Pro Lys
        50                  55                  60 cca atc aca ccc cct act tca cac cag aaa gct cag agt gcc cca aag       240
Pro Ile Thr Pro Pro Thr Ser His Gln Lys Ala Gln Ser Ala Pro Lys
65                  70                  75                  80 tcg cca ccc cgc ctg cca gaa gga cat gga gat gga caa agc tca gag       288
Ser Pro Pro Arg Leu Pro Glu Gly His Gly Asp Gly Gln Ser Ser Glu
                85                  90                  95 aaa gcc cct gag gtt tct cac atc aaa aag aaa gag gtg tcc aaa acg       336
Lys Ala Pro Glu Val Ser His Ile Lys Lys Lys Glu Val Ser Lys Thr
                100                 105                 110 gtg gtc agc aag act tac gag aga gga ggg gac gtg agc cac ctc agc       384
Val Val Ser Lys Thr Tyr Glu Arg Gly Gly Asp Val Ser His Leu Ser
```

| | | | | | | | | | | | | | | | |
|---|---|---|---|---|---|---|---|---|---|---|---|---|---|---|---|
| | | 115 | | | | 120 | | | | | 125 | | | | |
| cac | agg | tac | gag | agg | gat | gct | ggt | gtg | ctt | gaa | cct | ggg | cag | cca | gag | 432 |
| His | Arg | Tyr | Glu | Arg | Asp | Ala | Gly | Val | Leu | Glu | Pro | Gly | Gln | Pro | Glu | |
| | 130 | | | | | 135 | | | | | 140 | | | | |
| aat | gac | att | gac | aga | atc | ctc | cac | agc | cac | ggc | tcc | cca | acg | cgg | agg | 480 |
| Asn | Asp | Ile | Asp | Arg | Ile | Leu | His | Ser | His | Gly | Ser | Pro | Thr | Arg | Arg | |
| 145 | | | | | 150 | | | | | 155 | | | | | 160 | |
| aga | aaa | tgt | gcc | aac | ctg | gtg | tct | gag | cta | acc | aag | ggc | tgg | aga | gtg | 528 |
| Arg | Lys | Cys | Ala | Asn | Leu | Val | Ser | Glu | Leu | Thr | Lys | Gly | Trp | Arg | Val | |
| | | | | 165 | | | | | 170 | | | | | 175 | | |
| atg | gag | cag | gag | gag | ccc | aca | tgg | agg | agt | gac | agc | gta | gac | aca | gag | 576 |
| Met | Glu | Gln | Glu | Glu | Pro | Thr | Trp | Arg | Ser | Asp | Ser | Val | Asp | Thr | Glu | |
| | | | | 180 | | | | | 185 | | | | | 190 | | |
| gac | agc | ggc | tat | gga | gga | gag | gct | gag | gag | agg | ccc | gag | cag | gat | gga | 624 |
| Asp | Ser | Gly | Tyr | Gly | Gly | Glu | Ala | Glu | Glu | Arg | Pro | Glu | Gln | Asp | Gly | |
| | | | 195 | | | | | 200 | | | | | 205 | | | |
| gtg | cag | gtg | gct | gtg | gtc | agg | atc | aag | cgc | ccc | ttg | ccc | tcc | cag | gta | 672 |
| Val | Gln | Val | Ala | Val | Val | Arg | Ile | Lys | Arg | Pro | Leu | Pro | Ser | Gln | Val | |
| | 210 | | | | | 215 | | | | | 220 | | | | | |
| aac | aga | ttt | aca | gag | aaa | ctc | aac | tgc | aaa | gcc | caa | cag | aaa | tat | agc | 720 |
| Asn | Arg | Phe | Thr | Glu | Lys | Leu | Asn | Cys | Lys | Ala | Gln | Gln | Lys | Tyr | Ser | |
| 225 | | | | | 230 | | | | | 235 | | | | | 240 | |
| cca | gtg | ggc | aac | ttg | aaa | ggg | aga | tgg | cag | cag | tgg | gct | gat | gaa | cac | 768 |
| Pro | Val | Gly | Asn | Leu | Lys | Gly | Arg | Trp | Gln | Gln | Trp | Ala | Asp | Glu | His | |
| | | | | 245 | | | | | 250 | | | | | 255 | | |
| ata | caa | tcc | cag | aag | ctc | aat | cct | ttc | agt | gaa | gag | ttt | gat | tac | gag | 816 |
| Ile | Gln | Ser | Gln | Lys | Leu | Asn | Pro | Phe | Ser | Glu | Glu | Phe | Asp | Tyr | Glu | |
| | | | 260 | | | | | 265 | | | | | 270 | | | |
| ctg | gcc | atg | tcc | acc | cgc | cta | cac | aaa | gga | gat | gag | ggc | tat | ggc | cgc | 864 |
| Leu | Ala | Met | Ser | Thr | Arg | Leu | His | Lys | Gly | Asp | Glu | Gly | Tyr | Gly | Arg | |
| | 275 | | | | | 280 | | | | | 285 | | | | | |
| ccc | aaa | gaa | gga | acc | aaa | act | gct | gaa | agg | gcc | aag | cgt | gct | gag | gag | 912 |
| Pro | Lys | Glu | Gly | Thr | Lys | Thr | Ala | Glu | Arg | Ala | Lys | Arg | Ala | Glu | Glu | |
| 290 | | | | | 295 | | | | | 300 | | | | | | |
| cac | atc | tac | agg | gaa | atg | atg | gac | atg | tgc | ttc | att | atc | tgc | aca | atg | 960 |
| His | Ile | Tyr | Arg | Glu | Met | Met | Asp | Met | Cys | Phe | Ile | Ile | Cys | Thr | Met | |
| 305 | | | | | 310 | | | | | 315 | | | | | 320 | |
| gct | cgc | cac | aga | cga | gat | ggc | aag | atc | cag | gtt | act | ttt | gga | gat | ctc | 1008 |
| Ala | Arg | His | Arg | Arg | Asp | Gly | Lys | Ile | Gln | Val | Thr | Phe | Gly | Asp | Leu | |
| | | | | 325 | | | | | 330 | | | | | 335 | | |
| ttt | gac | aga | tac | gtt | cgt | att | tca | gat | aaa | gta | gtg | ggc | att | ctc | atg | 1056 |
| Phe | Asp | Arg | Tyr | Val | Arg | Ile | Ser | Asp | Lys | Val | Val | Gly | Ile | Leu | Met | |
| | | | 340 | | | | | 345 | | | | | 350 | | | |
| cgt | gcc | agg | aaa | cat | gga | ctg | gta | gac | ttt | gaa | gga | gag | atg | cta | tgg | 1104 |
| Arg | Ala | Arg | Lys | His | Gly | Leu | Val | Asp | Phe | Glu | Gly | Glu | Met | Leu | Trp | |
| | 355 | | | | | 360 | | | | | 365 | | | | | |
| caa | ggc | cga | gat | gac | cat | gtt | gtg | att | acg | cta | ctc | aag | tga | | | 1146 |
| Gln | Gly | Arg | Asp | Asp | His | Val | Val | Ile | Thr | Leu | Leu | Lys | | | | |
| 370 | | | | | 375 | | | | | 380 | | | | | | |

<210> SEQ ID NO 2
<211> LENGTH: 381
<212> TYPE: PRT
<213> ORGANISM: Homo sapiens

<400> SEQUENCE: 2

Met Ala Pro Gly Glu Lys Glu Ser Gly Glu Gly Pro Ala Lys Ser Ala
1               5                   10                  15

Leu Arg Lys Ile Arg Thr Ala Thr Leu Val Ile Ser Leu Ala Arg Gly
            20                  25                  30

| | | | | | | | | | | | |
|---|---|---|---|---|---|---|---|---|---|---|---|
|Trp|Gln|Gln|Trp|Ala|Asn|Glu|Asn|Ser|Ile|Arg|Gln|Ala|Gln|Glu|Pro|
| |35| | | |40| | | |45| | |

Trp Gln Gln Trp Ala Asn Glu Asn Ser Ile Arg Gln Ala Gln Glu Pro
            35                  40                  45

Thr Gly Trp Leu Pro Gly Gly Thr Gln Asp Ser Pro Gln Ala Pro Lys
 50                  55                  60

Pro Ile Thr Pro Pro Thr Ser His Gln Lys Ala Gln Ser Ala Pro Lys
65                  70                  75                  80

Ser Pro Pro Arg Leu Pro Glu Gly His Gly Asp Gly Gln Ser Ser Glu
                85                  90                  95

Lys Ala Pro Glu Val Ser His Ile Lys Lys Glu Val Ser Lys Thr
            100                 105                 110

Val Val Ser Lys Thr Tyr Glu Arg Gly Gly Asp Val Ser His Leu Ser
            115                 120                 125

His Arg Tyr Glu Arg Asp Ala Gly Val Leu Glu Pro Gly Gln Pro Glu
            130                 135                 140

Asn Asp Ile Asp Arg Ile Leu His Ser His Gly Ser Pro Thr Arg Arg
145                 150                 155                 160

Arg Lys Cys Ala Asn Leu Val Ser Glu Leu Thr Lys Gly Trp Arg Val
                165                 170                 175

Met Glu Gln Glu Glu Pro Thr Trp Arg Ser Asp Ser Val Asp Thr Glu
            180                 185                 190

Asp Ser Gly Tyr Gly Gly Glu Ala Glu Glu Arg Pro Glu Gln Asp Gly
            195                 200                 205

Val Gln Val Ala Val Val Arg Ile Lys Arg Pro Leu Pro Ser Gln Val
            210                 215                 220

Asn Arg Phe Thr Glu Lys Leu Asn Cys Lys Ala Gln Gln Lys Tyr Ser
225                 230                 235                 240

Pro Val Gly Asn Leu Lys Gly Arg Trp Gln Gln Trp Ala Asp Glu His
                245                 250                 255

Ile Gln Ser Gln Lys Leu Asn Pro Phe Ser Glu Glu Phe Asp Tyr Glu
            260                 265                 270

Leu Ala Met Ser Thr Arg Leu His Lys Gly Asp Glu Gly Tyr Gly Arg
            275                 280                 285

Pro Lys Glu Gly Thr Lys Thr Ala Glu Arg Ala Lys Arg Ala Glu Glu
            290                 295                 300

His Ile Tyr Arg Glu Met Met Asp Met Cys Phe Ile Cys Thr Met
305                 310                 315                 320

Ala Arg His Arg Arg Asp Gly Lys Ile Gln Val Thr Phe Gly Asp Leu
                325                 330                 335

Phe Asp Arg Tyr Val Arg Ile Ser Asp Lys Val Val Gly Ile Leu Met
            340                 345                 350

Arg Ala Arg Lys His Gly Leu Val Asp Phe Glu Gly Glu Met Leu Trp
            355                 360                 365

Gln Gly Arg Asp Asp His Val Val Ile Thr Leu Leu Lys
            370                 375                 380

<210> SEQ ID NO 3
<211> LENGTH: 1128
<212> TYPE: DNA
<213> ORGANISM: Mus musculus
<220> FEATURE:
<221> NAME/KEY: CDS
<222> LOCATION: (1)..(1128)

<400> SEQUENCE: 3 atg gct cca gga gaa agg gaa agg gag gcg ggg ccg gcc aag agt gcc        48

```
Met Ala Pro Gly Glu Arg Glu Arg Ala Gly Pro Ala Lys Ser Ala
1               5                   10                  15 ctc cgg aag gtc cgc aca gca acc ctg gtt atc aat ttg gcc cga ggt            96
Leu Arg Lys Val Arg Thr Ala Thr Leu Val Ile Asn Leu Ala Arg Gly
                20                  25                  30 tgg cag cag tgg gcg aat gag aac agt acc aaa cag gcc cag gag cct           144
Trp Gln Gln Trp Ala Asn Glu Asn Ser Thr Lys Gln Ala Gln Glu Pro
        35                  40                  45 gca ggc tgg ctg ccg gga gca act cat gac gta cct aac gct cct aaa           192
Ala Gly Trp Leu Pro Gly Ala Thr His Asp Val Pro Asn Ala Pro Lys
50                  55                  60 gaa gcc ggt cct tac cag cat gcc ccc aaa act ctg tct cca aag cca           240
Glu Ala Gly Pro Tyr Gln His Ala Pro Lys Thr Leu Ser Pro Lys Pro
65                  70                  75                  80 gat cga gac gga gag gga caa cac tca gaa gaa gcc acc gag gtc tcc           288
Asp Arg Asp Gly Glu Gly Gln His Ser Glu Glu Ala Thr Glu Val Ser
                85                  90                  95 cac att aaa agg aaa gag gtg acc aga acg gtt gtc agc aag gct tat           336
His Ile Lys Arg Lys Glu Val Thr Arg Thr Val Val Ser Lys Ala Tyr
                100                 105                 110 gag agg gga gga gat gtg aac tac ctg agc cac agg tat gag aat gat           384
Glu Arg Gly Gly Asp Val Asn Tyr Leu Ser His Arg Tyr Glu Asn Asp
            115                 120                 125 ggt ggc gtg tct gaa gct att cag cca gag aat gac att gac aga atc           432
Gly Gly Val Ser Glu Ala Ile Gln Pro Glu Asn Asp Ile Asp Arg Ile
        130                 135                 140 ctt ctt agt cac gac tcg cca aca cgg aga aga aaa tgc acc aac ctg           480
Leu Leu Ser His Asp Ser Pro Thr Arg Arg Arg Lys Cys Thr Asn Leu
145                 150                 155                 160 gtg tct gag ctg acc aaa ggc tgg aaa gtg atg gaa cag gaa gag ccc           528
Val Ser Glu Leu Thr Lys Gly Trp Lys Val Met Glu Gln Glu Glu Pro
                165                 170                 175 acg tgg aag agt gac agc gta gac aca gag gac agt ggc tac gga ggg           576
Thr Trp Lys Ser Asp Ser Val Asp Thr Glu Asp Ser Gly Tyr Gly Gly
                180                 185                 190 gat atg gag gag agg cct gag caa gat gca gcg cct gtg gct cct gcc           624
Asp Met Glu Glu Arg Pro Glu Gln Asp Ala Ala Pro Val Ala Pro Ala
            195                 200                 205 agg atc aaa cgc ccc ttg cac tcc cag gca aac agg tac tct gag cca           672
Arg Ile Lys Arg Pro Leu His Ser Gln Ala Asn Arg Tyr Ser Glu Pro
        210                 215                 220 ctc aac tgt aag gcc cat cgg aaa tac agc caa gtg gac aac ttg aaa           720
Leu Asn Cys Lys Ala His Arg Lys Tyr Ser Gln Val Asp Asn Leu Lys
225                 230                 235                 240 ggg agg tgg cag cag tgg gcc gat gaa cac gtc cag tcc cag aag ctc           768
Gly Arg Trp Gln Gln Trp Ala Asp Glu His Val Gln Ser Gln Lys Leu
                245                 250                 255 aat ccc ttc agt gac gaa ttt gac tat gac cta gcc atg tcc act cgg           816
Asn Pro Phe Ser Asp Glu Phe Asp Tyr Asp Leu Ala Met Ser Thr Arg
                260                 265                 270 ctc cac aag gga gac gag ggc tat ggc cgc ccc aaa gag gga agc aag           864
Leu His Lys Gly Asp Glu Gly Tyr Gly Arg Pro Lys Glu Gly Ser Lys
            275                 280                 285 aca gct gaa agg gcc aag cga gcg gaa gag cac atc tat cgg gaa att           912
Thr Ala Glu Arg Ala Lys Arg Ala Glu Glu His Ile Tyr Arg Glu Ile
        290                 295                 300 atg gaa ctg tgc ttt gtt atc cgc aca atg gct cgc cac aga cga gat           960
Met Glu Leu Cys Phe Val Ile Arg Thr Met Ala Arg His Arg Arg Asp
305                 310                 315                 320
```

```
ggc aag atc cag gtt act ttc gga gaa ctc ttt gat cgc tat gtt cgc    1008
Gly Lys Ile Gln Val Thr Phe Gly Glu Leu Phe Asp Arg Tyr Val Arg
            325                 330                 335 att tct gat aaa gtc gtg ggc atc ctc atg cgt gcc agg aaa cac gga    1056
Ile Ser Asp Lys Val Val Gly Ile Leu Met Arg Ala Arg Lys His Gly
        340                 345                 350 ctg gtg cac ttt gaa gga gag atg cta tgg caa ggc cga gac gac cat    1104
Leu Val His Phe Glu Gly Glu Met Leu Trp Gln Gly Arg Asp Asp His
    355                 360                 365 gtt gtg att act ctc gtt gag taa                                     1128
Val Val Ile Thr Leu Val Glu
370                 375

<210> SEQ ID NO 4
<211> LENGTH: 375
<212> TYPE: PRT
<213> ORGANISM: Mus musculus

<400> SEQUENCE: 4
```

Met Ala Pro Gly Glu Arg Glu Arg Glu Ala Gly Pro Ala Lys Ser Ala
1               5                   10                  15

Leu Arg Lys Val Arg Thr Ala Thr Leu Val Ile Asn Leu Ala Arg Gly
            20                  25                  30

Trp Gln Gln Trp Ala Asn Glu Asn Ser Thr Lys Gln Ala Gln Glu Pro
        35                  40                  45

Ala Gly Trp Leu Pro Gly Ala Thr His Asp Val Pro Asn Ala Pro Lys
    50                  55                  60

Glu Ala Gly Pro Tyr Gln His Ala Pro Lys Thr Leu Ser Pro Lys Pro
65                  70                  75                  80

Asp Arg Asp Gly Glu Gly Gln His Ser Glu Glu Ala Thr Glu Val Ser
                85                  90                  95

His Ile Lys Arg Lys Glu Val Thr Arg Thr Val Val Ser Lys Ala Tyr
            100                 105                 110

Glu Arg Gly Gly Asp Val Asn Tyr Leu Ser His Arg Tyr Glu Asn Asp
        115                 120                 125

Gly Gly Val Ser Glu Ala Ile Gln Pro Glu Asn Asp Ile Asp Arg Ile
    130                 135                 140

Leu Leu Ser His Asp Ser Pro Thr Arg Arg Lys Cys Thr Asn Leu
145                 150                 155                 160

Val Ser Glu Leu Thr Lys Gly Trp Lys Val Met Glu Gln Glu Pro
                165                 170                 175

Thr Trp Lys Ser Asp Ser Val Asp Thr Glu Asp Ser Gly Tyr Gly Gly
            180                 185                 190

Asp Met Glu Glu Arg Pro Glu Gln Asp Ala Ala Pro Val Ala Pro Ala
        195                 200                 205

Arg Ile Lys Arg Pro Leu His Ser Gln Ala Asn Arg Tyr Ser Glu Pro
    210                 215                 220

Leu Asn Cys Lys Ala His Arg Lys Tyr Ser Gln Val Asp Asn Leu Lys
225                 230                 235                 240

Gly Arg Trp Gln Gln Trp Ala Asp Glu His Val Gln Ser Gln Lys Leu
                245                 250                 255

Asn Pro Phe Ser Asp Glu Phe Asp Tyr Asp Leu Ala Met Ser Thr Arg
            260                 265                 270

Leu His Lys Gly Asp Glu Gly Tyr Gly Arg Pro Lys Glu Gly Ser Lys
        275                 280                 285

Thr Ala Glu Arg Ala Lys Arg Ala Glu Glu His Ile Tyr Arg Glu Ile

```
                290                 295                 300
Met Glu Leu Cys Phe Val Ile Arg Thr Met Ala Arg His Arg Arg Asp
305                 310                 315                 320

Gly Lys Ile Gln Val Thr Phe Gly Glu Leu Phe Asp Arg Tyr Val Arg
                325                 330                 335

Ile Ser Asp Lys Val Val Gly Ile Leu Met Arg Ala Arg Lys His Gly
                340                 345                 350

Leu Val His Phe Glu Gly Glu Met Leu Trp Gln Gly Arg Asp Asp His
                355                 360                 365

Val Val Ile Thr Leu Val Glu
                370                 375

<210> SEQ ID NO 5
<211> LENGTH: 612
<212> TYPE: DNA
<213> ORGANISM: Zebra Fish
<220> FEATURE:
<221> NAME/KEY: modified_base
<222> LOCATION: (497)
<223> OTHER INFORMATION: n = a, c, g or t/u

<400> SEQUENCE: 5
attaagacgg gaatcgtgac taaagctatt acgccgaagt gtaacgagtt tggaaaggat      60
ttggtgagcg tgattaagga gaagatcaac accaatcaac tgacgactga agacaccaaa     120
aatttcctag gaaatgaatc tcctactagg agacgctact gtgggggaa agcagggact      180 tttgttaaag caatcggacg gaaagaggga agtcgatgg gatcgcgaag tagcagtttg      240
gatgctgatg acagcggtct tggggaggaa gcatctctga gcgacaacag cgatctgaac     300
gagaacgaac ccaagaaaca tgtcaacaga cacaagatta agtgacaac gatgggtgac      360 ctgcggagcc gctggcagcg tttcgctgaa gatcacatgg agggccagaa gctcaacct      420 ttcagtgaag agtttgacta tgatcatgca atggccactc gactccacaa aggcgacgcg     480
ggctacggac gacccanaga aggatccaaa acagctcagc gagcagatcg agcccaaaag     540
cacatctacc gcgagatgga ggagatgtgc ttcatcatac gagacatggg ccagcaggac     600
aaacagggcc aa                                                         612

<210> SEQ ID NO 6
<211> LENGTH: 203
<212> TYPE: PRT
<213> ORGANISM: Zebra Fish

<400> SEQUENCE: 6

Ile Lys Thr Gly Ile Val Thr Lys Ala Ile Thr Pro Lys Cys Asn Glu
1               5                   10                  15

Phe Gly Lys Asp Leu Val Ser Val Ile Lys Glu Lys Ile Asn Thr Asn
                20                  25                  30

Gln Leu Thr Thr Glu Asp Thr Lys Asn Phe Leu Gly Asn Glu Ser Pro
            35                  40                  45

Thr Arg Arg Arg Tyr Cys Gly Gly Lys Ala Gly Thr Phe Val Lys Ala
        50                  55                  60

Ile Gly Arg Lys Glu Gly Lys Ser Met Gly Ser Arg Ser Ser Leu
65                  70                  75                  80

Asp Ala Asp Asp Ser Gly Leu Gly Glu Glu Ala Ser Leu Ser Asp Asn
                85                  90                  95

Ser Asp Leu Asn Glu Asn Glu Pro Lys Lys His Val Asn Arg His Lys
                100                 105                 110
```

```
Ile Lys Val Thr Thr Met Gly Asp Leu Arg Ser Arg Trp Gln Arg Phe
            115                 120                 125

Ala Glu Asp His Met Glu Gly Gln Lys Leu Asn Pro Phe Ser Glu Glu
        130                 135                 140

Phe Asp Tyr Asp His Ala Met Ala Thr Arg Leu His Lys Gly Asp Ala
145                 150                 155                 160

Gly Tyr Gly Arg Pro Lys Lys Asp Pro Lys Gln Leu Ser Glu Gln Ile
                165                 170                 175

Glu Pro Lys Ser Thr Ser Thr Ala Arg Trp Arg Cys Ala Ser Ser
            180                 185                 190

Tyr Glu Thr Trp Ala Ser Arg Thr Asn Arg Ala
            195                 200

<210> SEQ ID NO 7
<211> LENGTH: 489
<212> TYPE: DNA
<213> ORGANISM: Caenorhabditis elegans
<220> FEATURE:
<221> NAME/KEY: CDS
<222> LOCATION: (1)..(489)

<400> SEQUENCE: 7 atg tca att gca tgt gct aga att gat aaa aca att ttc aaa ttc aaa    48
Met Ser Ile Ala Cys Ala Arg Ile Asp Lys Thr Ile Phe Lys Phe Lys
1               5                   10                  15 gaa atg gag cag aat gta gcg act cag agc aaa gat gat gtg tat tcc    96
Glu Met Glu Gln Asn Val Ala Thr Gln Ser Lys Asp Asp Val Tyr Ser
            20                  25                  30 aaa gat ttt act caa aag aaa atg gac aag tcc agt agc gaa tat gga   144
Lys Asp Phe Thr Gln Lys Lys Met Asp Lys Ser Ser Ser Glu Tyr Gly
        35                  40                  45 cgg cca aaa cca gga act ctt aca gag caa aga gct aaa aaa gct gcc   192
Arg Pro Lys Pro Gly Thr Leu Thr Glu Gln Arg Ala Lys Lys Ala Ala
    50                  55                  60 gcc cac gtt cac aga gaa atg cta aca tta tgt gaa gtt gtg gag gat   240
Ala His Val His Arg Glu Met Leu Thr Leu Cys Glu Val Val Glu Asp
65                  70                  75                  80 tat ggt aaa caa gag aag gaa gga gat cca atc aga atc aca ttt gga   288
Tyr Gly Lys Gln Glu Lys Glu Gly Asp Pro Ile Arg Ile Thr Phe Gly
                85                  90                  95 aga ctt ttc aca att tat gtc aat att tct gat aag gta gtt gga acc   336
Arg Leu Phe Thr Ile Tyr Val Asn Ile Ser Asp Lys Val Val Gly Thr
            100                 105                 110 ctt ttg cga gct cgt aaa cac aaa atg ata gat ttt gaa gga gaa atg   384
Leu Leu Arg Ala Arg Lys His Lys Met Ile Asp Phe Glu Gly Glu Met
        115                 120                 125 tta ttt caa aag aga gat gat cat gtt att atc aca ctt tta ctc tct   432
Leu Phe Gln Lys Arg Asp Asp His Val Ile Ile Thr Leu Leu Leu Ser
    130                 135                 140 gga gca cag ctt aaa gag gct att cga gca cac gca gca gca aac cca   480
Gly Ala Gln Leu Lys Glu Ala Ile Arg Ala His Ala Ala Ala Asn Pro
145                 150                 155                 160 aag gaa taa                                                        489
Lys Glu

<210> SEQ ID NO 8
<211> LENGTH: 162
<212> TYPE: PRT
<213> ORGANISM: Caenorhabditis elegans
```

```
<400> SEQUENCE: 8

Met Ser Ile Ala Cys Ala Arg Ile Asp Lys Thr Ile Phe Lys Phe Lys
1               5                   10                  15

Glu Met Glu Gln Asn Val Ala Thr Gln Ser Lys Asp Asp Val Tyr Ser
            20                  25                  30

Lys Asp Phe Thr Gln Lys Lys Met Asp Lys Ser Ser Ser Glu Tyr Gly
        35                  40                  45

Arg Pro Lys Pro Gly Thr Leu Thr Glu Gln Arg Ala Lys Lys Ala Ala
    50                  55                  60

Ala His Val His Arg Glu Met Leu Thr Leu Cys Glu Val Val Glu Asp
65                  70                  75                  80

Tyr Gly Lys Gln Glu Lys Glu Gly Asp Pro Ile Arg Ile Thr Phe Gly
                85                  90                  95

Arg Leu Phe Thr Ile Tyr Val Asn Ile Ser Asp Lys Val Val Gly Thr
            100                 105                 110

Leu Leu Arg Ala Arg Lys His Lys Met Ile Asp Phe Glu Gly Glu Met
        115                 120                 125

Leu Phe Gln Lys Arg Asp Asp His Val Ile Ile Thr Leu Leu Leu Ser
    130                 135                 140

Gly Ala Gln Leu Lys Glu Ala Ile Arg Ala His Ala Ala Ala Asn Pro
145                 150                 155                 160

Lys Glu

<210> SEQ ID NO 9
<211> LENGTH: 399
<212> TYPE: PRT
<213> ORGANISM: Drosophila melanogaster

<400> SEQUENCE: 9

Met Thr Asp Val Ser His Glu Leu Gly Ala Leu Arg Phe Val Val Leu
1               5                   10                  15

Arg Tyr Leu Gln Asp Ser Pro Leu Ser Ser Lys Val Ala Met Phe Asn
            20                  25                  30

Asn Gln Ala Thr Gln His Lys Gln Ser Gln Leu Leu Asn Pro Phe Ser
        35                  40                  45

Gln Asp Gly Arg Ala Ala Ser Pro Lys Pro Thr Phe Ser Lys Asp Gln
    50                  55                  60

Tyr Gly Lys Pro Leu Ala Gly Ser Leu Thr Glu Met Arg Gly Gln Lys
65                  70                  75                  80

Ala Asn Ile His Val Met Lys Glu Met Leu Glu Leu Cys Gln Ile Ile
                85                  90                  95

Asn Ser Glu Gly Tyr Asp Val Lys Asp Glu Pro Thr Met Arg Val Ile
            100                 105                 110

Pro Phe Gly Glu Leu Phe Asn Val Ser Val Leu Phe Thr Ala Gly Ile
        115                 120                 125

Phe Phe Glu Lys Pro Ser Lys Leu Val Thr Ser Thr Leu Gln Ile Tyr
    130                 135                 140

Asn Tyr Ile Ser Asp Lys Val Val Gly Ile Leu Leu Arg Ala Arg Lys
145                 150                 155                 160

His Lys Leu Val Asp Phe Glu Gly Glu Met Leu Tyr Gln Arg Arg Asp
                165                 170                 175

Asp Asp Val Pro Val Phe Leu Leu Lys Pro Ile Lys Glu Ile Arg Ser
            180                 185                 190

Glu Met Glu Ala Lys Ile Glu Asp Ile Lys Arg Ala Ala Ser Pro Ala
```

-continued

```
            195                 200                 205
Pro Pro Gln Ser Thr Ser Val Leu Met Asp Arg Ser Ala His Glu Gln
    210                 215                 220

Lys Leu Lys Ser Arg Thr Pro Ser Pro Ala Val Gly Lys Ser Ala Lys
225                 230                 235                 240

Ser Lys Ser Ala Ser Pro Ala Pro Lys Ala Pro Val Pro Val Pro Ala
                245                 250                 255

Pro Ala Ala Glu Val Thr Pro Val Ala Gly Pro Thr Thr Ser Ala Glu
            260                 265                 270

Pro Ala Pro Val Ala Glu Ser Thr Met Ala Ala Val Pro Ala Pro Ser
        275                 280                 285

Thr Glu Pro Thr Pro Ala Thr Ala Pro Ala Ser Ser Thr Val Glu Ile
    290                 295                 300

Glu Pro Ala Lys Pro Glu Val Thr Glu Gln Ala Pro Val Ala Val Ile
305                 310                 315                 320

Val Thr Glu Ala Pro Ser Thr Glu Glu Thr Thr Pro Thr Thr Ser Glu
                325                 330                 335

Pro Gln Ala Glu Glu Ala Pro Ala Ala Val Ala Pro Ala Gly Pro Ala
            340                 345                 350

Asp Asp Leu Pro Thr Ile Val Ile Glu Ala Thr Ala Glu Phe Val Arg
        355                 360                 365

Thr Val Ser Val Glu Gln Leu Ala Pro Ser Pro Gly Thr Ala Ser Glu
    370                 375                 380

Ser Ser Pro Asp Gln Ser Gln Ser Gln Pro Glu Ser Thr Pro Ala
385                 390                 395
```

<210> SEQ ID NO 10
<211> LENGTH: 12
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
gatctgcggt ga                                                        12

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
agcactctcc agcctctcac cgca                                           24

<210> SEQ ID NO 12
<211> LENGTH: 12
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
gatctgttca tg                                                        12

<210> SEQ ID NO 13

```
-continued
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
accgacgtcg actatccatg aaca                                          24

<210> SEQ ID NO 14
<211> LENGTH: 13
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
gatctttcca tcg                                                      13

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
aggcaactgt gctatccgag ggaa                                          24
```

STARS—A MUSCLE-SPECIFIC ACTIN-BINDING PROTEIN

The present application claims benefit of priority to U.S. Provisional Ser. No. 60/404,706, filed Aug. 20, 2002, the entire contents of which are hereby incorporated by reference.

The government may own rights in the present invention pursuant to grant number RO1HL61544 from the National Institute of Health.

BACKGROUND OF THE INVENTION

1. Field of the Invention

The present invention relates generally to the fields of developmental biology and molecular biology. More particularly, it concerns an actin binding protein expressed specifically in striated muscle tissue.

2. Description of Related Art

The actin cytoskeleton influences diverse cellular processes, including motility, mitosis, contractility, cytokinesis, endocytosis and secretion (Burridge and Chrzanowska-Wodnicka, 1996; Schmidt and Hall, 1998; Pantaloni et al., 2001). Actin also participates in numerous transmembrane signaling systems by forming complexes with cell adhesion molecules and receptors (Juliano and Haskill, 1993; Calderwood et al., 2000). In addition, actin has been implicated in the control of gene transcription through its direct association with chromatin remodeling complexes (Rando et al., 2000) and through indirect mechanisms mediated by changes in cytoskeletal actin dynamics (Sotiropoulos et al., 1999).

Actin exists in monomeric (G-actin) and polymerized (F-actin) forms. The distribution of actin between these two forms is tightly regulated and is influenced by numerous actin-binding proteins which control actin dynamics by severing (i.e. ADF/cofilin), cross-linking (i.e. actinin, tropomyosin), and capping (i.e. tropomodulin at the point ends and capZ at the Z-line) actin (Cooper and Schafer, 2000). Members of the Rho GTPase family regulate cytoskeletal organization by stimulating actin polymerization and stress fiber formation when activated by extracellular signaling (Ridley and Hall, 1992). A number of Rho effector molecules, including Rho kinase/ROCK, mDia and phosphatidylinositol phosphate 5-kinase also participate in cytoskeletal organization (Kaibuchi et al., 1999; Maekawa et al., 1999; Narumiya et al., 1997; Yamamoto et al., 2001; Van Aelst and D'Souza-Schorey, 1997).

Recent studies showed that RhoA signaling stimulates the transcriptional activity of serum response factor (SRF) through a mechanism mediated by changes in actin dynamics (Sotiropoulos et al., 1999; Mack et al., 2001). SRF is a MADS-box transcription factor that regulates serum-inducible and muscle-specific gene expression by binding to a consensus sequence known a CArG box, CC(A/T)6GG (Treisman, 1995a; Treisman, 1995b). The spectrum of genes regulated by SRF is dictated by its association with serum-regulated and muscle-restricted cofactors (Treisman, 1994). In light of the unique and elaborate cytoskeletal organization of striated muscle cells, and the sensitivity of SRF to actin dynamics, it is tempting to speculate that cytoskeletal signals in striated muscle cells might regulate SRF activity in a muscle-specific manner.

SUMMARY OF THE INVENTION

In one aspect, the present invention provides an isolated STARS polypeptide, in particular a STARS polypeptide comprising an amino acid sequence of SEQ ID NO:2, 4, 6, 8 or 10. By way of illustration, the polynucleotide may have the nucleic acid sequence of SEQ ID NO:1, 3, 5, 7 or 9, or a complement thereof. The polynucleotide may further comprise a promoter operable in eukaryotic cells, for example, a promoter heterologous to the natural sequence of SEQ ID NO:1, 3, 5, 7 or 9. Exemplary promoters include hsp68, SV40, CMV, MKC, GAL4$_{UAS}$, HSV, and β-actin. The promoter may be a tissue specific promoter, such as a cardiac specific promoter.

In another embodiment, there is provided a nucleic acid of 15 to about 2000 base pairs comprising from about 15, 20, 25, 30, 40, 50, 100, 150, 250, 500, 1000, 2000 or more contiguous base pairs of SEQ ID NO:1, 3, 5, 7 or 9, or the complement thereof. Also provided is a peptide comprising 10, 15, 20, 25, 30, 50 or more contiguous amino acids of SEQ ID NO:2, 4, 6, 8 or 10.

In yet another embodiment, there is provided an expression construct comprising a polynucleotide encoding a STARS polypeptide operably linked to a regulatory sequence, for example, a STARS polypeptide having the sequence of SEQ ID NO:2, 4, 6, 8 or 10. In particular embodiments, the polynucleotide within the expression construct is under the control of a tissue specific promoter operable in eukaryotic cells where the promoter may be muscle specific. Exemplary tissue specific promoters include myosin light chain-2 promoter, α actin promoter, troponin 1 promoter, Na$^+$/Ca$^{2+}$ exchanger promoter, dystrophin promoter, creatine kinase promoter, α7 integrin promoter, brain natriuretic peptide promoter, αB-crystallin/small heat shock protein promoter, α myosin heavy chain promoter and atrial natriuretic factor promoter. The promoter may be an inducible promoter.

The expression construct may be comprised within a viral vector, for example, a retroviral vector, an adenoviral vector, and adeno-associated viral vector, a vaccinia viral vector, a herpesviral vector, a polyoma viral construct or a Sindbis viral vector. The expression construct may further comprise various regulatory sequences, such as, for example, a polyadenylation signal or the like. The expression construct may comprise a one or more additional polynucleotides encoding one or more additional polypeptides, under the control of the same or a different promoter.

In still another embodiment, there is provided a method of screening for modulators of STARS expression comprising (a) providing a cell in which a STARS promoter directs the expression of a polypeptide; (b) contacting said cell with a candidate modulator; and (c) measuring the effect of said candidate modulator on said polypeptide, wherein a difference in expression of said polypeptide, as compared to an untreated cell, indicates that said candidate modulator is a modulator of STARS expression. Measuring may comprise Northern analysis, PCR, RT-PCR, or immunologic detection of STARS (including ELISA and immunohistochemistry). The cell may be located in an animal. The cell type may be a myocyte, or more specifically, a cardiomyocyte. The modulator may increase or decrease expression. The polypeptide may be STARS or a screenable marker polypeptide.

In still yet another embodiment, there is provided a method of screening for modulators of STARS actin binding activity comprising (a) providing an active STARS preparation; (b) contacting said STARS preparation with a candidate modulator; and (c) measuring the actin binding activity of said STARS preparation, wherein a difference in actin binding activity of said STARS preparation, as compared to an untreated STARS preparation, indicates that said candidate modulator is a modulator of STARS actin binding activity. The screening may be performed in a cell free assay or in a cell. The binding may be determined by chromatographic separation or electrophoretic separation.

Further embodiments include a method of screening for an inhibitor of STARS-induced transcription comprising (a) providing a cell that expresses STARS and contains a STARS-regulated promoter linked to an indicator gene; (b) contacting said cell with a candidate modulator; and (c) measuring the effect of said candidate modulator on expression of said indicator gene, wherein a difference in expression of said polypeptide, as compared to an untreated cell, indicates that said candidate modulator is a modulator of STARS-induced transactivation. The cell may be a myocyte, for example, a cardiomyocyte. The promoter may be an SM22 promoter. The indicator gene may encode luciferase, β-galactosidase, CAT, or green fluorescent protein.

Also provided is a method of producing a STARS polypeptide in a cell comprising (a) transforming a cell with an expression cassette comprising a nucleic acid encoding STARS under the control of a promoter active in said cell; (b) culturing said cell under conditions suitable for expression of STARS. The cell may be, for example, a cardiomyocyte or a fibroblast, such as a cardiac fibroblast. The cell may be located in an animal. The transforming step may comprise infection with a viral vector. The transforming step may also comprise contacting the cell with a liposome comprising the expression cassette, electroporation, calcium phosphate precipitation, or protoplast fusion. The cell may be a prokaryotic or eukaryotic cell. The method may further comprise the step of purifying said STARS polypeptide away from other cellular components.

In other embodiments, there are provided a non-human transgenic animal comprising a selectable or screenable marker protein under the control of a STARS promoter; a non-human transgenic animal comprising a STARS encoding nucleic acid under the control of an inducible promoter; a non-human transgenic animal comprising a STARS encoding nucleic acid under the control of a constitutive promoter; and a non-human transgenic animal lacking at least one STARS allele, or both.

In other embodiments, there are provided a method of inhibiting STARS activity comprising contacting a cell expressing STARS with a compound that inhibits STARS activity. The compound may be a nucleic acid antisense to a STARS regulatory or coding region, a ribozyme that selectively cleaves a STARS transcript, a small molecule inhibitor, or a single chain antibody that binds immunologically to STARS.

In yet other embodiments, methods of treating cardiac hypertrophy and dilated cardiomyopathy comprising decreasing STARS activity in heart cells of a subject are provided. In one aspect, STARS activity is decreased by delivering an expression vector comprising a polynucleotide encoding an antisense STARS construct, a STARS ribozyme or an anti-STARS single-chain antibody to said subject. The expression vector may be a non-viral or a viral vector. The viral vector may be an adenoviral construct, a retroviral construct, an adeno-associated viral construct, a herpesviral construct, a vaccinia viral construct, a polyoma viral construct or a Sindbis viral vector. The viral vector may be a replication-defective adenovirus.

By way of illustration, the step of delivering the expression construct may comprise introducing a viral vector comprising the nucleic acid into the heart of the mammal by direct injection into the heart tissue. The step of delivering the expression construct may also comprise introducing the expression construct into the lumen of at least one vessel that supplies blood to the heart. Delivering the expression construct may further comprise administering a second antihypertophic drug, or decreasing STARS activity in hearts cells of a subject.

In additional embodiments, there are provided:
a method of producing a modulator of STARS expression comprising: (a) providing a cell in which a STARS promoter directs the expression of a polypeptide; (b) contacting said cell with a candidate modulator; (c) measuring the effect of said candidate modulator on said polypeptide, wherein a difference in expression of said polypeptide, as compared to an untreated cell, indicates that said candidate modulator is a modulator of STARS expression; and (d) producing said modulator;

a method of producing a modulator of STARS actin binding activity comprising: (a) providing an active STARS preparation; (b) contacting said STARS preparation with a candidate modulator; (c) measuring the actin binding activity of said STARS preparation, wherein a difference in actin binding activity of said STARS preparation, as compared to an untreated STARS preparation, indicates that said candidate modulator is a modulator of STARS acting binding activity; and (d) producing said modulator;

a modulator of STARS expression identified according to the method comprising: (a) providing a cell in which a STARS promoter directs the expression of a polypeptide; (b) contacting said cell with a candidate modulator; and (c) measuring the effect of said candidate modulator on said polypeptide, wherein a difference in expression of said polypeptide, as compared to an untreated cell, indicates that said candidate modulator is a modulator of STARS expression;

a modulator of STARS actin binding activity identified according to the method comprising: (a) providing a STARS preparation; (b) contacting said STARS preparation with a candidate modulator; and (c) measuring the actin binding activity of said STARS preparation, wherein a difference in actin binding activity of said STARS preparation, as compared to an untreated STARS preparation, indicates that said candidate modulator is a modulator of STARS actin binding activity;

There also are provided an antibody that binds immunologically to STARS, a polyclonal antibody preparation of antibodies that bind immunologically to STARS, and a hybridoma cell that produces a monoclonal antibody that binds immunologically to STARS.

In other embodiments, there are provided a method of treating myocardial infarct comprising decreasing STARS activity in heart cells of a subject; a method of preventing cardiac hypertrophy and dilated cardiomyopathy comprising decreasing STARS activity in heart cells of a subject; a method of inhibiting progression of cardiac hypertrophy comprising decreasing STARS activity in heart cells of a subject; a method of treating heart failure comprising decreasing STARS activity in heart cells of a subject; a method of inhibiting progression of heart failure comprising decreasing STARS activity in heart cells of a subject; a method of increasing exercise tolerance in a subject with heart failure or cardiac hypertrophy comprising decreasing STARS activity in heart cells of a subject; a method of reducing hospitalization in a subject with heart failure or cardiac hypertrophy comprising decreasing STARS activity in heart cells of a subject; a method of improving quality of life in a subject with heart failure or cardiac hypertrophy comprising decreasing STARS activity in heart cells of a subject; a method of decreasing morbidity in a subject with heart failure or cardiac hypertrophy comprising decreasing STARS activity in heart cells of a subject; and a method of decreasing mortality in a subject with heart failure or cardiac hypertrophy comprising decreasing STARS in heart cells of a subject.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1—Deduced amino acid sequence and homology of STARS to other predicted proteins. Deduced amino acid sequence of mouse STARS (Accession numbers AF504061 and AAM28877) and homology with sequences from other species, including human (AF503617 and AAM27268).

FIG. 2A: In situ hybridization shows the specific expression of STARS transcripts in the heart tube of E8.75 mouse embryo h, head; ht, heart. FIG. 2B: Northern blot analysis of STARS transcripts in adult mouse and human tissues detected with Clontech multi tissue blots. FIG. 2C: Northern blot analysis of STARS and GAPDH transcripts during differentiation of the C2 muscle cell line. At day 0, myoblasts were maintained in growth medium and were then transferred to differentiation medium for the indicated number of days. FIG. 2D: Northern analysis of STARS and GAPDH transcripts in hearts from wild-type (WT) and α-MHC-calcineurin transgenic (Tg) mice at 3 and 6 months of age. Twenty μg total RNA was applied to each lane in FIG. 2C and FIG. 2D. Positions of 18S and 28S RNA are indicated.

FIG. 3A: Western blot analysis using anti-STARS antibody detected endogenous STARS protein in adult mouse heart lysate and in COS cells transfected with STARS expression vector. FIG. 3B: Localization of STARS to the actin thin-filament and stress fibers in cardiomyocytes. Rat neonatal cardiomyocytes were infected with GFP adenovirus (a, b) or STARS adenovirus (c–h). Anti STARS antibody does not detect GFP protein nor endogenous STARS (a). Overexpressed STARS is stained with anti-STARS antibody followed by fluoresceine anti-rabbit IgG secondary actibody (c, f). Z-band is stained with anti α-actinin antibody followed by Texas red conjugated secondary antibody (b, d). STARS was localized in the sarcomere (c and f), but not at the Z-band, as demonstrated by the lack of overlap with α-actinin (d, e). Phaloidin-TRITC shows the thin filaments (g). STARS superimposes with the thin filament, but not at Z-lband (h). Bars: 10 μm (e, a–e in the same magnification), 5 μm (h)

FIG. 4A: COS cells were transiently transfected with an expression vector encoding STARS (wt) or deletion mutants with an N-terminal Myc-tag. The subcellular distribution of STARS was determined by immunofluorescence using fluoresceine anti-mouse IgG secondary antibody (c, f, i and l). Cells were also stained with Phalloidin-TRITC to visualize F-actin (a, b, d, g, j and m). F-actin and stress fibers were in COS cells transfected with an empty vector (a, b). STARS (wt), shows the exact same pattern of phalloidin staining; strongly associates with F-actin and induces extremely thick bundles (c, d, e). Numerous tumble stress fibers are also induced. (f, g, h). Homologous region C142 induces actin bundles (i, j, k). In contraast, homologous reigon deletion mutant C96 just associates with actin stress fibers (l, m, n). Bar indicates 20 μm. FIG. 4B: COS cells were transiently transfected with an expression vector encoding STARS or the indicated deletion mutants with Myc-epitope tags. Cell extracts were then immunoprecipitated with a rabbit polyclonal anti-Myc antibody and immunoprecipitates were analyzed by Western blot using anti-actin monoclonal antibody (top) or anti-Myc monoclonal antibody (bottom).

FIG. 6A: COS and F9 cells were transiently transfected with an SM22-luciferase reporter or the same reporter containing mutations in the CArG-boxes within the SM22 promoter (mutSM22), and an STARS expression vector. FIG. 6B: COS cells were transiently transfected with the indicated reporter plasmids with and without an STARS expression plasmid. FIG. 6C: COS cells were transiently transfected with SM22-luciferase and expression plasmids encoding the indicated STARS mutants. FIG. 6D: COS cells were transiently transfected with SM22-luciferase in the presence and absence of STARS and the indicated agents. FIG. 6E: COS cells were transiently transfected with SM22-luciferase and a STARS or RhoA (L63) expression vector. FIG. 6F: COS cells were transiently transfected with SM22-luciferase and a STARS expression vector in the presence of Y-27632 or a C3 expression vector. Luciferase activity was determined on cell extracts and is expressed as the level of activity relative to that in cells transfected with the indicated reporters without STARS.

DESCRIPTION OF ILLUSTRATIVE EMBODIMENTS

Figure 2:
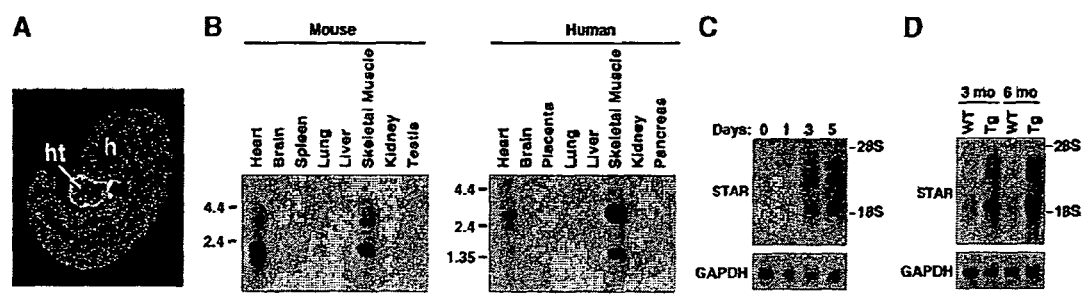
FIG. 2—Expression of STARS in cardiac and skeletal muscle.

Heart disease and its manifestations, including coronary artery disease, myocardial infarction, congestive heart failure and cardiac hypertrophy, presents a major health risk in the United States today. The cost to diagnose, treat and support patients suffering from these diseases is well into the billions of dollars. Two particularly severe manifestations of heart disease are myocardial infarction and cardiac hypertrophy. With respect to myocardial infarction, typically an acute thrombotic coronary occlusion occurs in a coronary artery as a result of atherosclerosis and causes myocardial cell death. Because cardiomyocytes, the heart muscle cells, are terminally differentiated and generally incapable of cell division, they are generally replaced by scar tissue when they die during the course of an acute myocardial infarction. Scar tissue is not contractile, fails to contribute to cardiac function, and often plays a detrimental role in heart function by expanding during cardiac contraction, or by increasing the size and effective radius of the ventricle, for example, becoming hypertrophic. With respect to cardiac hypertrophy, one theory regards this as a disease that resembles aberrant development and, as such, raises the question of whether developmental signals in the heart can contribute to hypertrophic disease.

The inventors have described herein a novel actin-binding protein designated as STARS (striated muscle activator of Rho signaling), which is expressed specifically in cardiac and skeletal muscle cells and is upregulated in response to calcineurin signaling during cardiac hypertrophy. STARS is identified in a differential cDNA screen for unknown genes expressed in the early embryonic heart. It is localized to the thin filament of the sarcomere and to actin stress fibers where it promotes actin bundling. STARS stimulates the transcriptional activity of SRF through a mechanism that requires actin bundling and Rho kinase activation. STARS provides a mechanism for selectively enhancing the transcriptional activity of SRF in muscle cells and for linking changes in actin dynamics to gene transcription. These findings indicate that STARS acts as a muscle-specific transducer of cytoskeletal signals that stimulate SRF activity.

I. STARS Peptides and Polypeptides

STARS is a novel and evolutionarily conserved actin-binding/bundling protein expressed specifically in striated muscle. STARS localizes to the thin filament of the sarcomere and to actin stress fibers. Stabilization of the actin cytoskeleton by STARS stimulates SRF-dependent transcription through a mechanism that involves RhoA signaling.

STARS contains no recognizable protein motifs and represents a new type of actin-binding protein. Deletion mutants of STARS indicate that there are multiple, nonoverlapping regions of the protein that can mediate association with actin stress fibers in vivo. However, only the conserved carboxy-terminal domain bundles F-actin and binds actin with sufficient affinity to be detect in co-immunoprecipitation assays. The high conservation of this region between vertebrate and invertebrate proteins indicates that this activity has been evolutionarily conserved. It should also be noted that STARS associates with actin of the thin-filament, but not the Z-line. This raises the possibility that the STARS-binding region of actin may be masked on the Z-line, possibly because of numerous other actin-binding proteins localized to this structure (Bang et al., 2001).

STARS expression is initiated in cardiac and skeletal muscle during the period of myofibrillogenesis when the myofibrillar components become assembled into the functional sarcomere (Ehler et al., 1999; Gregorio and Antin, 2000). Considering the timing of its expression and its actin-binding properties, STARS may participate in sarcomere assembly by inducing actin polymerization and cross-linking during striated muscle development.

Consistent with recent studies implicating actin dynamics in the control of SRF dependent transcription (Sotiropoulos et al., 1999; Wei et al., 2001; Mack et al., 2001), STARS stimulates the activity of SRF. The conserved carboxy-terminal region of STARS is both necessary and sufficient for SRF activation and actin bundling; the correlation between these activities argues that the effects of STARS on SRF are coupled to its effects on the cytoskeleton. Stimulation of SRF activity is observed with native muscle promoters, as well as with an artificial promoter containing multimerized CArG-boxes. However, STARS does not activate all SRF-dependent promoters equally, which indicates that additional promoter-specific transcription factors modulate the responsiveness of SRF to STARS-dependent signaling.

In addition to an entire STARS molecule, the present invention also relates to fragments of the polypeptides that may or may not retain several of the functions described below. Fragments, including the N-terminus of the molecule, may be generated by genetic engineering of translation stop sites within the coding region (discussed below). Alternatively, treatment of the STARS with proteolytic enzymes, known as proteases, can produce a variety of N-terminal, C-terminal and internal fragments. Examples of fragments may include contiguous residues of SEQ ID NOS:2, 4, 6, 8, and 10 of 6, 7, 8, 9, 10, 11, 12, 13, 14, 15, 16, 17, 18, 19, 20, 21, 22, 23, 24, 25, 30, 35, 40, 45, 50, 55, 60, 65, 75, 80, 85, 90, 95, 100, 200, 300, 400 or more amino acids in length. These fragments may be purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

A. Variants of STARS

Amino acid sequence variants of the polypeptide can be substitutional, insertional or deletion variants. Deletion variants lack one or more residues of the native protein that are not essential for function or immunogenic activity, and are exemplified by the variants lacking a transmembrane sequence described above. Another common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventors that various changes may be made in the DNA sequences of genes without appreciable loss of their biological utility or activity, as discussed below. Table 1 shows the codons that encode particular amino acids.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5+1); alanine (−0.5); histidine*−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within 2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take several of the foregoing characteristics into consideration are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide-containing molecules that mimic elements of protein secondary structure (Johnson et al., 1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of STARS, but with altered and even improved characteristics.

B. Domain Switching

Domain switching involves the generation of chimeric molecules using different but, in this case, related polypeptides. These molecules may have additional value in that these "chimeras" can be distinguished from natural molecules, while possibly providing the same function. For example, any of the various homologs from other species provide suitable candidates for domain switching experiments.

C. Fusion Proteins

A specialized kind of insertional variant is the fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions.

D. Purification of Proteins

It will be desirable to purify STARS or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography, polyacrylamide gel electrophoresis, and isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

E. Synthetic Peptides

The present invention also describes smaller STARS-related peptides for use in various embodiments of the present invention. Because of their relatively small size, the peptides of the invention can also be synthesized in solution or on a solid support in accordance with conventional techniques. Various automatic synthesizers are commercially available and can be used in accordance with known protocols. See, for example, Stewart and Young (1984); Tam et al. (1983); Merrifield (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

F. Antigen Compositions

The present invention also provides for the use of STARS proteins or peptides as antigens for the immunization of animals relating to the production of antibodies. It is envisioned that STARS, or portions thereof, will be coupled, bonded, bound, conjugated or chemically-linked to one or more agents via linkers, polylinkers or derivatized amino acids. This may be performed such that a bispecific or multivalent composition or vaccine is produced. It is further envisioned that the methods used in the preparation of these compositions will be familiar to those of skill in the art and should be suitable for administration to animals, i.e., pharmaceutically acceptable. Preferred agents as the carriers are keyhole limpet hemocyannin (KLH) or bovine serum albumin (BSA).

II. Nucleic Acids

The present invention also provides, in another embodiment, genes encoding STARS. Genes for mouse, human, zebrafish, Drosophila or c. elegans have been identified. See, for example, SEQ ID NOS: 1, 3, 5, 7 and 9 respectively. The present invention is not limited in scope to these genes, however, as one of ordinary skill in the art could, using these nucleic acids, readily identify related homologs in these and various other species (e.g., rat, rabbit, dog, monkey, gibbon, human, chimp, ape, baboon, cow, pig, horse, sheep, cat and other species).

In addition, it should be clear that the present invention is not limited to the specific nucleic acids disclosed herein. As discussed below, a "STARS gene" may contain a variety of different bases and yet still produce a corresponding polypeptide that is functionally indistinguishable, and in some cases structurally, from the human and mouse genes disclosed herein.

Similarly, any reference to a nucleic acid should be read as encompassing a host cell containing that nucleic acid and, in some cases, capable of expressing the product of that nucleic acid. In addition to therapeutic considerations, cells expressing nucleic acids of the present invention may prove useful in the context of screening for agents that induce, repress, inhibit, augment, interfere with, block, abrogate, stimulate or enhance the activity of STARS.

A. Nucleic Acids Encoding STARS

Nucleic acids according to the present invention may encode an entire STARS gene, a domain of STARS, or any other fragment of STARS as set forth herein. The nucleic acid may be derived from genomic DNA, i.e., cloned directly from the genome of a particular organism. In preferred embodiments, however, the nucleic acid would comprise complementary DNA (cDNA). Also contemplated is a cDNA plus a natural intron or an intron derived from another gene; such engineered molecules are sometime referred to as "mini-genes." At a minimum, these and other nucleic acids of the present invention may be used as molecular weight standards in, for example, gel electrophoresis.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that a given STARS from a given species may be represented by natural variants that have slightly different nucleic acid sequences but, nonetheless, encode the same protein (see Table 1 below).

As used in this application, the term "a nucleic acid encoding a STARS" refers to a nucleic acid molecule that has been isolated free of total cellular nucleic acid. In preferred embodiments, the invention concerns a nucleic acid sequence essentially as set forth in SEQ ID NOS: 1, 3, 5, 7 or 9 (mouse, human, zebrafish, Drosophila or c. elegans respectively). The term "as set forth in SEQ ID NOS: 1 or 3, 5, 7 or 9" means that the nucleic acid sequence substantially corresponds to a portion of SEQ ID NO:1 or 3, 5, 7 or 9. The term "functionally equivalent codon" is used herein to refer to codons that encode the same amino acid, such as the six codons for arginine or serine (Table 1, below), and also refers to codons that encode biologically equivalent amino acids, as discussed in the following pages.

TABLE 1

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |

TABLE 1-continued

| Amino Acids | | | Codons |
|---|---|---|---|
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

Allowing for the degeneracy of the genetic code, sequences that have at least about 50%, usually at least about 60%, more usually about 70%, most usually about 80%, preferably at least about 90% and most preferably about 95% of nucleotides that are identical to the nucleotides of SEQ ID NOS:1 or 3, 5, 7 or 9 are contemplated. Sequences that are essentially the same as those set forth in SEQ ID NOS:1, 3, 5, 7 or 9 may also be functionally defined as sequences that are capable of hybridizing to a nucleic acid segment containing the complement of SEQ ID NOS:1, 3, 5, 7 or 9 under standard conditions.

The DNA segments of the present invention include those encoding biologically functional equivalent STARS proteins and peptides, as described above. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

B. Oligonucleotide Probes and Primers

Naturally, the present invention also encompasses DNA segments that are complementary, or essentially complementary, to the sequence set forth in SEQ ID NOS:1, 3, 5, 7 or 9. Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NOS:1, 3, 5, 7 or 9 under relatively stringent conditions such as those described herein. Such sequences may encode entire STARS proteins or functional or non-functional fragments thereof.

Alternatively, the hybridizing segments may be shorter oligonucleotides. Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides encoding 250, 500, 1000, 1212, 1500, 2000, 2500, 3000 or 5000 bases and longer are contemplated as well. Such oligonucleotides will find use, for example, as probes in Southern and Northern blots and as primers in amplification reactions.

Suitable hybridization conditions will be well known to those of skill in the art. In certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 µM $MgCl_2$, at temperatures ranging from approximately 40° C. to about 72° C. Formamide and SDS also may be used to alter the hybridization conditions.

One method of using probes and primers of the present invention is in the search for genes related to STARS or, more particularly, homologs of STARS from other species. Normally, the target DNA will be a genomic or cDNA library, although screening may involve analysis of RNA molecules. By varying the stringency of hybridization, and the region of the probe, different degrees of homology may be discovered.

Another way of exploiting probes and primers of the present invention is in site-directed, or site-specific mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique typically employs a bacteriophage vector that exists in both a single-stranded and double-stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double-stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization conditions, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

C. Antisense Constructs

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50–200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

D. Ribozymes

Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cook, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cook et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cook et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

E. Vectors for Cloning, Gene Transfer and Expression

Within certain embodiments expression vectors are employed to express a STARS polypeptide product, which can then be purified and, for example, be used to vaccinate animals to generate antisera or monoclonal antibody with which further studies may be conducted. In other embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

(i) Regulatory Elements

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

In preferred embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the STARSt site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the STARSt site itself helps to fix the place of initiation.

Additional promoter elements regulate the frequency of transcriptional initiation. Typically, these are located in the region 30–110 bp upstream of the STARSt site, although a number of promoters have recently been shown to contain functional elements downstream of the STARSt site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

In various embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose.

By employing a promoter with well-known properties, the level and pattern of expression of the protein of interest following transfection or transformation can be optimized. Further, selection of a promoter that is regulated in response to specific physiologic signals can permit inducible expression of the gene product. Tables 2 and 3 list several regulatory elements that may be employed, in the context of the present invention, to regulate the expression of the gene of interest. This list is not intended to be exhaustive of all the possible elements involved in the promotion of gene expression but, merely, to be exemplary thereof.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding a gene of interest in an expression construct (Table 2 and Table 3). Additionally, any other promoter/enhancer combination (for example, as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 2

Promoter and/or Enhancer

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Green et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |

TABLE 2-continued

Promoter and/or Enhancer

| Promoter/Enhancer | References |
|---|---|
| Collagenase | Pinkert et al., 1987; Angel et al., 1987a |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $\alpha_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Change et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987; Glue et al., 1988 |
| Hepatitis B Virus | Bulla et al., 1986; Jameel et al., 1986; Shaul et al., 1987; Spandau et al., 1988; Vannice et al., 1988 |
| Human Immunodeficiency Virus | Muessing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 3

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1991; Lee et al., 1981; Majors et al., 1983; Chandler et al., 1983; Lee et al., 1984; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

Of particular interest are muscle specific promoters, and more particularly, cardiac specific promoters. These include the myosin light chain-2 promoter (Franz et al., 1994; Kelly et al., 1995), the α actin promoter (Moss et al., 1996), the troponin 1 promoter (Bhavsar et al., 1996); the $Na^+/Ca^{2+}$ exchanger promoter (Barnes et al., 1997), the dystrophin promoter (Kimura et al., 1997), the creatine kinase promoter (Ritchie, M. E., 1996), the α7 integrin promoter (Ziober & Kramer, 1996), the brain natriuretic peptide promoter (LaPointe et al., 1996), the α B-crystallin/small heat shock protein promoter (Gopal-Srivastava, R., 1995), and a myosin heavy chain promoter (Yamauchi-Takihara et al., 1989) and the ANF promoter (LaPointe et al., 1988).

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

(ii) Selectable Markers

In certain embodiments of the invention, the cells contain nucleic acid constructs of the present invention, a cell may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

(iii) Multigene Constructs and IRES

In certain embodiments of the invention, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornaovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

(iv) Delivery of Expression Constructs

There are a number of ways in which expression constructs may be introduced into cells. In certain embodiments of the invention, a vector (also referred to herein as a gene delivery vector) is employed to deliver the expression construct. By way of illustration, in some embodiments, the vector comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene delivery vectors were DNA viruses including the papovaviruses (simian virus 40, bovine papilloma virus, and polyoma) (Ridgeway, 1988; Baichwal and Sugden, 1986). Generally, these have a relatively low capacity for foreign DNA sequences and have a restricted host spectrum. They can accommodate only up to 8 kb of foreign genetic material but can be readily introduced in a variety of cell lines and laboratory animals (Nicolas and Rubenstein, 1988; Temin, 1986). Where viral vectors are employed to deliver the gene or genes of interest, it is generally preferred that they be replication-defective, for example as known to those of skill in the art and as described further herein below.

One of the preferred methods for in vivo delivery of expression constructs involves the use of an adenovirus expression vector. "Adenovirus expression vector" is meant to include those constructs containing adenovirus sequences sufficient to (a) support packaging of the construct and (b) to express a polynucleotide that has been cloned therein. In this context, expression does not require that the gene product be synthesized.

In preferred embodiments, the expression vector comprises a genetically engineered form of adenovirus. Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage and are able to infect non-dividing cells such as, for example, cardiomyocytes. So far, adenoviral infection appears to be linked only to mild disease such as acute respiratory disease in humans.

Adenovirus is particularly suitable for use as a gene delivery vector because of its mid-sized genome, ease of manipulation, high titer, wide target cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is important to minimize this possibility by, for example, reducing or eliminating adnoviral sequence overlaps within the system and/or to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the E3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of such adenovirus vectors is about 7.5 kb, or about 15% of the total length of the vector. Additionally, modified adenoviral vectors are now available which have an even greater capacity to carry foreign DNA.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, a preferred helper cell line is 293.

Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be selected from any of the 42 different known serotypes or subgroups A–F. Adenovirus type 5 of subgroup C is a preferred STARSting material for obtaining a replication-defective adenovirus vector for use in the present invention. This is, in part, because Adenovirus type 5 is a human adenovirus about which a great deal of biochemical and genetic information is known, and it has historically been used for most constructions employing adenovirus as a vector.

As stated above, a preferred adenoviral vector according to the present invention lacks an adenovirus E1 region and thus, is replication. Typically, it is most convenient to introduce the polynucleotide encoding the gene of interest at the position from which the E1-coding sequences have been removed. However, the position of insertion of the construct within the adenovirus sequences is not critical to the invention. Further, other adenoviral sequences may be deleted and/or inactivated in addition to or in lieu of the E1 region. For example, the E2 and E4 regions are both necessary for adenoviral replication and thus may be modified to render an adenovirus vector replication-defective, in which case a helper cell line or helper virus complex may employed to provide such deleted/inactivated genes in trans. The polynucleotide encoding the gene of interest may alternatively be inserted in lieu of a deleted E3 region such as in E3 replacement vectors as described by Karlsson et al. (1986), or in a deleted E4 region where a helper cell line or helper virus complements the E4 defect. Other modifications are known to those of skill in the art and are likewise contemplated herein.

Adenovirus is easy to grow and manipulate and exhibits broad host range in vitro and in vivo. This group of viruses can be obtained in high titers, e.g., $10^9$–$10^{12}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies indicated that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include administration via intracoronary catheter into one or more coronary arteries of the heart (Hammond, et al., U.S. Pat. Nos. 5,792,453 and 6,100,242) trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact-sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This indicated that large portions of the genome could be replaced with foreign genetic material. The hepatotropism and persistence (integration) were particularly attractive properties for liver-directed gene transfer. Chang et al., recently introduced the chloramphenicol acetyltransferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. In general, viral vectors accomplish delivery of the expression construct by infecting the target cells of interest. Alternatively to incorporating the expression construct into the genome of a viral vector, the expression construct may be encapsidated in the infectious viral particle.

Several non-viral gene delivery vectors for the transfer of expression constructs into mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression vector may simply consist of naked recombinant DNA or plasmids comprising the expression construct. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the invention, transferring of a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome, another non-viral gene delivery vector. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al, 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0 273 085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type by any number of receptor-ligand systems with or without liposomes. For example, epidermal growth factor (EGF) may be used as the receptor for mediated delivery of a nucleic acid into cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

III. Generating Antibodies Reactive with STARS

In another aspect, the present invention contemplates an antibody that is immunoreactive with a STARS molecule of the present invention, or any portion thereof. An antibody can be a polyclonal or a monoclonal antibody. In a preferred embodiment, an antibody is a monoclonal antibody. Means for preparing and characterizing antibodies are well known in the art (see, e.g., Harlow and Lane, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a non-human animal including rabbits, mice, rats, hamsters, pigs or horses. Because of the relatively large blood volume of rabbits, a rabbit is a preferred choice for production of polyclonal antibodies.

Antibodies, both polyclonal and monoclonal, specific for isoforms of antigen may be prepared using conventional immunization techniques, as will be generally known to those of skill in the art. A composition containing antigenic epitopes of the compounds of the present invention can be used to immunize one or more experimental animals, such as a rabbit or mouse, which will then proceed to produce specific antibodies against the compounds of the present invention. Polyclonal antisera may be obtained, after allowing time for antibody generation, simply by bleeding the animal and preparing serum samples from the whole blood.

It is proposed that the monoclonal antibodies of the present invention will find useful application in standard immunochemical procedures, such as ELISA and Western blot methods and in immunohistochemical procedures such as tissue staining, as well as in other procedures which may utilize antibodies specific to STARS-related antigen epitopes. Additionally, it is proposed that monoclonal antibodies specific to the particular STARS of different species may be utilized in other useful applications In general, both polyclonal and monoclonal antibodies against STARS may be used in a variety of embodiments. For example, they may be employed in antibody cloning protocols to obtain cDNAs or genes encoding other STARS. They may also be used in inhibition studies to analyze the effects of STARS related peptides in cells or animals. STARS antibodies will also be useful in immunolocalization studies to analyze the distribution of STARS during various cellular events, for example, to determine the cellular or tissue-specific distribution of STARS polypeptides under different points in the cell cycle. A particularly useful application of such antibodies is in purifying native or recombinant STARS, for example, using an antibody affinity column. The operation of all such immunological techniques will be known to those of skill in the art in light of the present disclosure.

Means for preparing and characterizing antibodies are well known in the art (see, e.g., Harlow and Lane, 1988; incorporated herein by reference). More specific examples of monoclonal antibody preparation are given in the examples below.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bisbiazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified STARS protein, polypeptide or peptide or cell expressing high levels of STARS. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bu1; for rats, one may use R210.RCY3, Y3-Ag 1.2.3, IR983F and 4B210; and U-266, GM1500-GRG2, LICR-LON-HMy2 and UC729–6 are all useful in connection with cell fusions.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al., (1977). The use of electrically induced fusion methods is also appropriate (Goding, 1986).

Fusion procedures usually produce viable hybrids at low frequencies, around $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

IV. Diagnosing and Treating Defects in STARS

The inventors believe that STARS plays an important role in the development of cardiac tissue and, further, in the mechanisms of heart disease. Thus, in another embodiment, there are provided methods for diagnosing defects in STARS expression and function. More specifically, point mutations, deletions, insertions or regulatory pertubations relating to STARS, as well as increases or decrease in levels of expression, may be assessed using standard technologies, as described below.

A. Genetic Diagnosis

One embodiment of the instant invention comprises a method for detecting variation in the expression of STARS. This may comprise determining the level of STARS or determining specific alterations in the expressed product.

A suitable biological sample can be any tissue or fluid. Various embodiments include cells of the skin, muscle, facia, brain, prostate, breast, endometrium, lung, head & neck, pancreas, small intestine, blood cells, liver, testes, ovaries, colon, skin, stomach, esophagus, spleen, lymph node, bone marrow or kidney. Other embodiments include fluid samples such as peripheral blood, lymph fluid, ascites, serous fluid, pleural effusion, sputum, cerebrospinal fluid, lacrimal fluid, stool or urine.

Nucleic acid used is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Various types of defects may be identified by the present methods. Thus, "alterations" should be read as including deletions, insertions, point mutations and duplications. Point mutations result in stop codons, frameshift mutations or amino acid substitutions. Somatic mutations are those occurring in non-germline tissues. Germ-line mutations can occur in any tissue and are inherited. Mutations in and outside the coding region also may affect the amount of STARS produced, both by altering the transcription of the gene or in destabilizing or otherwise altering the processing of either the transcript (mRNA) or protein.

It is contemplated that other mutations in the STARS genes may be identified in accordance with the present invention. A variety of different assays are contemplated in this regard, including but not limited to, fluorescent in situ hybridization (FISH), direct DNA sequencing, PFGE analysis, Southern or Northern blotting, single-stranded conformation analysis (SSCA), RNAse protection assay, allele-specific oligonucleotide (ASO), dot blot analysis, denaturing gradient gel electrophoresis, RFLP and PCR™-SSCP.

(i) Primers and Probes

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred. Probes are defined differently, although they may act as primers. Probes, while perhaps capable of priming, are designed to binding to the target DNA or RNA and need not be used in an amplification process.

In preferred embodiments, the probes or primers are labeled with radioactive species ($^{32}P$, $^{14}C$, $^{35}S$, $^{3}H$, or other label), with a fluorophore (rhodamine, fluorescein) or a chemillumiscent (luciferase).

(ii) Template Dependent Amplification Methods

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in its entirety.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641 filed Dec. 21, 1990. Polymerase chain reaction methodologies are well known in the art.

Another method for amplification is the ligase chain reaction ("LCR"), disclosed in EPO No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Methods based on ligation of two (or more) oligonucleotides in the presence of nucleic acid having the sequence of the resulting "di-oligonucleotide", thereby amplifying the di-oligonucleotide, may also be used in the amplification step of the present invention. Wu et al., (1989), incorporated herein by reference in its entirety.

(iii) Southern/Northern Blotting

Blotting techniques are well known to those of skill in the art. Southern blotting involves the use of DNA as a target, whereas Northern blotting involves the use of RNA as a target. Each provide different types of information, although cDNA blotting is analogous, in many aspects, to blotting or RNA species.

Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will binding a portion of the target sequence under renaturing conditions. Unbound probe is then removed, and detection is accomplished as described above.

(iv) Separation Methods

It normally is desirable, at one stage or another, to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

(v) Detection Methods

Products may be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by a labeled probe. The techniques involved are well known to those of skill in the art and can be found in many standard books on molecular protocols. See Sambrook et al., 1989. For example, chromophore or radiolabel probes or primers identify the target during or following amplification.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

In addition, the amplification products described above may be subjected to sequence analysis to identify specific kinds of variations using standard sequence analysis techniques. Within certain methods, exhaustive analysis of genes is carried out by sequence analysis using primer sets designed for optimal sequencing (Pignon et al, 1994). The present invention provides methods by which any or all of these types of analyses may be used. Using the sequences disclosed herein, oligonucleotide primers may be designed to permit the amplification of sequences throughout the STARS genes that may then be analyzed by direct sequencing.

(vi) Kit Components

All the essential materials and reagents required for detecting and sequencing STARS and variants thereof may be assembled together in a kit. This generally will comprise preselected primers and probes. Also included may be enzymes suitable for amplifying nucleic acids including various polymerases (RT, Taq, Sequenase™ etc.), deoxynucleotides and buffers to provide the necessary reaction mixture for amplification. Such kits also generally will comprise, in suitable means, distinct containers for each individual reagent and enzyme as well as for each primer or probe.

B. Immunologic Diagnosis

Antibodies of the present invention can be used in characterizing the STARS content of healthy and diseased tissues, through techniques such as ELISAs and Western blotting. This may provide a screen for the presence or absence of cardiomyopathy or serve as a predictor of heart disease.

The use of antibodies of the present invention in an ELISA assay is contemplated. For example, anti-STARS antibodies are immobilized onto a selected surface, preferably a surface exhibiting a protein affinity such as the wells of a polystyrene microtiter plate. After washing to remove incompletely adsorbed material, it is desirable to bind or coat the assay plate wells with a non-specific protein that is known to be antigenically neutral with regard to the test antisera such as bovine serum albumin (BSA), casein or solutions of powdered milk. This allows for blocking of non-specific adsorption sites on the immobilizing surface and thus reduces the background caused by non-specific binding of antigen onto the surface.

After binding of antibody to the well, coating with a non-reactive material to reduce background, and washing to remove unbound material, the immobilizing surface is contacted with the sample to be tested in a manner conducive to immune complex (antigen/antibody) formation.

Following formation of specific immunocomplexes between the test sample and the bound antibody, and subsequent washing, the occurrence and even amount of immunocomplex formation may be determined by subjecting same to a second antibody having specificity for STARS that differs from the first antibody. Appropriate conditions preferably include diluting the sample with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hr, at temperatures preferably on the order of about 25° C. to about 27° C. Following incubation, the antisera-contacted surface is washed so as to remove nonimmunocomplexed material. A preferred washing procedure includes washing with a solution such as PBS/Tween®, or borate buffer.

To provide a detecting means, the second antibody will preferably have an associated enzyme that will generate a color development upon incubating with an appropriate chromogenic substrate. Thus, for example, one will desire to contact and incubate the second antibody-bound surface with a urease or peroxidase-conjugated anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody.

The antibody compositions of the present invention will find great use in immunoblot or Western blot analysis. The antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. Immunologically-based detection methods for use in conjunction with Western blotting include enzymatically-, radiolabel-, or fluorescently-tagged secondary antibodies against the toxin moiety are considered to be of particular use in this regard.

C. Treating Defects in STARS Expression or Function

The present invention also involves, in another embodiment, the treatment of disease states related to the aberrant expression and/or function of STARS. In particular, it is envisioned that STARS activity plays a role in development of cardiac tissue. Thus, increasing levels of STARS, or compensating for mutations that reduce or eliminate the activity of STARS, are believed to provide therapeutic intervention in certain cardiomyopathies.

In addition, by increasing levels of STARS, it is possible that defects in other cardiac genes may be compensated for. STARS may be able to overcome deficiencies in the expression of other cardiac factors.

There also may be situations where one would want to inhibit STARS function or activity, for example, where overexpression or unregulated expression had resulted in cardiac dysfunction. In this case, one would take steps to interfere with or block the expression of STARS, or inhibit its activity.

D. Genetic Based Therapies

One of the therapeutic embodiments contemplated by the present inventors is intervention, at the molecular level, with the events involved in cardiac failure. Specifically, the present inventors intend to provide, to a cardiac cell, an expression construct capable of providing STARS to that cell. The lengthy discussion of expression vectors and the genetic elements employed therein is incorporated into this section by reference. Particularly preferred expression vectors are viral vectors such as adenovirus, adeno-associated virus, herpesvirus, vaccinia virus and retrovirus. Also preferred are liposomally-encapsulated expression vectors.

Those of skill in the art are aware of how to apply gene delivery to in vivo situations. For viral vectors, one generally will prepare a viral vector stock. Depending on the kind of virus and the titer attainable, one will deliver $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$ or $1 \times 10^{12}$ infectious particles to the patient. Similar figures may be extrapolated for liposomal or other non-viral formulations by comparing relative uptake efficiencies. Formulation as a pharmaceutically acceptable composition is discussed below. Various routes are contemplated, including local and systemic, but targeted provision to the heart is preferred. (See, for example Hammond, et al., supra, hereby incorporated by reference in its entirety.)

E. Combined Therapy

In many clinical situations, it is advisable to use a combination of distinct therapies. Thus, it is envisioned that, in addition to the therapies described above, one would also wish to provide to the patient more "standard" pharmaceutical cardiac therapies. Examples of standard therapies include so-called "beta blockers", anti-hypertensives, cardiotonics, anti-thrombotics, vasodilators, hormone antagonists, endothelin antagonists, cytokine inhibitors/blockers, calcium channel blockers, phosphodiesterase inhibitors and angiotensin type 2 antagonists. Also envisioned are combinations with pharmaceuticals identified according to the screening methods described herein.

Combinations may be achieved by contacting cardiac cells with a single composition or pharmacological formulation that includes both agents, or by contacting the cell with two distinct compositions or formulations, at the same time, wherein one composition includes the expression construct and the other includes the agent. Alternatively, the STARS therapy may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would contact the cell with both modalities within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either a STARS gene, protein or STARS agent, or the other agent will be desired. Various combinations may be employed, where STARS is "A" and the other agent is "B", as exemplified below:

A/B/A B/A/A B/B/A A/A/B B/A/A A/B/B B/B/B/A

B/B/A/B A/A/B/B A/B/A/B A/B/B/A B/B/A/A B/A/B/A

B/A/A/B B/B/B/A A/A/A/B B/A/A/A A/B/A/A A/A/B/A

A/B/B/B B/A/B/B B/B/A/B

Other combinations are contemplated as well.

F. Formulations and Routes for Administration to Patients

Where clinical applications are contemplated, it will be necessary to prepare pharmaceutical compositions—expression vectors, virus stocks and drugs—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal, intravascular or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with a variety of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

V. Drug Formulations and Routes for Administration to Patients

Where clinical applications are contemplated, pharmaceutical compositions will be prepared—e.g., expression vectors, virus stocks and drugs—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector or cells, dissolved or dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well know in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or cells of the compositions.

The active compositions of the present invention may include classic pharmaceutical preparations. Administration of these compositions according to the present invention may be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy syringability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

For oral administration the polypeptides of the present invention generally may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

VI. Methods of Making Transgenic Mice

A particular embodiment of the present invention provides transgenic animals that contain a selectable or screenable marker protein under the control of a STARS promoter. Transgenic animals expressing a STARS encoding nucleic acid under the control of an inducible or a constitutive promoter, recombinant cell lines derived from such animals, and transgenic embryos may be useful in determining the exact role that STARS plays in the development and differentiation of cardiomyocytes. Furthermore, this transgenic animal may provide an insight into heart development. The use of constitutively expressed STARS encoding nucleic acid provides a model for over- or unregulated expression. Also, transgenic animals which are "knocked out" for STARS, in one or both alleles, are contemplated.

In a general aspect, a transgenic animal is produced by the integration of a given transgene into the genome in a manner that permits the expression of the transgene. Methods for producing transgenic animals are generally described by Wagner and Hoppe (U.S. Pat. No. 4,873,191; which is incorporated herein by reference), Brinster et al. (1985); which is incorporated herein by reference in its entirety) and in Hogan et al. (1994).

Typically, a gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish.

DNA clones for microinjection can be prepared by any means known in the art. For example, DNA clones for microinjection can be cleaved with enzymes appropriate for removing the bacterial plasmid sequences, and the DNA fragments electrophoresed on 1% agarose gels in TBE buffer, using standard techniques. The DNA bands are visualized by staining with ethidium bromide, and the band containing the expression sequences is excised. The excised band is then placed in dialysis bags containing 0.3 M sodium acetate, pH 7.0. DNA is electroeluted into the dialysis bags, extracted with a 1:1 phenol:chloroform solution and precipitated by two volumes of ethanol. The DNA is redissolved in 1 ml of low salt buffer (0.2 M NaCl, 20 mM Tris, pH 7.4, and 1 mM EDTA) and purified on an Elutip-D™ column. The column is first primed with 3 ml of high salt buffer (1 M NaCl, 20 mM Tris, pH 7.4, and 1 mM EDTA) followed by washing with 5 ml of low salt buffer. The DNA solutions are passed through the column three times to bind DNA to the column matrix. After one wash with 3 ml of low salt buffer, the DNA is eluted with 0.4 ml high salt buffer and precipitated by two volumes of ethanol. DNA concentrations are measured by absorption at 260 nm in a UV spectrophotometer. For microinjection, DNA concentrations are adjusted to 31 g/ml in 5 mM Tris, pH 7.4 and 0.1 mM EDTA. Other methods for purification of DNA for microinjection are described in Hogan et al. (1986), in Palmiter et al. (1982); and in Sambrook et al. (1989).

In an exemplary microinjection procedure, female mice six weeks of age are induced to superovulate with a 5 IU injection (0.1 cc, ip) of pregnant mare serum gonadotropin (PMSG; Sigma) followed 48 hours later by a 5 IU injection (0.1 cc, ip) of human chorionic gonadotropin (hCG; Sigma). Females are placed with males immediately after hCG injection. Twenty-one hours after hCG injection, the mated females are sacrificed by $CO_2$ asphyxiation or cervical dislocation and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection. Embryos can be implanted at the two-cell stage.

Randomly cycling adult female mice are paired with vasectomized males. C57BL/6 or Swiss mice or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS (Dulbecco's phosphate buffered saline) and in the tip of a transfer pipet (about 10 to 12 embryos). The pipet tip is inserted into the infundibulum and the embryos transferred. After the transfer, the incision is closed by two sutures.

VII. Screening Assays

The present invention also contemplates the screening of compounds for various abilities to interact with and/or affect STARS expression or function. Particularly preferred compounds will be those useful in inhibiting or promoting the actions of STARS in regulating the development and differentiation of cardiomyocytes. In the screening assays of the present invention, the candidate substance may first be screened for basic biochemical activity—e.g., binding to a target molecule—and then tested for its ability to inhibit modulate activity, at the cellular, tissue or whole animal level.

A. Modulators and Assay Formats
  i) Assay Formats
The present invention provides methods of screening for modulators of STARS expression and actin binding activity. In one embodiment, the present invention is directed to a method of:

(a) providing an active STARS preparation;

(b) contacting said STARS preparation with a candidate modulator; and (c) measuring the actin binding activity of said STARS preparation, In yet another embodiment, the assay looks not at actin binding, but at STARS expression. Such methods would comprise, for example:

(a) providing a cell in which a STARS promoter directs the expression of a polypeptide;

(b) contacting said cell with a candidate modulator; and (c) measuring the effect of said candidate modulator on said polypeptide, the polypeptide may be STARS, or it may be an indicator protein.

ii) Candidate Substances

As used herein, the term "candidate substance" refers to any molecule that may potentially modulate STARS expression or function. The candidate substance may be a protein or fragment thereof, a small molecule inhibitor, or even a nucleic acid molecule. The term "candidate modulator" may be used in place of "candidate substance". It may prove to be the case that the most useful pharmacological compounds will be compounds that are structurally related to compounds which interact naturally with STARS. Creating and examining the action of such molecules is known as "rational drug design," and include making predictions relating to the structure of target molecules.

The goal of rational drug design is to produce structural analogs of biologically active polypeptides or target compounds. By creating such analogs, it is possible to fashion drugs which are more active or stable than the natural molecules, which have different susceptibility to alteration or which may affect the function of various other molecules. In one approach, one would generate a three-dimensional structure for a molecule like STARS, and then design a molecule for its ability to interact with STARS. Alternatively, one could design a partially functional fragment of STARS (binding, but no activity), thereby creating a competitive inhibitor. This could be accomplished by x-ray crystallography, computer modeling or by a combination of both approaches.

It also is possible to use antibodies to ascertain the structure of a target compound or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds or may be found as active combinations of known compounds which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be polypeptide, polynucleotide, small molecule inhibitors or any other compounds that may be designed through rational drug design STARSting from known inhibitors of hypertrophic response.

Other suitable inhibitors include antisense molecules, ribozymes, and antibodies (including single chain antibodies).

It will, of course, be understood that the screening methods of the present invention are useful in themselves notwithstanding the fact that effective candidates may not be found. The invention provides methods for screening for such candidates, not solely methods of finding them.

B. In Vitro Assays

A quick, inexpensive and easy assay to run is a binding assay. Binding of a molecule to a target may, in and of itself, be inhibitory, due to steric, allosteric or charge-charge interactions. This can be performed in solution or on a solid phase and can be utilized as a first round screen to rapidly eliminate certain compounds before moving into more sophisticated screening assays. In one embodiment of this kind, the screening of compounds that bind to a STARS molecule or fragment thereof is provided The target may be either free in solution, fixed to a support, expressed in or on the surface of a cell. Either the target or the compound may be labeled, thereby permitting determining of binding. In another embodiment, the assay may measure the inhibition of binding of a target to a natural or artificial substrate or binding partner (such as STARS). Competitive binding assays can be performed in which one of the agents (STARS for example) is labeled. Usually, the target will be the labeled species, decreasing the chance that the labeling will interfere with the binding moiety's function. One may measure the amount of free label versus bound label to determine binding or inhibition of binding.

A technique for high throughput screening of compounds is described in WO 84/03564. Large numbers of small peptide test compounds are synthesized on a solid substrate, such as plastic pins or some other surface. The peptide test compounds are reacted with, for example, STARS, and then washed fron the support to remove non-specifically bound protein. Bound polypeptide is detected by various methods.

Purified target, such as STARS, can be coated directly onto plates for use in the aforementioned drug screening techniques. However, non-neutralizing antibodies to the polypeptide can be used to immobilize the polypeptide to a solid phase. Also, fusion proteins containing a reactive region (preferably a terminal region) may be used to link an active region to a solid phase.

C. In Cyto Assays

Various cell lines that express STARS can be utilized for screening of candidate substances. For example, cells containing the STARS gene with an engineered indicator can be used to study various functional attributes of candidate compounds. In such assays, the compound would be formulated appropriately, given its biochemical nature, and contacted with a target cell.

Depending on the assay, culture may be required. As discussed above, the cells may then be examined by virtue of a number of different physiologic assays (growth, size, $Ca^{++}$ effects). Alternatively, molecular analysis may be performed in which the function of STARS and related pathways may be explored. This involves assays such as those for protein expression, enzyme function, substrate utilization, mRNA expression (including differential display of whole cell or polyA RNA) and others.

D. In Vivo Assays

The present invention particularly contemplates the use of various animal models. Transgenic animals may be created with constructs that permit STARS expression and activity to be controlled and monitored. The generation of these animals has been described elsewhere in this document.

Treatment of these animals with test compounds will involve the administration of the compound, in an appropriate form, to the animal. Administration will be by any route the could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply.

E. Production of Inhibitors

In an extension of any of the previously described screening assays, the present invention also provide for methods of producing inhibitors. The methods comprising any of the preceding screening steps followed by an additional step of "producing the candidate substance identified as a modulator of" the screened activity.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Differential cDNA cloning. For subtractive screening by representational difference analysis (RDA), hearts and the region of the embryo dorsal to the heart, including the neural fold and the first three somites were dissected from E8.25 mouse embryos. Total RNA was isolated from the heart and the dorsal embryonic region using TRIZOL (Gibco). mRNA was purified using a mRNA purification kit (Amersham Pharmacia) and converted into double-strand cDNA by the Superscript choice system for cDNA synthesis (Gibco). For subtraction screening between heart (Tester) and other embryonic parts (Driver), the RDA method described by Hubank and Schatz 1999 was used. Briefly, the cDNA from both tissues was digested with DpnII and ligated with an R-linker. (The annealed oligonucleotides were: R-Bgl-12: 5'-GATCTGCGGTGA-3' (SEQ ID:NO. 10) and R-Bgl-24: 5'-AGCACTCTCCAGCCTCTCACCGCA-3' (SEQ ID:NO. 11)) Using R-Bgl-24 as primer, cDNA was amplified by PCR and digested with DpnII again. cDNA from the heart was purified by gel extraction and ligated with a J-linker. (The annealed oligonucleotides were: J-Bgl-12: 5'-GATCT-GTTCATG-3' (SEQ ID:NO. 12) and J-Bgl-24: 5'-AC-CGACGTCGACTATCCATGAACA-3' (SEQ ID:NO. 13)). Tester ligated with J-linker and Driver cDNAs (ratio 1:100) were hybridized at 67° C. for 20 hrs. PCR reactions were then performed by primer J-Bgl-24 to yield a PCR product referred to as DPI (Differential product). DPI was digested with DpnII as a new tester and ligated with N-linker (The annealed oligonucleotides were: N-Bgl-12: 5'-GATCTTTC-CATCG-3' (SEQ ID:NO. 14) and N Bgl-24: 5'-AG-GCAACTGTGCTATCCGAGGGAA-3' (SEQ ID:NO. 15)). N-linker-ligated DPI was hybridized with Driver (ratio 1:800) and amplified by PCR two times using N-oligonucleotides as primer. Linkers for tester were replaced with J-oligonucleotides in the third round, and N-oligonucleotides in the fourth round of hybridization. The final PCR products, referred to as DPIV, were cloned into the TA cloning vector (pGEMT easy, Promega) and inserted DPIV fragments were amplified by PCR using N-Bgl-24 as primers to make two identical dot blots. One dot blot was hybridized with tester probe, and the other was hybridized with driver probe to confirm the differential expression of DPIV fragments.

To obtain a full-length STARS cDNA, an E10.5 mouse heart cDNA library (Stratagene) was screened using a 342 bp cDNA fragment isolated by RDA. The longest positive clone contained a 375-amino acid open reading frame, without a stop codon 5' of the first methionine in the sequence. To obtain further 5' sequence, adult mouse heart and skeletal muscle cDNA libraries (Clontech) were screened with a 400 bp cDNA fragment from the 5' end of the longest cDNA as a probe. 5'-RACE was also performed using the SMART 5'-RACE kit (Clontech) and the RLM first choice 5'-RACE kit (Ambion) following the manufacturer's instructions. 5'-RACE was performed with mRNA from human skeletal muscle (Clontech) and from mouse heart and skeletal muscle. There were no stop codons upstream of the first methionine.

Northern Blot Analysis. Northern blot analysis was performed using mouse and human multiple tissue Northern blots (Clontech) or total RNA isolated from C2 skeletal muscle cells and mouse hearts by the TRIZOL reagent.

C2 skeletal muscle cells were maintained in DMEM with 20% FBS (growth medium) and were induced to differentiate by transfer to medium with 2% horse serum (differentiation medium). Transgenic mice harboring an α-MHC-calcineurin transgene have been described previously (Molkentin et al., 1998). $^{32}$P-labeled probes were prepared from a full-length mouse STARS cDNA and a partial human cDNA. Glyceraldehyde-3-phosphate dehydrogenase (GAPDH) transcripts were measured as a control. Hybridizations were performed in Quick Hyb (Clontech).

In situ Hybridization. RNA probes corresponding to the sense and the anti-sense strands of the STARS cDNA were prepared. In situ hybridization was performed on sagittal sections of mouse embryos, as described (Benjamin et al., 1997).

STARS Expression Plasmids. STARS expression constructs were generated using the pcDNA3.1 mammalian expression vector (Invitrogen) which was modified to contain an amino-terminal Myc-tag. Constitutively active RhoA (L63) and C3 transferase in Prk5 were generously provided by Dr. Alan Hall (University College, London, United Kingdom). The SM22-luciferase reporter 1343 bp promoter has been previously described (Li et al., 1995). The smooth muscle α actin-luciferase reporter contained the 4 kb promoter region ligated into the pBL3basic vector (Promega). The ANF reporter contained the 638 bp promoter region (a generous gift from Dr. Mona Nemer, Universite de Montreal, Montreal, Quebec, Canada). The 4xcfos reporter contained four tandem copies of the cfos CArG box with flanking sequences, as described (Chang et al., 2001). CMV-lacZ (Promega) was used as an internal control for transfection efficiency.

Transient Transfections, Reporter Assays and Immunofluorescence Microscopy. COS cells were maintained in DMEM with 10% FBS. Eighteen hours after plating, the medium was changed to serum-free medium and transfections were performed at 50% confluency using FuGENE reagent-6 (Roche Molecular Biochemicals) following manufacturer's instructions. Each transfection used 0.15 µg of plasmid DNA for the reporter assays, and 0.5–1.0 µg immunohistochemistry. Cytochalasin D 2 µM (Sigma-Aldrich), and Y-27632 75 µM (Tocris) were added directly just after transfection. Latrunculin B 0.5 µM (dissolved in 10% ethanol, Calbiochem) was added 12 hr after transfection and 10% ethanol (final concentration 0.01%) was added to control wells. Cells were harvested 36 hr after transfection and their luciferase and β-galactosidase activity were measured.

For measuring immunofluorescence, cells were rinsed with PBS and fixed in 4% paraformaldehyde for 10 min on ice. After rinsing with PBS, COS cells were incubated in 0.1% Triton X-100 in PBS for 5 min on ice. For rat neonatal cardiomyocytes, 1% Triton X-100 in PBS was used. Cells were blocked for 20 min at room temperature in 0.5% BSA in PBS for COS cells and in 1% BSA plus 3% goat serum in PBS for rat cardiomyocytes. Then, cells were incubated with first antibody diluted in 0.5% BSA in PBS for 30–60 min at room temperature or overnight at 4° C. Anti c-myc monoclonal antibody 9E10 (Santa Cruz) was used at a 1:200 dilution. Other antibodies were anti α-actinin monoclonal antibody (1:400; Sigma-Aldrich), α-tubulin antibody (1:2000; Sigma-Aldrich) and anti-vimentin antibody (1:500; Sigma-Aldrich). Secondary antibodies were anti mouse/rabbit IgG FITC or Texas red (Vector) used at a 1:200 dilution incubated with or without Phalloidin-TRITC (1:500; Sigma Aldrich).

Western Blot and Co-immunoprecipitation Assay. Immunoprecipitation and western blot analysis was performed as described previously (Lu et al., 2000). For immunoprecipitation, cells were incubated with 1 µg anti c-myc polyclonal antibody A14 (Santa Cruz). Western blots were performed with anti-actin monoclonal antibody C4 (1:100; Roche Molecular Biochemicals) or anti c-myc monoclonal antibody 9E10 (1:1000; Santa Cruse) followed by incubation with secondary antibody HRP-conjugated anti mouse-IgG (Santa Cruse, Vector). To detect signals, blots were incubated with ECL (Santa Cruz) for 1 min, and exposed to film (Eastman Kodak Co).

Adenoviral transduction and infection to cardiomyocytes. The full length STARS cDNA including a Kozak consensus sequence was ligated into pACCMViresAdeno (a kind gift from Dr. Robert Gerard) to generate adenovirus expressing STARS and GFP protein by Cre-lox recombination (Aoki et al., 1999). Neonatal rat cardiomyocytes were isolated as described previously (Nicol et al., 2001). After 36 hr, cardiomyocytes were infected for 2 hr with STARS- and GFP-expressing adenovirus at a multiplicity of infection of 100. After infection, cells were cultured in non-serum medium (DMEM:Medium199 4:1, penicillin/streptomycin).

GST-STARS purification and sedimentation assays. A cDNA encoding the full-length STARS open reading frame was cloned in-frame into vector pGEXKG (Guan and Dixon, 1991). BL21-DE3 cells containing the GST-fusion expression plasmid were grown to an optical density of 0.5 and induced with 1 mM IPTG for 3 hr at 370 C. GST-STARS was purified by GST-affinity chromatography using standard techniques. Purified actin and actinin were purchased from Cytoskeleton, Inc. BSA was purchased from Sigma-Aldrich. Actin sedimentation assays were performed as recommended by Cytoskeleton, Inc. Supernatants and pellets were analyzed by SDS-PAGE and coomassie blue staining.

Antibody production. To raise an anti-STARS antibody, the full length cDNA was cloned in frame with glutathione-S-transferase in pGEXKG (Guan and Dixon, 1991), which was tranformed into BL21 DE3 codon plus (Stratagene). Protein induction and purification was performed following standard protocol. Rabbit immunization was conducted by Cocalico Biologicals. For immunostaining and western blots, IgG was purified from antisera with protein A sepharose beads (Zymed).

Example 2

Results

Figure 1:
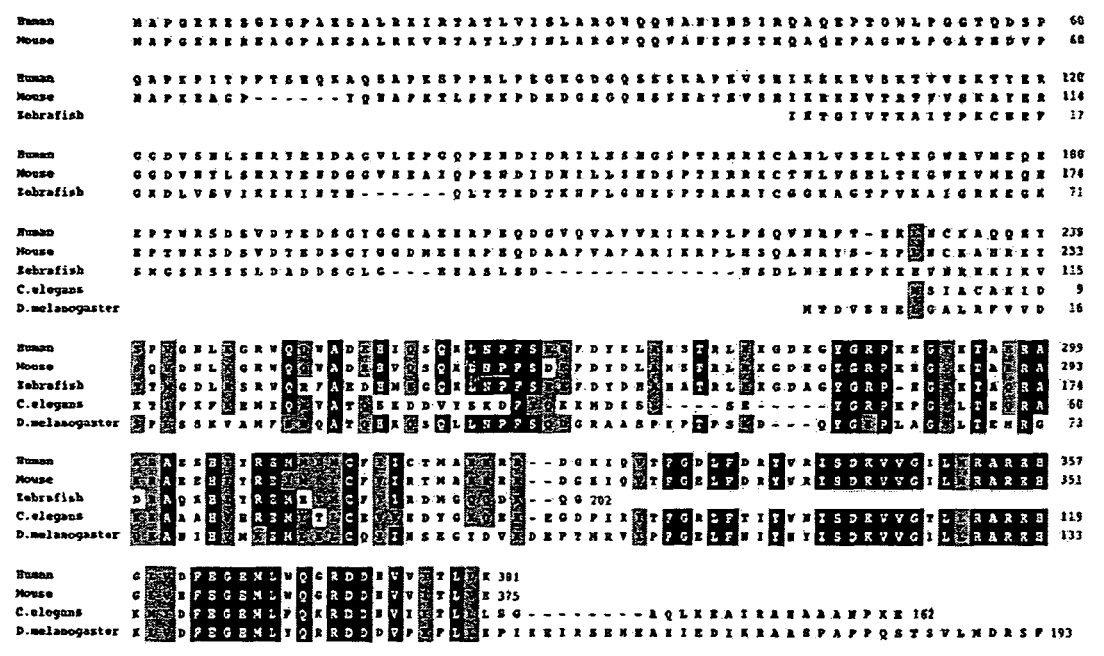

Evolutionary conservation of STARS proteins. A differential cDNA screen was performed for novel genes expressed in the mouse heart tube at E8.25, but not in other regions of the E8.25 embryo. Positive clones representing heart tube-specific genes were used for whole-mount in situ hybridization to confirm their cardiac-specificity. One of the cardiac-specific cDNAs isolated in the screen encoded a novel 375-amino acid protein that is referred to as striated muscle activator of Rho Signalin (STARS), because it is expressed specifically in striated muscle where it binds and bundles actin (see below). The predicted open reading frame of STARS did not contain recognizable protein motifs. Database searches for related genes revealed an apparent human ortholog encoded by a gene located on chromosome 8q23. A partial cDNA encoding a STARS-like protein was also identified in the zebrafish EST database (FIG. 1). No other related genes were identified in searches of the mouse and human genome sequences, indicating that STARS is a single gene without related family members. Genomic sequences with the potential to encode proteins with high homology to the carboxy-terminal 142 amino acids of STARS were also identifed in *C. elegans* (F36F2.1, T04A8.4) and *Drosophila melanogaster* (FIG. 1).

STARS is expressed specifically in cardiac and skeletal muscle. Consistent with the cDNA subtraction scheme, STARS transcripts were detected by in situ hybridization only in the primitive heart tube at E8.75 (FIG. 2A). Thereafter, STARS expression was maintained in the heart and was also detected in skeletal muscle after E10.5 (data not shown). Northern analysis of adult tissues revealed three STARS transcripts in mouse heart and skeletal muscle and two transcripts in these human tissues (FIG. 2B). Sequencing of multiple independent cDNAs revealed only a single open reading frame with no evidence for alternative splicing within the protein coding region. Therefore, it is believed that the multiple transcripts reflect the presence of different 3'-untranslated sequences.

In the C2 skeletal muscle cell line, STARS expression was undetectable in proliferating myoblasts, but was upregulated after three days in differentiation medium, following the formation of myotubes (FIG. 2C). Thus, STARS appears to be a relatively late marker for skeletal muscle differentiation.

STARS was examined to determine if it was regulated during hypertrophic growth of the heart, which is associated with up-regulation of a specific set of cardiac genes. Expression of activated calcineurin in the heart results in profound hypertrophy that ultimately progresses to dilated cardiomyopathy (Molkentin et al., 1998). STARS expression was upregulated dramatically in calcineurin transgenic mice at 3 months of age, when hearts showed extreme concentric hypertrophy without obvious left ventricular failure (FIG. 2D). By 6 months of age, when hearts from these mice had dilated and were in late stages of failure, STARS expression was further up-regulated. Cardiac expression of STARS was also up-regulated following banding of the thoracic aorta, which results in hypertrophy due to pressure-overload.

Figure 3:
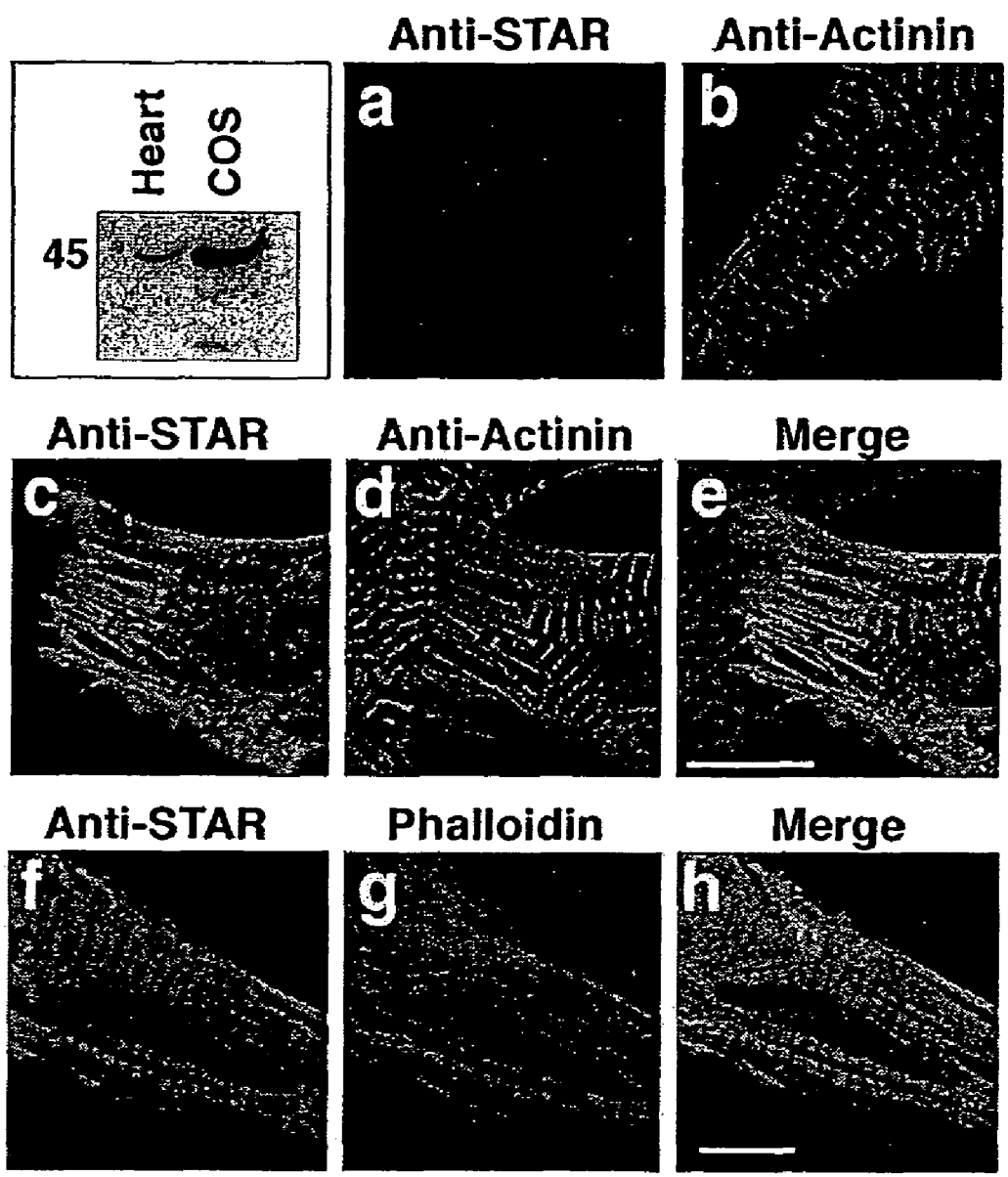
FIG. 3—Identification of STARS as a sarcomeric protein.

STARS localization in cardiomyocytes. Western blot analysis of adult mouse heart extracts an anti-STARS antibody revealed a single protein species of 45 kD, similar to the predicted size of STARS (FIG. 3A). This band comigrated with a Myc-tagged STARS protein expressed in transfected COS cells.

To determine the subcellular distribution of STARS, rat primary cardiomyocytes were immunostained with the STARS antibody (FIG. 3B, a&d). STARS staining showed a periodicity reminiscent of sarcomeric localization. The sarcomeric localization of STARS abuts the Z-line on both sides as demonstrated by a partial overlap with α-actinin (FIG. 3B, b&c, e&f). This periodicity demonstrates that STARS is localized to the I-band of the sarcomere. In addition to I-band localization, a portion of STARS localizes to sarcomeric structures between Z-lines (FIG. 3B, c&f). A schematic of STARS localization is depicted in FIG. 3C. Together, these results indicated that STARS functions as a muscle-specific actin-binding protein.

Figure 4:
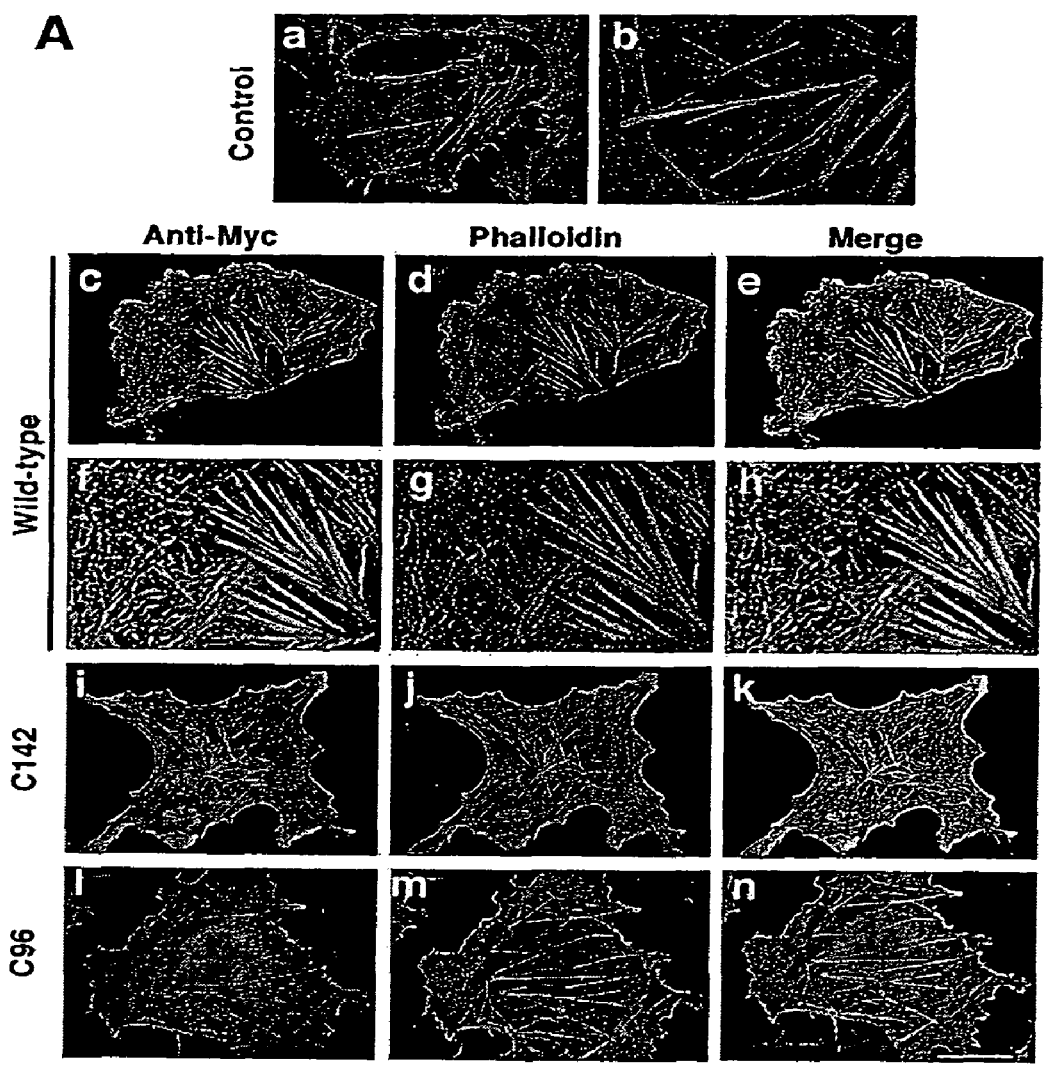
FIG. 4—Deletion mapping of the actin-binding domain of STARS.
Figure 4:
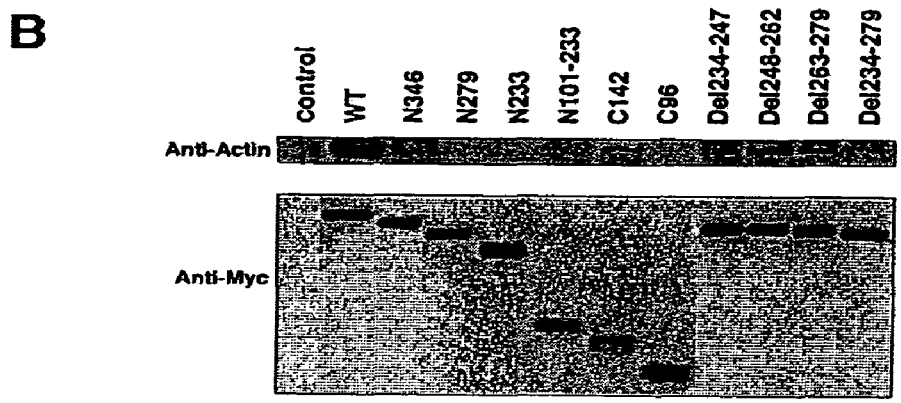

Mapping the F-actin binding domain of STARS. To further investigate the function of STARS, the subcellular localization of a Myc-tagged STARS protein in transiently transfected COS cells was examined. STARS strongly colocalized with F-actin in stress fibers and membrane ruffles, which were also stained by Phalloidin-TRITC (FIG. 4A; c, d and e). STARS-transfected cells also exhibited an increased number of actin stress fibers and especially prominent thick fibers, indicating that ectopic STARS expression induced stress fiber formation and bundling (FIG. 4A; f, g and h). Other structural proteins, including tubulin, vimentin, and keratin did not colocalize with STARS (data not shown).

To map the region of STARS that mediated the association with F-actin, immunofluorescence was performed with a series of STARS deletion mutants in transfected COS cells. Deletion mutants lacking residues from the carboxy-terminus into the conserved region of STARS (mutants N346, N323, N304, N279, N233, N100, and N101–233), and a deletion mutant within the conserved region (C96), did not affect the association with F-actin, but abolished the ability of STARS to bundle actin stress fibers (FIG. 4A; l, m, n and 5, and data not shown). In contrast to C96, a deletion mutant that encoded only the conserved region (C 142) not only associated with F-actin, but also increased stress fibers, although bundled stress fibers were not as frequent as seen with the wild-type protein (FIG. 4A; i, j and, k). Deletion mutant Del234–279 was able to associate with F-actin, but lost the ability to bundle actin fibers. Smaller sub-deletions of this region retained the ability to bundle actin, indicating that the amino acid residues responsible for this function were distributed across residues 234–279. These findings indicated that the conserved carboxy-terminal domain of STARS was responsible for actin-bundling and that there were multiple, non-overlapping regions of the protein capable of weakly associating with F-actin in vivo.

Co-immunoprecipitation of STARS with actin. The actin binding function of STARS was further investigated by co-immunoprecipitation experiments in COS cells transiently transfected with Myc-tagged proteins. As shown in FIG. 4B, the wild-type protein and the conserved carboxy terminal region (C142) co-immunoprecipitated with actin. Deletions that removed the carboxy-terminal portion of the conserved region did not bind actin (mutants N346, N323, N304, N279, N233, N100, and N101–233), whereas small internal deletions within the conserved region (Del 234–247, Del 248–262, Del 263–279) retained weak actin-binding activity in this assay. The larger deletion mutant in this region (Del 234–279) failed to co-immunoprecipitate with actin. These results revealed a direct correlation between actin binding/bundling activity in vivo and co-immunoprecipitation of STARS with actin (FIG. 5).

Figure 6:
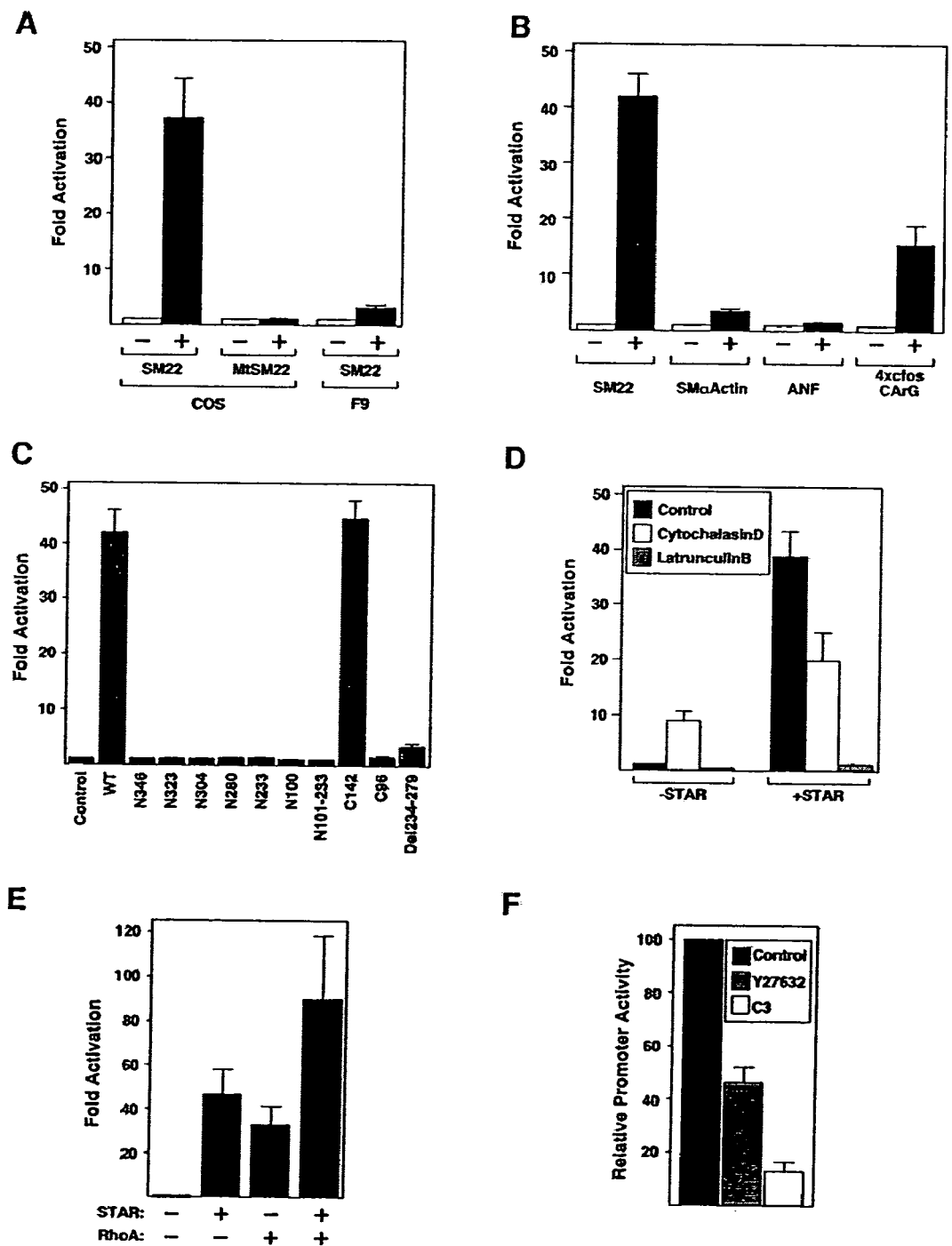
FIG. 6—STARS stimulates SRF activity through a Rho-dependent mechanism.

STARS stimulates SRF-dependent transcription via actin polymerization. Recent studies have shown that stabilization of the actin cytoskeleton stimulates the transcriptional activity of SRF (Mack et al., 2001), but the proteins involved in this phenomenon have not been identified. To examine whether STARS might participate in a signaling pathway between the cytoskeleton and the nucleus, the promoter of the SM22 gene, which is regulated by SRF in muscle cells (Li et al., 1997; Kim et al., 1997), was tested to determine if it was responsive to STARS. Remarkably, STARS stimulated the expression of an SM22 luciferase reporter by 40-fold in transiently transfected COS cells (FIG. 6A). Mutation of the CArG boxes in the SM22 promoter abolished responsiveness to STARS, demonstrating the involvement of SRF in this response. In F9 cells, which have low endogenous SRF expression (Li et al., 1997), STARS had a minimal effect on the SM22 promoter (FIG. 6A), further indicating that the effects of STARS were mediated by SRF. Stimulation of SRF activity is not a general property of actin-binding proteins, as α-actinin has no effect on SRF activity (data not shown). STARS also weakly stimulated the α-smooth muscle actin promoter, which is regulated by SRF (Mack and Owens, 1999), and it activated an E1b promoter linked to four tandem copies of the CArG box and flanking sequences from the c-fos promoter (FIG. 6B). However, it did not stimulate the atrial natriureticfactor (ANF) promoter (FIG. 6B) which is also regulated by SRF (Hines et al., 1999). It also did not activate the cytomegalovirus promoter (data not shown).

Figure 5:
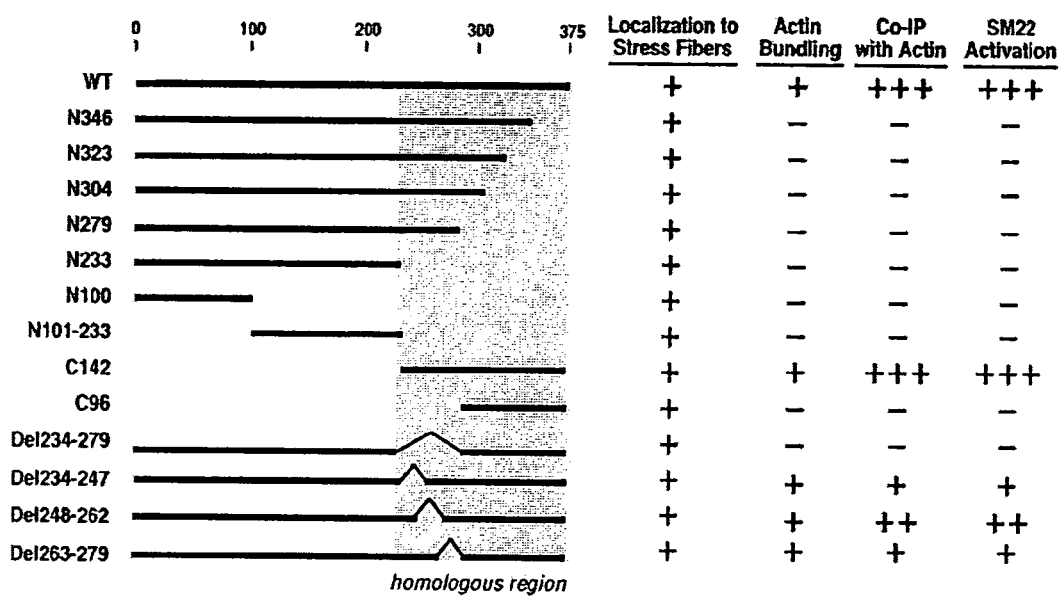
FIG. 5—Summary of STARS deletion mutants. STARS (wt) and all deletion mutants associates with actin stress fibers in immunocytochemistry, Wild type STARS and deletion mutants (C142, Del234–247, Del248–262 and Del263–279) have an ability to induce actin bundles and activate SRF transcription.

A summary of the properties of STARS deletion mutants is shown in FIG. 5. Comparison of the complete set of STARS deletion mutants showed a direct correlation between the ability to bind actin and bundle actin fibers and to stimulate SM22 transcription (FIG. 6C). The conserved carboxy terminal region of STARS was necessary and sufficient to stimulate SRF activity, as demonstrated by the finding that mutant C142 was as effective as the full-length protein in activating SM22-luciferase.

Effects of actin depolymerizing agents on SM22 promoter activation by STARS. To examine whether STARS stimulates SRF activity via its effects on actin dynamics, COS cells were treated with cytochalasin D (CD), which prevents actin polymerization (Sampath and Pollard, 1991), and latrunculin B (LB), which sequesters monomeric actin (Morton et al., 2000). In STARS-transfected cells, only short fragments of disrupted stress fibers were observed in the presence of 2 µM CD or 0.5 µM LB (data not shown). CD itself increased SM22 promoter activity by 8-fold, consistent with previoius results (Sotiropoulos et al., 1999; Mack et al., 2001). STARS increased promoter activity 18-fold in the presence of CD. In contrast, LB treatment abolished SM22-luciferase activity even in cells transfected with STARS (FIG. 6D). These findings indicated that STARS might stimulate SRF activity by reducing the cellular pool of G-actin as a result of its ability to enhance actin polymerization. The opposing effects of CD and LB are likely to reflect their differential effects on the pool of G-actin; whereas CD dimerizes G-actin (Goddette and Frieden, 1986), LB sequesters G-actin (Morton et al., 2000).

Involvement of RhoA in SRF activation by STARS. In light of the ability of RhoA to stimulate SRF activity by promoting actin polymerization (Mack et al., 2001; Sotiropoulos et al., 1999), the effects of a constitutively active RhoA mutant (L63) and STARS on SM22 promoter activity were compared. As shown in FIG. 6E, STARS and RhoA L63 activated the SM22 promoter to comparable levels and together stimulated activity to higher levels.

Rho signaling is inhibited by the Rho kinase inhibitor Y-27632, which inhibits stress fiber formation (Maekawa et al., 1999), and C3 transferase, which specifically ADP-ribosylates RhoA (Nemoto et al., 1992). Treatment of COS cells with Y-27632 (75 µM) or transfection with a C3 expression plasmid reduced the stimulatory activity of STARS on the SM22 promoter by 55% and 88%, respectively (FIG. 6F). Together, these results indicate that STARS requires a basal level of RhoA activity to enhance SRF activity.

Example 3

Discussion

Stimulation of SRF-dependent transcription by STARS. Previous studies indicated that G-actin suppresses the activity of SRF (Sotiropoulos et al., 1999), and several observations indicate that STARS activates SRF by relieving this repressive influence. For example, agents such as latrunculin B, which sequesters G-actin monomers (Morton et al., 2000), inhibit the activity of STARS. The ability of STARS to stimulate actin polymerization and cross-linking would also be expected to reduce the G-actin pool. It is important to point out that the stimulation of actin polymerization per se is not sufficient to account for the effects of STARS on SRF activity, because STARS is able to increase SRF activity in the presence of cytochalasin D, which prevents actin polymerization and also stimulates SRF (Sotiropoulos et al., 1999; Mack et al., 2001).

Figure 7:
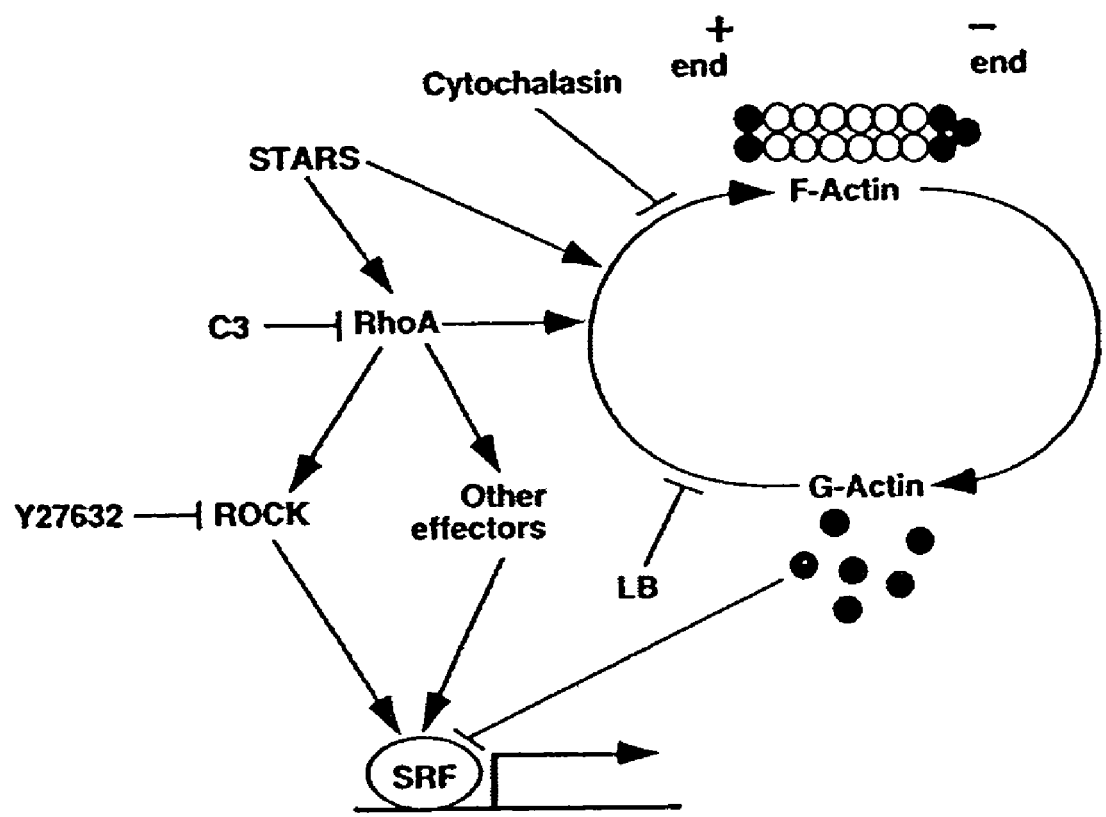
FIG. 7—A model for the involvement of STARS in actin dynamics and signaling to SRF. The distribution of actin between the polymerized (F actin) and monomeri (G actin) states is determined by actin treadmilling. Actin monomers are added to the plus end and are removed from the minus end of actin filaments. STARS promotes the formation of F actin and activates Rho, which also promotes actin polymerization. Rho activates ROCK and other effectors leading to the stimulation of SRF activity.

A working model of a potential mechanism of action of STARS within the context of the regulation of actin dynamics is shown in FIG. 7. Actin treadmilling determines the relative distribution of the monomeric G-actin and polymerized F-actin states. Previous studies suggested that G-actin suppresses the activity of SRF (Sotiropoulos et al., 1999). The results suggest that STARS activates SRF by relieving this repressive influence, as a result of its ability to stimulate actin polymerization and thereby reduce the G-actin pool. Such a mechanism would account for the ability of latrunculin B, which sequesters G-actin monomers (Morton et al., 2000), to interfere with the activity of STARS.

While polymerization of actin by STARS appears to be coupled to SRF activation, stimulation of actin polymerization per se is not sufficient to account for the effects of STARS on SRF activity, because STARS is able to increase SRF activity in the presence of cytochalasin D, which prevents actin polymerization by binding to the plus-end of F-actin, where it blocks further addition of actin subunits. Cytochalasin D also stimulates SRF activity alone, presumably by reducing the level of free G-actin monomers (Sotiropoulos et al., 1999; Mack et al., 2001).

In principle, G-actin could inhibit SRF directly or it could sequester cofactors required for SRF activation (Sotiropoulos et al., 1999). In light of the actin-binding properties of STARS, it may stimulate SRF by acting as a sink to sequester G-actin and thereby relieve repression on SRF. G-actin has been shown to shuttle to the nucleus (Wada et al., 1998) and also to be contained within the SWI-SNF chromatin remodeling complex (Van Etten et al., 1994; Zhao et al., 1998; Rando et al., 2000). Whether STARS might alter the incorporation of actin into this complex is a possiblity. Since STARS is localized to the cytoplasm, it may not stimulate transcription by associating directly with SRF or other transcriptional components.

SRF activates muscle-specific transcription by recruiting myogenic transcription factors, such as GATA4, Nkx2.5 and myocardin (Chen and Schwartz, 1996; Belaguli et al., 2000; Morin et al., 2001; Wang et al., 2001). Although STARS is a muscle-specific protein, its ability to stimulate SRF activity in nonmuscle cells indicates that it does not require these myogenic transcription factors for activity. STARS is upregulated after the onset of myocyte differentiation and may act as an actin cross-linker during myofibrillogenesis, thereby further enhancing SRF activity in differentiated muscle cells and reinforcing the expression of SRF-dependent sarcomeric genes.

Regulation of STARS activity, SRF activity and muscle gene expression by Rho signaling. Rho signaling promotes the formation of F-actin and could deplete the G-actin pool. Sotiropoulus concluded that the effects of Rho on SRF are secondary to its effects on the cytoskeleton and are mediated by a decrease in G-actin as a result of actin polymerization (Sotiropoulos et al., 1999). Stimulation of SRF activity by STARS appears to require at least a basal level of RhoA signaling, as demonstrated by the ability of the Rho kinase inhibitor Y-27632 and C3 transferase to diminish SRF activation by STARS. Conversely, constitutively active RhoA enhances the stimulatory effect of STARS on SRF activity. The fact that Y-27632 only partially inhibits STARS activity may indicate the involvement of other Rho effectors in the mechanism for STARS action. It is also possible that these inhibitors interfere with the SRF-activating properties of STARS through an indirect mechanism due to changes in cell morphology.

Rho signaling plays an important role in muscle gene expression. Previous studies have shown that RhoA activates the skeletal muscle α-actin promoter, which is SRF-dependent (Wei et al., 1998; Wei et al., 2001). Activation of RhoA by Gq-coupled receptor agonists also induces premyofibrils, myofibril organization and ANF expression in primary cardiomyocytes (Thorbum et al., 1997; Aoki et al., 1998; Hoshijima et al., 1998). STARS could not activate the ANF promoter, although RhoA can upregulate ANF expression in cardiomyocytes. This indicates that STARS does not activate Rho directly. Of course, stimulation of SRF activity by Rho does not require STARS, since Rho can activate SRF in nonmuscle cells in which STARS is not expressed. In contrast, STARS requires basal Rho activity to activate SRF, because the Rho inhibitor C3 and the Rho kinase inhibitor Y27632 decreased SM22 promoter activity significantly, indicating that STARS might have cross-talk or interaction with some effector molecules of Rho and to Rho kinase. Taken together, the results indicate that stimulation of SRF activity by STARS activation is not mediated by the same effector-molecules that mediate ANF promoter activation by RhoA in cardiomyocytes.

Linking the cytoskeleton and the sarcomere to muscle gene expression. STARS expression is maintained in adult cardiac and skeletal muscle and is dramatically up-regulated during hypertrophic growth of the heart in response to calcineurin activation and pressure-overload, which is associated with calcineurin activation (Leinwand, 2001). Sarcomere organization is a hallmark of cardiac hypertrophy. During hypertrophic growth of cardiomyocytes, STARS might organize new myofibrils, whereas extreme overexpression might result in disorganization of actin bundles with resulting cardiac dysfunction as observed in failing hearts.

The integrity of the cytoskeleton and sarcomere has a profound influence on gene expression and growth of muscle cells. The actin bundling/binding and SRF-activating properties of STARS provide a potential link between myocyte structure and the program for muscle gene expression.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

IX. REFERENCES

The following references, to the extent that they provide exemplary procedural or other details supplementary to those set forth herein, are specifically incorporated herein by reference.

U.S. Pat. No. 4,554,101
U.S. Pat. No. 5,354,855
U.S. Pat. No. 5,792,453
U.S. Pat. No. 6,100,242
U.S. Pat. No. 4,196,265
U.S. Pat. No. 4,683,195
U.S. Pat. No. 4,683,202
U.S. Pat. No. 4,800,159
U.S. Pat. No. 4,883,750
U.S. Pat. No. 5,279,721
U.S. Pat. No. 4,873,191

Angel, Bauman, Stein, Dellus, Rahmsdorf, and Herrlich, "12-0-tetradecanoyl-phorbol-13-acetate Induction of the Human Collagenase Gene is Mediated by an Inducible Enhancer Element Located in the 5' Flanking Region," Mol. Cell. Biol., 7:2256, 1987a.

Angel, Imagawa, Chiu, Stein, Imbra, Rahmsdorf, Jonat, Herrlich, and Karin, "Phorbol Ester-Inducible Genes Contain a Common cis Element Recognized by a TPA-Modulated Trans-acting Factor," Cell, 49:729, 1987b Aoki, H., Izumo, S. and Sadoshima, J., Angiotensin II activates RhoA in cardiac myocytes: a critical role of RhoA in angiotensin II-induced premyofibril formation. Circ. Res., 82, 666–76, 1998.

Aoki, K., Barker, C., Danthinne, X., Imperiale, M. J. and Nabel, G. J., Efficient generation of recombinant adenoviral vectors by Cre-lox recombination in vitro. Molecular Medicine, 5, 224–31, 1999.

Atchison and Perry, "Tandem Kappa Immunoglobulin Promoters are Equally Active in the Presence of the Kappa Enhancer: Implications for Model of Enhancer Function," Cell, 46:253, 1986.

Atchison and Perry, "The Role of the Kappa Enhancer and its Binding Factor NF-kappa B in the Developmental Regulation of Kappa Gene Transcription," Cell, 48:121, 1987.

Baichwal and Sugden, "Vectors for gene transfer derived from animal DNA viruses: Transient and stable expression of transferred genes", In: Gene Transfer, Kucherlapati R, ed., New York, Plenum Press, pp. 117–148, 1986.

Banerji, Olson, and Schaffner, "A lymphocyte-specific cellular enhancer is located downstream of the joining region in immunoglobulin heavy-chain genes," Cell, 35:729, 1983.

Bang, M. L., Mudry, R. E., McElhinny, A. S., Trombitas, K., Geach, A. J., Yamasaki, R., Sorimachi, H., Granzier, H., Gregorio, C. C. and Labeit, S., Myopalladin, a novel 145-kilodalton sarcomeric protein with multiple roles in Z-disc and I-band protein assemblies. J. Cell Biol., 153, 413–27, 2001.

Barany and Merrifield, The Peptides, Gross and Meienhofer, eds., Academic Press, New York, pp. 1–284, 1979.

Barnes, Cheng, Dawson, Menick, "Cloning of cardiac, kidney, and brain promoters of the feline ncx1 gene," J. Biol. Chem., 272(17):11510–7, 1997.

Baughman, K., Cardiology Clinics, 13: 27–34, 1995.

Benjamin, I. J., Shelton, J., Garry, D. J. and Richardson, J. A., Temporospatial expression of the small HSP/alpha B-crystallin in cardiac and skeletal muscle during mouse development. Dev. Dyn., 208, 75–84, 1997.

Benvenisty and Neshif, "Direction introduction of genes into rats and expression of the genes", Proc. Nat'l Acad. Sci. USA, 83:9551–9555, 1986.

Berkhout et al., "Tat trans-activates the human immunodeficiency virus through a nascent RNA target," Cell, 59:273, 1989.

Bhavsar, Brand, Yacoub, Barton, "Isolation and characterization of the human cardiac troponin I gene (TNNI3)," Genomics, 35(1):11–23, 1996.

Biben and Harvey, "Homeodomain factor Nkx2–5 controls left/right asymmetric expression of bHLH bene eHand during murine heart development," Genes Dev., 11:1357–1369, 1997.

Black and Olson, "Transcriptional control of muscle development by myocyte enhancer factor-2 (MEF2) proteins," Annual Rev. Cell Dev. Biol., 14:167–196, 1998.

Blanar, Baldwin, Flavell, Sharp, "A gamma-interferon-induced factor that binds the interferon response sequence of the MHC class I gene, H-2 Kb," EMBO J, 8(4): 1139–44, 1989.

Bodine and Ley, "An enhancer element lies 3' to the human A gamma globin gene," EMBO J., 6:2997, 1987.

Boshart, Weber, Jahn, Dorsch-Hasler, Fleckenstein, and Schaffner, "A very strong enhancer is located upstream of an immediate early gene of human cytomegalovirus," *Cell*, 41:521, 1985.

Bosze, Thiesen, and Charnay, "A transcriptional enhancer with specificity for erythroid cells is located in the long terminal repeat of the friend murine leukemia virus," *EMBO J.*, 5:1615, 1986.

Bour, O'Brien, Lockwood, Goldstein, Bodmer, Taghert, Abmayr, Nguyen, "*Drosophila* MEF2, a transcription factor that is essential for myogenesis," *Gene Devel.*, 9:730–741, 1995.

Braddock, Chambers, Wilson, Esnouf, Adams, Kingsman, and Kingsman, "HIV-1 Tat activates presynthesized RNA in the nucleus," *Cell*, 58:269, 1989.

Braunwald, E. (ed), In: "Heart Disease," W. B. Saunders, Philadelphia, page 426, 1988.

Brinster, Chen, Trumbauer, Yagle, Palmiter, "Factors affecting the efficiency of introducing foreign DNA into mice by microinjecting eggs," *Proc. Nat'l Acad. Sci. USA*, 82(13):4438–4442, 1985.

Bulla and Siddiqui, "The hepatitis B virus enhancer modulates transcription of the hepatitis B virus surface-antigen gene from an internal location," *J. Virol.*, 62:1437, 1986.

Burridge, K. and Chrzanowska-Wodnicka, M., Focal adhesions, contractility, and signaling. *Annu. Rev. Cell. Dev. Biol.*, 12, 463–518, 1996.

Calderwood, D. A., Shattil, S. J. and Ginsberg, M. H., Integrins and actin filaments: reciprocal regulation of cell adhesion and signaling. *J. Biol. Chem.*, 275, 22607–10, 2000.

Campbell and Villarreal, "Functional analysis of the individual enhancer core sequences of polyoma virus: cell-specific uncoupling of DNA replication from transcription," *Mol. Cell. Biol.*, 8:1993, 1988.

Campbell, In: *Monoclonal Antibody Technology, Laboratory Techniques in Biochemistry and Molecular Biology*, Vol. 13, Burden and Von Knippenberg, Eds. pp. 75–83, Amsterdam, Elseview, 1984.

Campere and Tilghman, "Postnatal repression of the α-fetoprotein gene is enhancer independent," *Genes and Dev.*, 3:537, 1989.

Campo, Spandidos, Lang, Wilkie, "Transcriptional control signals in the genome of bovine papilloma virus type 1," *Nature*, 303:77, 1983.

Capaldi, Bell, Branchek, "Changes in order of migration of polypeptides in complex III and cytochrome C oxidase under different conditions of SDS polyacrylamide gel electrophoresis," *Biochem. Biophys. Res. Comm.*, 76:425–433, 1977.

Celander and Haseltine, "Glucocorticoid regulation of murine leukemia virus transcription elements is specified by determinants within the viral enhancer region," *J. Virology*, 61:269, 1987.

Celander, Hsu, and Haseltine, "Regulatory Elements Within the Murine Leukemia Virus Enhancer Regions Mediate Glucocorticoid Responsiveness," *J. Virology*, 62:1314, 1988.

Chandler, Maler, and Yamamoto, "DNA Sequences Bound Specifically by Glucocorticoid Receptor in vitro Render a Heterlogous Promoter Hormone Responsive in vivo," *Cell*, 33:489, 1983.

Chang et al., "Foreign gene delivery and expression in hepatocytes using a hepatitis B virus vector", *Hepatology*, 14:124A, 1991.

Chang, Erwin, and Lee, "Glucose-regulated Protein (GRP94 and GRP78) Genes Share Common Regulatory Domains and are Coordinately Regulated by Common Trans-acting Factors," *Mol. Cell. Biol.*, 9:2153, 1989.

Chang, P. S., Li, L., McAnally, J. and Olson, E. N. (2001) "Muscle specificity encoded by specific serum response factor-binding sites." *J. Biol. Chem.*, 276, 17206–12.

Chatterjee, Lee, Rentoumis, and Jameson, "Negative Regulation of the Thyroid-Stimulating Hormone Alpha Gene by Thyroid Hormone: Receptor Interaction Adjacent to the TATA Box," *Proc Nat'l Acad Sci. USA.*, 86:9114, 1989.

Chen and Okayama, "High-efficiency transfection of mammalian cells by plasmid DNA", *Mol. Cell Biol.*, 7:2745–2752, 1987.

Chen, Kerr, Chang, Honjo, Khalili, "Evidence for regulation of transcription and replication of the human neurotropic virus JCV genome by the human S9mu)bp-2 protein in glial cells," *Gene*, 185:55–62, 1997.

Choi, Chen, Kriegler, and Roninson, "An altered pattern of cross-resistance in multi-drug-resistant human cells results from spontaneous mutations in the mdr-1 (p-glycoprotein) gene," *Cell*, 53:519, 1988.

Clerk, A. & Sugden, P. H. (1999) *Am. J. Cardiol.* 83, 64H-69H.

Coffin, Retroviridae and Their Replication. In: *Virology*, Fields et al., eds., Raven Press, New York, pp. 1437–1500, 1990.

Cohen et al., "A repetitive sequence element 3' of the human c-Ha-ras1 gene has enhancer activity", *J. Cell. Physiol.*, 5:75, 1987

Cook et al., "In vitro splicing of the ribosomal RNA precursor of Tetrahymena: involvement of a guanosine nucleotide in the excision of the intervening sequence," *Cell*, 27:487–496, 1981.

Cooper, J. A. and Schafer, D. A. (2000) Control of actin assembly and disassembly at filament ends. *Curr. Opin. Cell. Biol.*, 12, 97–103.

Costa, Lai, Grayson, and Darnell, "The Cell-Specific Enhancer of the Mouse Transthyretin (Prealbumin) Gene Binds a Common Factor at One Site and a Liver-Specific Factor(s) at Two Other Sites," *Mol. Cell. Biol.*, 8:81, 1988.

Couch et al., "Immunization with types 4 and 7 adenovirus by selective infection of the intestinal tract," *Am. Rev. Resp. Dis.*, 88:394–403, 1963.

Coupar et al., "A general method for the construction of recombinant vaccinia virus expressing multiple foreign genes", *Gene*, 68:1–10, 1988.

Cripe, Haugen, Turk, Tabatabai, Schmid, Durst, Gissmann, Roman, and Turek, "Transcriptional Regulation of the Human Papilloma Virus-16 E6-E7 Promoter by a Keratinocyte-Dependent Enhancer, and by Viral E2 Trans-Activator and Repressor Gene Products: Implications for Cervical Carcinogenesis," *EMBO J.*, 6:3745, 1987.

Cui, Hagan, Zhang, Peltz, "Identification and characterization of genes that are required for the accelerated degradation of mRNAs containing a premature translational termination codon," *Genes Devel.*, 9:423–436, 1995.

Culotta and Hamer, "Fine Mapping of a Mouse Metallothionein Gene Metal-Response Element," *Mol. Cell. Biol.*, 9:1376, 1989.

Czaplinski, Weng, Hagan, Peltz, "Purification and characterization of the Upf1 protein: a factor involved in translation and mRNA degradation," *Rna*, 1:610–623, 1995.

Dandolo, Blangy, and Kamen, "Regulation of Polyma Virus Transcription in Murine Embryonal Carcinoma Cells," *J. Virology*, 47:55, 1983.

De la Cruz, Kressler, Linder, "Undwinding RNA in *Saccharomyces cerevisiae*, DEAD-box proteins and related families," *Trends in Biochem. Sciences*, 24:192–198, 1999.

Dehaan, In *Organogenesis*, Dehaan and Ursprung (Eds.), Holt, Rinehart & Winston, New York, 377–419, 1965.

DeMarini, Winey, Ursic, Webb, Culbertson, "SEN1, a positive effector of tRNA-splicing endonuclease in *Saccharomyces cerevisiae*," *Molecular Cellular Biol.*, 12:2154–2164, 1992.

Deschamps, Meijlink, and Verma, "Identification of a Transcriptional Enhancer Element Upstream From the Proto-Oncogene Fos," *Science*, 230:1174, 1985.

Dubensky et al., "Direct transfection of viral and plasmid DNA into the liver or spleen of mice", *Proc. Nat'l Acad. Sci. USA*, 81:7529–7533, 1984.

Edbrooke, Burt, Cheshire, and Woo, "Identification of cis-acting sequences responsible for phorbol ester induction of human serum amyloid a gene expression via a nuclear-factor-kappa β-like transcription factor," *Mol. Cell. Biol.*, 9:1908, 1989.

Edlund, Walker, Barr, and Rutter, "Cell-specific expression of the rat insulin gene: evidence for role of two distinct 5' flanking elements," *Science*, 230:912, 1985.

Edmondson, Lyons, Martin, Olson, "Mef2 gene expression marks the cardiac and skeletal muscle lineages during mouse embryogenesis," *Development*, 120:1251–1263, 1994.

Ehler, E., Rothen, B. M., Hammerle, S. P., Komiyama, M. and Perriard, J. C., Myofibrillogenesis in the developing chicken heart: assembly of Z-disk, M-line and the thick filaments. *J. Cell Sci.*, 112, 1529–39, 1999.

European Patent App. No. 0273085

Fechheimer, Boylan, Parker, Sisken, Patel and Zimmer, "Transfection of mammalian cells with plasmid DNA by scrape loading and sonication loading," *Proc Nat'l. Acad. Sci. USA* 84:8463–8467, 1987

Feng and Holland, "HIV-I Tat Trans-Activation Requires the Loop Sequence Within Tar," *Nature*, 334:6178, 1988.

Ferkol et al., "Regulation of the phosphoenolpyruvate carboxykinase/human factor IX gene introduced into the livers of adult rats by receptor-mediated gene transfer", *FASEB J.*, 7:1081–1091, 1993.

Firak and Subramanian, "Minimal Transcription Enhancer of Simian Virus 40 is a 74-Base-Pair Sequence that Has Interacting Domains," *Mol. Cell. Biol.*, 6:3667, 1986.

Firulli, McFadden, Lin, Srivastava, Olson, "Heart and extra-embryonic mesodermal defects in mouse embryos lacking the bHLH transcription factor Hand1," *Nature Gene.*, 18:266–270, {YEAR}.

Fishman and Olson, "Parsing the heart: genetic modules for organ assembly," *Cell*, 91:153–156, 1997.

Foecking and Hofstetter, "Powerful and Versatile Enhancer-Promoter Unit for Mammalian Expression Vectors," *Gene*, 45(1):101–105, 1986.

Forster and Symons, "Self-cleavage of plus and minus RNAs of a virusoid and a structural model for the active sites," *Cell*, 49:211–220, 1987.

Fraley, Fomari, Kaplan, "Entrapment of a bacterial plasmid in phospholipid vesicles:potential for gene transfer," *Proc Nat'l. Acad. Sci. USA* 76:3348–3352, 1979.

Franz, Brem, Katus, Klingel, Hofschneider, Kandolf, "Characterization of a cardiac-selective and developmentally upregulated promoter in transgenic mice," *Cardoscience*, 5(4):235–43, 1994.

Freifelder, *Physical Biochemistry Applications to Biochemistry and Molecular Biology*, 2nd ed. Wm. Freeman and Co., New York, N.Y., 1982.

Frey, N., Richardson, J. A., & Olson, E. N., *Proc. Nat'l Acad. Sci. USA* 97, 14632–14637, 2000.

Friedmann, "Progress toward human gene therapy," *Science*, 244:1275–1281, 1989.

Fujita, Shibuya, Hotta, Yamanishi, and Taniguchi, "Interferon-Beta Gene Regulation: Tandemly Repeated Sequences of a Synthetic 6-bp Oligomer Function as a Virus-Inducible Enhancer," *Cell*, 49:357, 1987.

Gefter, Margulies, Scharff, "A simple method for polyethylene glycol-promoted hybridization of mouse myeloma cells," *Somatic Cell Genet.*, 3:231–236, 1977.

Gerlach et al., "Construction of a plant disease resistance gene from the satellite RNA of tobacco rinspot virus," *Nature (London)*, 328:802–805, 1987.

Ghosh and Bachhawat, Targeting of Liposomes to Hepatocytes. In: *Liver Diseases, Targeted Diagnosis and Therapy Using Specific Receptors and Ligands*. Wu et al., eds., Marcel Dekker, New York, pp. 87–104, 1991.

Ghosh-Choudhury et al., "Protein IX, aminor component of the human adenovirus capsid, is essential for the packaging of full-length genomes," *EMBO J.*, 6:1733–1739, 1987.

Gilles, Morris, Oi, and Tonegawa, "A tissue-specific transcription enhancer element is located in the major intron of a rearranged immunoglobulin heavy-chain gene," *Cell*, 33:717, 1983.

Gloss, Bernard, Seedorf, and Klock, "The Upstream Regulatory Region of the Human Papilloma Virus-16 Contains an E2 Protein-Independent Enhancer Which is Specific for Cervical Carcinoma Cells and Regulated by Glucocorticoid Hormones," *EMBO J.*, 6:3735, 1987.

Godbout, Ingram, and Tilghman, "Fine-Structure Mapping of the Three Mouse Alpha-Fetoprotein Gene Enhancers," *Mol. Cell. Biol.*, 8:1169, 1988.

Goddette, D. W. and Frieden, C., The kinetics of cytochalasin D binding to monomeric actin. *J. Biol. Chem.*, 261, 15970–3, 1986.

Goding, 1986, In: *Monoclonal Antibodies: Principles and Practice*, 2d ed., Academic Press, Orlando, Fla., pp. 60–61, and 71–74, 1986.

Gomez-Foix et al., "Adenovirus-mediated transfer of the muscle glycogen phosphorylase gene into hepatocytes confers altered regulation of glycogen," *J. Biol. Chem.*, 267:25129–25134, 1992.

Goodbourn and Maniatis, "Overlapping Positive and Negative Regulatory Domains of the Human β-Interferon Gene," *Proc. Nat'l Acad. Sci. USA*, 85:1447, 1988.

Goodbourn, Burstein, and Maniatis, "The Human Beta-Interferon Gene Enhancer is Under Negative Control," *Cell*, 45:601, 1986.

Gopal, "Gene transfer method for transient gene expression, stable transfection, and cotransfection of suspension cell cultures," *Mol. Cell Biol.*, 5:1188–1190, 1985.

Gopal-Srivastava, Haynes, Piatigorsky, "Regulation of the murine αB-crystallin/small heat shock protein gene in cardiac muscle," *Muscle Cell. Biol.*, 15:7081–7090, 1995.

Graham and Prevec, In: *Methods in Molecular Biology: Gene Transfer and Expression Protocol*, E. J. Murray, ed., Humana Press, Clifton, N. J., 7:109–128, 1991.

Graham and van der Eb, "A new technique for the assay of infectivity of human adenovirus 5 DNA", *Virology*, 52:456–467, 1973.

Graham et al., "Characteristics of a human cell line transformed by DNA from human adenovirus type 5", *J. Gen. Virol.*, 36:59–72, 1977.

Greene, Bohnlein, and Ballard, "HIV-1, and Normal T-Cell Growth: Transcriptional Strategies and Surprises," *Immunology Today*, 10:272, 1989

Gregorio, C. C. and Antin, P. B., To the heart of myofibril assembly. *Trends Cell. Biol.*, 10, 355–62, 2000.

Grosschedl and Baltimore, "Cell-Type Specificity of Immunoglobulin Gene Expression is Regulated by at Least Three DNA Sequence Elements," *Cell*, 41:885, 1985.

Grunhaus and Horwitz, "Adenovirus as cloning vector," *Seminar in Virology*, 3:237–252, 1992.

Guan, K. L. and Dixon, J. E., Eukaryotic proteins expressed in *Escherichia coli*: an improved thrombin cleavage and purification procedure of fusion proteins with glutathione S-transferase. Anal Biochem, 192, 262–7, 1991.

Gulley, Zhang, Gascoyne, DuPont, Banks, Cho, Huang, Montalvo, "Translocations of 11q13 in mantle cell lymphoma fail to disrupt the S mu bp-2 gene," *Hematopathology Molecular Hematology*, 11:1–11, 1997.

Han and Prywes, "Regulatory role of MEF2D in serum induction of the c-jun promoter," *Molecular Cellular Biology*, 15:2907–2915, 1995.

Harland and Weintraub, "Translation of mammalian mRNA injected into Xenopus oocytes is specifically inhibited by antisense RNA", *J. Cell Biol.*, 101:1094–1099, 1985.

Harlow and Lane, Antibodies: A Laboratory manual, Cold Spring Harbor Laboratory, 1988.

Haslinger and Karin, "Upstream Promoter Element of the Human Metallothionein-II Gene Can Act Like an Enhancer Element," *Proc Nat'l Acad. Sci. U.S.A.*, 82:8572, 1985.

Hauber and Cullen, "Mutational Analysis of the Trans-Activation-Responsive Region of the Human Immunodeficiency Virus Type I Long Terminal Repeat," *J. Virology*, 62:673, 1988.

Hen, Borrelli, Fromental, Sassone-Corsi, and Chambon, "A Mutated Polyoma Virus Enhancer Which is Active in Undifferentiated Embryonal Carcinoma Cells is not Repressed by Adenovirus-2 E1A Products," *Nature*, 321: 249, 1986.

Hensel, Meichle, Pfizenmaier, and Kronke, "PMA-Responsive 5'Flanking Sequences of the Human TNF Gene," *Lymphokine Res.*, 8:347, 1989.

Hermonat and Muzycska, "Use of adenoassociated virus as a mammalian DNA cloning vector: Transduction of neomycin resistance into mammalian tissue culture cells", *Proc. Nat'l Acad. Sci. USA*, 81:6466–6470, 1984.

Hersdorffer et al., "Efficient gene transfer in live mice using a unique retroviral packaging line," *DNA Cell Biol.*, 9:713–723, 1990.

Herz and Gerard, "Adenovirus-mediated transfer of low density lipoprotein receptor gene acutely accelerates cholesterol clearance in normal mice," *Proc. Nat'l. Acad. Sci. USA* 90:2812–2816, 1993.

Hines, W. A., Thorbum, J. and Thorbum, A., A low-affinity serum response element allows other transcription factors to activate inducible gene expression in cardiac myocytes. *Mol. Cell Biol.*, 19, 1841–52, 1999.

Hirochika, Browker, and Chow, "Enhancers and Trans-Acting E2 Transcriptional Factors of Papilloma Viruses," *J. Virol.*, 61:2599, 1987.

Hirsch, Gaugler, Deagostini-Bauzin, Bally-Cuif, and Gordis, "Identification of Positive and Negative Regulatory Elements Governing Cell-Type-Specific Expression of the Neural-Cell-Adhesion-Molecule Gene," *Mol. Cell. Biol.*, 10:1959, 1990.

Holbrook, Gulino, and Ruscetti, "cis-Acting Transcriptional Regulatory Sequences in the Gibbon Ape Leukemia Virus (GALV) Long Terminal Repeat," *Virology*, 157:211, 1987.

Horlick and Benfield, "The Upstream Muscle-Specific Enhancer of the Rat Muscle Creatine Kinase Gene is Composed of Multiple Elements," *Mol. Cell. Biol.*, 9:2396, 1989.

Horwich, et al., "Synthesis of hepadnavirus particles that contain replication-defective duck hepatitis B virus genomes in cultured HuH7 cells," *J. Virol.*, 64:642–650, 1990.

Hoshijima, M., Sah, V. P., Wang, Y., Chien, K. R. and Brown, J. H., The low molecular weight GTPase Rho regulates myofibril formation and organization in neonatal rat ventricular myocytes. Involvement of Rho kinase. *J. Biol. Chem.*, 273, 7725–30, 1998.

Huang et al, "A cellular protein that competes with SV40 antigen for binding to the retinoblastoma gene product," *Nature*, 350:160–162, 1991.

Hubank, M. and Schatz, D. G., cDNA representational difference analysis: a sensitive and flexible method for identification of differentially expressed genes. *Methods in Enzymology*, 303, 325–49, 1999.

Hug, Costas, Staeheli, Aebi, and Weissmann, "Organization of the Murine Mx Gene and Characterization of its Interferon- and Virus-Inducible Promoter," *Mol. Cell. Biol.*, 8:3065, 1988.

Hwang, Lim, and Chae, "Characterization of the S-Phase-Specific Transcription Regulatory Elements in a DNA-Replication-Independent Testis-Specific H2B (TH2B) Histone Gene," *Mol. Cell. Biol.*, 10:585, 1990.

Imagawa, Chiu, and Karin, "Transcription Factor AP-2 Mediates Induction by Two Different Signal-Transduction Pathways: Protein Kinase C and cAMP," *Cell*, 51:251, 1987.

Imbra and Karin, "Phorbol Ester Induces the Transcriptional Stimulatory Activity of the SV40 Enhancer," *Nature*, 323:555, 1986.

Imler, Lemaire, Wasvlyk, and Waslyk, "Negative Regulation Contributes to Tissue Specificity of the Immunoglobulin Heavy-Chain Enhancer," *Mol. Cell. Biol*, 7:2558, 1987.

Imperiale and Nevins, "Adenovirus 5 E2 Transcription Unit: an E1A-Inducible Promoter with an Essential Element that Functions Independently of Position or Orientation," *Mol. Cell. Biol.*, 4:875, 1984.

Innis et al., "DNA sequencing with *Thermus aquaticus* DNA polymerase and direct sequencing of polymerase chain reaction-amplified DNA," *Proc. Nat'l Acad. Sci. U.S.A.* 85(24):9436–9440, 1988.

Jakobovits, Smith, Jakobovits, and Capon, "A Discrete Element 3' of Human Immunodeficiency Virus 1 (HIV-1) and HIV-2 mRNA Initiation Sites Mediates Transcriptional Activation by an HIV Trans-Activator," *Mol. Cell. Biol.*, 8:2555, 1988.

Jameel and Siddiqui, "The Human Hepatitis B Virus Enhancer Requires Transacting Cellular Factor(s) for Activity," *Mol. Cell. Biol.*, 6:710, 1986.

Jaynes, Johnson, Buskin, Gartside, and Hauschka, "The Muscle Creatine Kinase Gene is Regulated by Multiple Upstream Elements, Including a Muscle-Specific Enhancer," *Mol. Cell. Biol.*, 8:62, 1988.

Johnson et al., Peptide Turn Mimetics" IN: *Biotechnology And Pharmacy*, Pezzuto et al., eds., Chapman and Hall, New York, 1993.

Johnson, Wold, and Hauschka, "Muscle creatine kinase sequence elements regulating skeletal and cardiac muscle expression in transgenic mice," *Mol. Cell. Biol.*, 9:3393, 1989.

Jones and Shenk, "Isolation of deletion and substitution mutants of adenovirus type 5," *Cell*, 13:181–188, 1978.

Joyce, "RNA evolution and the origins of life," *Nature*, 338:217–244, 1989.

Juliano, R. L. and Haskill, S., Signal transduction from the extracellular matrix. *J. Cell Biol.*, 120, 577–85, 1993.

Kadesch and Berg, "Effects of the Position of the Simian Virus 40 Enhancer on Expression of Multiple Transcription Units in a Single Plasmid," *Mol. Cell. Biol.*, 6:2593, 1986.

Kaibuchi, K., Kuroda, S. and Amano, M., Regulation of the cytoskeleton and cell adhesion by the Rho family GTPases in mammalian cells. *Annu. Rev. Biochem.*, 68, 459–86, 1999.

Kaneda et al., "Increased expression of DNA cointroduced with nuclear protein in adult rat liver", *Science*, 243: 375–378, 1989.

Karin, Haslinger, Heguy, Dietlin, and Cooke, "Metal-Responsive Elements Act as Positive Modulators of Human Metallothionein-IIA Enhancer Activity," *Mol. Cell. Biol.*, 7:606, 1987.

Karlsson et al., *EMBO J.*, 5:2377–2385, 1986.

Katinka, Vasseur, Montreau, Yaniv, and Blangy, "Polyoma DNA Sequences Involved in the Control of Viral Gene Expression in Murine Embryonal Carcinoma Cells," *Nature*, 290:720, 1981.

Katinka, Yaniv, Vasseur, and Blangy, "Expression of Polyoma Early Functions in Mouse Embryonal Carcinoma Cells Depends on Sequence Rearrangements in the Beginning of the Late Region," *Cell*, 20:393, 1980.

Kato et al., "Expression of hepatitis β virus surface antigen in adult rat liver. Co-introduction of DNA and nuclear protein by a simplified liposome method," *J. Biol. Chem.*, 266(6):3361-3364, 1991.

Kawamoto, Makino, Niw, Sugiyama, Kimura, Anemura, Nakata, and Kakunaga, "Identification of the Human Beta-Actin Enhancer and its Binding Factor," *Mol. Cell. Biol.*, 8:267, 1988.

Kelly, Alonso, Tajbakhsh, Cossu, Buckingham, "Myosin light chain 3F regulatory sequences confer regionalized cardiac and skeletal muscle expression in transgenic mice," *J. Cell Biol.*, 129(2):383–96, 1995.

Kiledjian, Su, Kadesch, "Identification and characterization of two functional domains within the murine heavy-chain enhancer," *Mol. Cell. Biol.*, 8:145, 1988.

Kim and Cook, "Three dimensional model of the active site of the self-splicing rRNA precursor or Tetrahymena," *Proc. Nat'l Acad. Sci. USA*, 84:8788–8792, 1987.

Kim, Choe, Seo, "The sen1(+) gene of *Schizosaccharomyces pombe*, a homologue of budding yeast SEN1, encodes an RNA and DNA helicase," *Biochemistry*, 38:14697–14710, 1999.

Kim, S., Ip, H. S., Lu, M. M., Clendenin, C. and Parmacek, M. S. (1997) A serum response factor-dependent transcriptional regulatory program identifies distinct smooth muscle cell sublineages. *Mol. Cell Biol.*, 17, 2266–78.

Kimura, Abe, Suzuki, Ogawa, Yoshioka, Kaname, Miike, Yamamura, "A 900 bp genomic region from the mouse dystrophin promoter directs lacZ reporter expression only to the right heart of transgenic mice," *Dev. Growth Differ.*, 39(3):257–65, 1997.

Klamut, Gangopadyhay, Worton, and Ray, "Molecular and Functional Analysis of the Muscle-Specific Promoter Region of the Duchenne Muscular Dystrophy Gene," *Mol. Cell. Biol.*, 10:193, 1990.

Klein et al., "High-velocity microprojectiles for delivering nucleic acids into living cells", *Nature*, 327:70–73, 1987.

Koch, Benoist, and Mathis, "Anatomy of a new β-cell-specific enhancer," *Mol. Cell. Biol.*, 9:303, 1989.

Kohler and Milstein, "Continuous cultures of fused cells secreting antibody of predefined specificity," *Nature*, 256: 495–497, 1975.

Kohler and Milstein, "Derivation of specific antibody-producing tissue culture and tumor lines by cell fusion," *Eur. J. Immunol.*, 6:511–519, 1976.

Kriegler and Botchan, "Enhanced transformation by a simian virus 40 recombinant virus containing a Harvey murine sarcoma virus long terminal repeat," *Mol. Cell. Biol.* 3:325, 1983.

Kriegler and Botchan, In: *Eukaryotic Viral Vectors*, Y. Gluzman, ed., Cold Spring Harbor: Cold Spring Harbor Laboratory, NY, 1982.

Kriegler et al., "Promoter substitution and enhancer augmentation increases the penetrance of the sv40 a gene to levels comparable to that of the harvey murine sarcoma virus ras gene in morphologic transformation," In: *Gene Expression*, Alan Liss (Ed.), Hamer and Rosenberg, New York, 1983.

Kriegler et al., "Transformation Mediated by the SV40 T Antigens: Separation of the Overlapping SV40 Early Genes with a Retroviral Vector," *Cell*, 38:483, 1984.

Kriegler et al., "Viral Integration and Early Gene Expression Both Affect the Efficiency of SV40 Transformation of Murine Cells: Biochemical and Biological Characterization of an SV40 Retrovirus," In: *Cancer Cells 2/Oncogenes and Viral Genes*, Van de Woude et al. eds, Cold Spring Harbor: Cold Spring Harbor Laboratory, 1984.

Kriegler, Perez, Defay, Albert and Liu, "A Novel Form of TNF/Cachectin Is a Cell-Surface Cytotoxix Transmembrane Protein: Ramifications for the Complex Physiology of TNF," *Cell*, 53:45, 1988.

Kuhl, De La Fuenta, Chaturvedi, Parinool, Ryals, Meyer, and Weissman, "Reversible Silencing of Enhancers by Sequences Derived From the Human IFN-alpha Promoter," *Cell*, 50:1057, 1987.

Kuisk, Li, Tran, Capetanaki, "A single MEF2 site governs desmin transcription in both heart and skeletal muscle during mouse embryogenesis," *Developmental Biology*, 174:1–13, 1996.

Kunz, Zimmerman, Heisig, and Heinrich, "Identification of the Promoter Sequences Involved in the Interleukin-6-Dependent Expression of the Rat Alpha-2-Macroglobulin Gene," *Nucl. Acids Res.*, 17:1121, 1989.

Kuo, Morrisey, Anandappa, Sigrist, Lu, Parmacek, Soudais, Leiden, "GATA4 transcription factor is required for ventral morphogenesis and heart tube formation," *Genes Development*, 11:1048–1060, 1997.

Kyte and Doolittle, "A simple method for displaying the hydropathic character of a protein," *J. Mol. Biol.*, 157(1): 105–132, 1982.

LaPointe, Wu, Greenberg, Gardner, "Upstream sequences confer atrial-specific expression on the human atrial natriuretic factor gene." *J. Biol. Chem.*, 263(19):9075–8, 1988.

Larsen, Harney, and Moore, "Repression medaites cell-type-specific expression of the rat growth hormone gene," *Proc Nat'l Acad. Sci. USA.*, 83:8283, 1986.

Laspia, Rice, and Mathews, "HIV-1 Tat protein increases transcriptional initiation and stabilizes elongation," *Cell*, 59:283, 1989.

Latimer, Berger, and Baumann, "Highly conserved upstream regions of the $\alpha_1$-antitrypsin gene in two mouse species govern liver-specific expression by different mechanisms," *Mol. Cell. Biol.,* 10:760, 1990.

Le Gal La Salle et al., "An adenovirus vector for gene transfer into neurons and glia in the brain," *Science,* 259:988–990, 1993.

Lee, Mulligan, Berg, and Ringold, "Glucocorticoids Regulate Expression of Dihydrofolate Reductase cDNA in Mouse Mammary Tumor Virus Chimaeric Plasmids," *Nature,* 294:228, 1981.

Leeds, Peltz, Jacobson, Culbertson, "The product of the yeast UPF1 gene is required for rapid turnover of mRNAs containing a premature translational termination codon," *Genes Development,* 5:2303–2314, 1991.

Lelivelt and Culbertson, "Yeast Upf proteins required for RNA surveillance affect global expression of the eyast transcriptome," *Molecular Cellular Biology,* 19:6710–6719, 1999.

Levinson, Khoury, VanDeWoude, and Gruss, "Activation of SV40 Genome by 72-Base-Pair Tandem Repeats of Moloney Sarcoma Virus," *Nature,* 295:79, 1982.

Levrero et al., "Defective and nondefective adenovirus vectors for expressing foreign genes in vitro and in vivo," *Gene,* 101:195–202, 1991.

Li, J. M. & Grooks, G., *Eur. Heart J* 20, 406–420, 1999.

Li, L., Liu, Z., Mercer, B., Overbeek, P. and Olson, E. N., Evidence for serum response factor-mediated regulatory networks governing SM22alpha transcription in smooth, skeletal, and cardiac muscle cells. *Dev. Biol.,* 187, 311–21, 1997.

Li, L., Miano, J. M., Mercer, B. and Olson, E. N., Expression of the SM22 promoter in transgenic mice provides evidence for distinct transcriptional regulatory programs in vascular and visceral smooth muscle cells. *J. Cell Biol.* 132, 1–11, 1996.

Lilly, Galewsky, Firulli, Schulz, Olson, "D-MEF2: a MADs box transcription factor expressed in differentiating mesoderm and muscle cell lineages during *Drosophila* embryogenesis," *Proc. Nat'l Acad. Sci. USA,* 91:5662–5666, 1994.

Lilly, Zhao, Ranganayakulu, Paterson, Schulz, Olson "Requirement of MADS domain transcription factor D-MEF2 for muscle formation in *Drosophila*," *Science,* 267:688–693, 1995.

Lin, Cross, Halden, Dragos, Toledano, and Leonard, "Delineation of an enhancerlike positive regulatory element in the interleukin-2 receptor α-chain gene," *Mol. Cell. Biol.,* 10:850, 1990.

Lin, Schwarz, Bucana, Olson, "Control of mouse cardiac morphogenesis and myogenesis by transcription factor MEF2C," *Science,* 276:1404–1407, 1997.

Liu, Z. P., Nakagawa, O., Nakagawa, M., Yanagisawa, H., Passier, R., Richardson, J. A., Srivastava, D., & Olson, E. N. *Dev. Biol.* 234, 497–509, 2001.

Luria, Gross, Horowitz, and Givol, "Promoter Enhancer Elements in the Rearranged Alpha-Chain Gene of the Human T-Cell Receptor," *EMBO J.,* 6:3307, 1987.

Lusky and Botchan, "Transient Replication of Bovine Papilloma Virus Type 1 Plasmids: cis and trans Requirements," *Proc Nat'l Acad. Sci. U.S.A.,* 83:3609, 1986.

Lusky, Berg, Weiher, and Botchan, "Bovine Papilloma Virus Contains an Activator of Gene Expression at the Distal End of the Early Transcription Unit," *Mol. Cell. Biol.* 3:1108, 1983.

Macejak and Sarnow, "Internal initiation of translation mediated by the 5' leader of a cellular mRNA," *Nature,* 353:90–94, 1991.

Mack, C. P., Somlyo, A. V., Hautmann, M., Somlyo, A. P. and Owens, G. K., Smooth muscle differentiation marker gene expression is regulated by RhoA-mediated actin polymerization. *J. Biol. Chem.,* 276, 341–7, 2001.

Maekawa, M., Ishizaki, T., Boku, S., Watanabe, N., Fujita, A., Iwamatsu, A., Obinata, T., Ohashi, K., Mizuno, K. and Narumiya, S., Signaling from Rho to the actin cytoskeleton through protein kinases ROCK and LIM-kinase. *Science,* 285, 895–8, 1999.

Majors and Varmus, "A Small Region of the Mouse Mammary Tumor Virus Long Terminal Repeat Confers Glucocorticoid Hormone Regulation on a Linked Heterologous Gene," *Proc. Nat'l Acad. Sci. USA,* 80:5866, 1983.

Manipulating the Mouse Embryo: A Laboratory Manual, 2nd ed., Hogan et al., eds., Cold Spring Harbor Laboratory Press, 1994.

Mann et al., "Construction of a retrovirus packaging mutant and its use to produce helper-free defective retrovirus", *Cell,* 33:153–159, 1983.

Markowitz et al., "A safe packaging line for gene transfer: Separating viral genes on two different plasmids," *J. Virol.,* 62:1120–1124, 1988.

McNeall, Sanchez, Gray, Chesterman, and Sleigh, "Hyperinducible Gene Expression From a Metallotionein Promoter Containing Additional Metal-Responsive Elements," *Gene,* 76:81, 1989.

Merrifield, "Solid phase synthesis," *Science,* 232: 341–347, 1986.

Michel and Westhof, "Modeling of the three-dimensional architecture of group I catalytic introns based on comparative sequence analysis," *J. Mol. Biol.,* 216:585–610, 1990.

Miksicek, Heber, Schmid, Danesch, Posseckert, Beato, and Schutz, "Glucocorticoid Responsiveness of the Transcriptional Enhancer of Moloney Murine Sarcoma Virus," *Cell,* 46:203, 1986.

Molkentin and Olson, "GATA4: a novel transcriptional regulator of cardiac hypertrophy?" *Circulation,* 96:3833–3835, 1997.

Molkentin, J. D., Lu, J. R., Antos, C. L., Markham, B., Richardson, J., Robbins, J., Grant, S. R. and Olson, E. N., A calcineurin-dependent transcriptional pathway for cardiac hypertrophy. *Cell,* 93, 215–28, 1998.

Molkentin, J. D., Lu, J. R., Antos, C. L., Markham, B., Richardson, J., Robbins J., Grant, S. R., & Olson, E. N. (1998) *Cell* 93, 215–228.

Mordacq and Linzer, "Co-localization of Elements Required for Phorbol Ester Stimulation and Glucocorticoid Repression of Proliferin Gene Expression," *Genes and Dev.,* 3:760, 1989.

Moreau, Hen, Wasylyk, Everett, Gaub, and Chambon, "The SV40 base-repair repeat has a striking effect on gene expression both in sv40 and other chimeric recombinants," *Nucl. Acids Res.,* 9:6047, 1981.

Morton, W. M., Ayscough, K. R. and McLaughlin, P. J., Latrunculin alters the actin-monomer subunit interface to prevent polymerization. *Nat. Cell Biol.,* 2, 376–8, 2000.

Moss, Marshall, Moczydlowski, "Hypothesis for a serine proteinase-like domain at the COOH terminus of Slowpoke calcium-activated potassium channels," *J. Gen. Physiol.,* 108(6):473–84, 1996.

Musesing, Smith, and Capon, "Regulation of mRNA Accumulation by a Human Immunodeficiency Virus Trans-Activator Protein," *Cell,* 48:691, 1987.

Nakagawa, Nakagawa, Richardson, Olson, Srivastava, "HRT1, HRT2, and HRT3: a new subclass of bHLH transcription factors marking specific cardiac, somitic, and pharyngeal arch segment," *Develop. Biol.*, 216:72–84, 1999.

Nakajima, Uchida, Anderson, Lee, Hurwitz, Parvin, Montminy, "RNA helicase A mediates association of CBP with RNA polymerase II," *Cell*, 90:1107–1112, 1997.

Narumiya, S., Ishizaki, T. and Watanabe, N., Rho effectors and reorganization of actin cytoskeleton. *FEBS Lett.*, 410, 68–72, 1997.

Naya and Olson, "MEF2: a transcriptional target for signaling pathways controlling skeletal muscle growth and differentiation," *Curr. Opinion Cell Biol.*, 11:683–688, 1999.

Nemoto, Y., Namba, T., Teru-uchi, T., Ushikubi, F., Morii, N. and Narumiya, S., A rho gene product in human blood platelets. I. Identification of the platelet substrate for botulinum C3 ADP-ribosyltransferase as rhoA protein. *J. Biol. Chem.*, 267, 20916–20, 1992.

Ng, Gunning, Liu, Leavitt, and Kedes, "Regulation of the Human Beta-Actin Promoter by Upstream and Intron Domains," *Nuc. Acids Res.*, 17:601, 1989.

Nguyen, Bodmer, Abmayr, McDermott, Spoerel, "D-mef2: a *Drosophila* mesoderm-specific MADS box-containing gene with a biphasic expresssion profile during embryogenesis," *Proc. Nat'l Acad. Sci. USA*, 91:7520–7524, 1994.

Nicol, R. L., Frey, N., Pearson, G., Cobb, M., Richardson, J. and Olson, E. N., Activated MEK5 induces serial assembly of sarcomeres and eccentric cardiac hypertrophy. *EMBO J.*, 20, 2757–67, 2001.

Nicol, R. L., Frey, N., Pearson, G., Cobb, M., Richardson, J., & Olson, E. N., *EMBO J.* 20, 2757–2767, 2001.

Nicolas and Rubinstein, In: *Vectors: A survey of molecular cloning vectors and their uses*, Rodriguez and Denhardt, eds., Stoneham: Butterworth, pp. 494–513, 1988.

Nicolau and Sene, "Liposome-mediated DNA transfer in eukaryotic cells", *Biochim. Biophys. Acta*, 721:185–190, 1982.

Nicolau et al., "Liposomes as carriers for in vivo gene transfer and expression," *Methods Enzymol.*, 149:157–176, 1987.

Nozato, T., Ito, H., Watanabe, M., Ono, Y., Adachi, S., Tanaka, H., Hiroe, M., Sunamori, M., & Marum, F., *J. Mol. Cell. Cardiol.* 33, 1493–1504, 2000.

Olson and Srivastava, "Molecular pathways controlling heart development," *Science*, 272:671–676, 1996.

Ondek, Sheppard, and Herr, "Discrete Elements Within the SV40 Enhancer Region Display Different Cell-Specific Enhancer Activities," *EMBO J.*, 6:1017, 1987.

Ornitz, Hammer, Davison, Brinster, and Palmiter, "Promoter and enhancer elements from the rat elastase i gene function independently of each other and of heterologous enhancers," Mol. Cell. Biol. 7:3466, 1987.

Palmiter, Chen, and Brinster, "Differential regulation of metallothionein-thymidine kinase fusion genes in transgenic mice and their offspring," *Cell*, 29:701, 1982.

Pantaloni, D., Le Clainche, C. and Carlier, M. F., Mechanism of actin-based motility. *Science*, 292, 1502–6, 2001.

Paskind et al., "Dependence of moloney murine leukemia virus production on cell growth", *Virology*, 67:242–248, 1975.

Passier, Xheng, Frey, Naya, Nicol, McKinsey, Overbeek, Richardson, Grant, Olson, "CaM kinase signaling induces cardiac hypertrophy and activates the MEF2 transcription factor in vivo," *J. Clin. Invest.*, 105(10):1395–406, 2000.

Pech, Rao, Robbins, and Aaronson, "Functional identification of regulatory elements within the promoter region of platelet-derived growth factor 2," *Mol. Cell Biol.*, 9:396, 1989.

Pelletier and Sonenberg, "Internal initiation of translation of eukaryotic mRNA directed by a sequence derived from poliovirus RNA," *Nature*, 334:320–325, 1988.

Perales, Ferkol, Beegen, Ratnoff, Hanson, "Gene transfer in vivo: sustained expression and regulation of genes introduced into the liver by receptor-targeted uptake," *Proc. Nat'l Acad. Sci. USA*, 91(9):4086–4090, 1994.

Perez-Stable and Constantini, "Roles of fetal y-globin promoter elements and the adult P-globin 3' enhancer in the stage-specific expression of globin genes," *Mol. Cell. Biol.*, 10:1116, 1990.

Picard and Schaffner, "A lymphocyte-specific enhancer in the mouse immunoglobulin kappa gene," *Nature*, 307:83, 1984.

Pignon, Vinatier, Fanen, Jonveaux, Toumilhac, Imbert, Rochant, Goossens, "Exhaustive analysis of the P53 gene coding sequence by denaturing gradient gel electrophoresis: application to the detection of point mutations in acute leukemias," *Hum. Mutat.*, 3: 126–132, 1994.

Pinkert, Omitz, Brinster, and Palmiter, "An albumin enhancer located 10 kb upstream functions along with its promoter to direct efficient, liver-specific expression in transgenic mice," *Genes and Dev.*, 1:268, 1987.

Ponta, Kennedy, Skroch, Hynes, and Groner, "Hormonal Response Region in the Mouse Mammary Tumor Virus Long Terminal Repeat Can Be Dissociated From the Proviral Promoter and Has Enhancer Properties," *Proc. Nat'l Acad. Sci. U.S.A.*, 82:1020, 1985.

Porton, Zaller, Lieberson, and Eckhardt, "Immunoglobulin heavy-chain enhancer is required to maintain transfected .gamma.2a gene expression in a pre-b-cell line," *Mol. Cell. Biol.*, 10:1076, 1990.

Potter et al., "Enhancer-dependent expression of human k immunoglobulin genes introduced into mouse pre-B lymphocytes by electroporation," *Proc. Nat'l Acad. Sci. USA*, 81:7161–7165, 1984.

Queen and Baltimore, "Immunoglobulin gene transcription is activated by downstream sequence elements," *Cell*, 35:741, 1983.

Quinn, Farina, Gardner, Krutzsch, and Levens, "Multiple components are required for sequence recognition of the ap1 site in the gibbon ape leukemia virus enhancer," *Mol. Cell. Biol.*, 9:4713, 1989.

Racher et al., *Biotechnology Techniques*, 9:169–174, 1995.

Ragot et al., "Efficient adenovirus-mediated transfer of a human minidystrophin gene to skeletal muscle of mdx mice," *Nature*, 361:647–650, 1993.

Rando, O. J., Zhao, K. and Crabtree, G. R., Searching for a function for nuclear actin. *Trends Cell Biol.*, 10, 2000.

Ranganayakulu, Zhao, Dokidis, Molentin, Olson, Schulz, "A series of mutations in the D-MEF2 transcription factor reveal multiple functions in larval and adult myogenesis in *Drosophila*, *Dev. Biology*, 171:169–181, 1995.

Redondo, Hata, Brocklehurst, and Krangel, "A T-Cell-Specific Transcriptional Enhancer Within the Human T-Cell Receptor .delta Locus," *Science*, 247:1225, 1990.

Reinhold-Hurek and Shub, "Self-splicing introns in tRNA genes of widely divergent bacteria," *Nature*, 357:173–176, 1992.

Reisman and Rotter, "Induced expression from the moloney murine leukemia virus long terminal repeat during differentiation of human myeloid cells is mediated through its transcriptional enhancer," *Mol. Cell. Biol.*, 9:3571, 1989.

Reiter, Alexander, Rodaway, Yelon, Pateint, Holder, Stainer, "Gata5 is required for the development of theart and endoderm in zebrafish," *Genes Develop.*, 13:2983–2995, 1999.

Renan, "Cancer genes: Current status, future prospects and applications in radiotherapy/oncology," *Radiother. Oncol.*, 19:197–218, 1990.

Resendez Jr., Wooden, and Lee, "Identification of highly conserved regulatory domains and protein-binding sites in the promoters of the rat and human genes encoding the stress-inducible 78-kilodalton glucose-regulated protein," *Mol. Cell. Biol.*, 8:4579, 1988.

Rich et al., "Development and analysis of recombinant adenoviruses for gene therapy of cystic fibrosis," *Hum. Gene Ther.*, 4:461–476, 1993.

Ridgeway, Mammalian Expression Vectors, In: *Vectors: A Survey of Molecular Cloning Vectors and Their Uses*, Rodriguez et al., eds., Stoneham: Butterworth, pp. 467–492, 1988.

Ridley, A. J. and Hall, A., The small GTP-binding protein rho regulates the assembly of focal adhesions and actin stress fibers in response to growth factors. *Cell*, 70, 389–99, 1992.

Ripe, Lorenzen, Brenner, and Breindl, "Regulatory elements in the 5' flanking region and the first intron contribute to transcriptional control of the mouse alpha-1-type collagen gene," *Mol. Cell. Biol.*, 9:2224, 1989.

Rippe, Brenner and Leffert, "DNA-mediated gene transfer into adult rat hepatocytes in primary culture," *Mol. Cell Biol.*, 10:689–695, 1990.

Rittling, Coutinho, Amarm, and Kolbe, "AP-1/jun-binding Sites Mediate Serum Inducibility of the Human Vimentin Promoter," *Nuc. Acids Res.*, 17:1619, 1989.

Rosen, Sodroski, and Haseltine, "The location of cis-acting regulatory sequences in the human t-cell lymphotropic virus type III (HTLV-111/LAV) long terminal repeat," *Cell*, 41:813, 1988.

Rosenfeld, Siegfried, Yoshimura, Yoneyama, Fukayama, Stier, Paakko, Gilardi, Stratford-Perricaudet, Perricaudet, Jallat, Pavirani, Lecocq, Crystal, "Adenovirus-mediated transfer of a recombinant α1-antitrypsin gene to the lung epithelium in vivo," *Science*, 252:431–434,1991.

Rosenfeld, Yoshimura, Trapnell, Yoneyama, Rosenthal, Dalemans, Fukayama, Bargon, Stier, Stratford-Perricaudet, Perricaudet, Guggino, Pavirani, Lecocq, Crystal, "In vivo transfer of the human cystic fibrosis transmembrane conductance regulator gene to the airway epithelium," *Cell*, 68:143–155,1992.

Ross, Navankasattusas, Harvey, Chien, "An HF-1a/HF-1b/MEF-2 combinatorial element confers cardiac ventricular specificity and established an anterior-posterior gradient of expression," *Development*, 122:1799–1809, 1996.

Roux et al., "A versatile and potentially general approach to the targeting of specific cell types by retroviruses: Application to the infection of human cells by means of major histocompatibility complex class I and class II antigens by mouse ecotropic murine leukemia virus-derived viruses", *Proc. Nat'l Acad. Sci. USA*, 86:9079–9083, 1989.

Sakai, Helms, Carlstedt-Duke, Gustafsson, Rottman, and Yamamoto, "Hormone-Mediated Repression: A Negative Glucocorticoid-Response Element From the Bovine Prolactin Gene," *Genes and Dev.*, 2:1144, 1988.

Sambrook, Fritsch, Maniatis, *Molecular Cloning: A Laboratory Manual*, 2nd Ed., Cold Spring Harbor Press, Cold Spring Harbor, N.Y., 1989.

Sampath, P. and Pollard, T., Effects of cytochalasin, phalloidin, and pH on the elongation of actin filaments. *Biochemistry* (Mosc), 30, 1973–80, 1991.

Sarver, et al, "Ribozymes as potential anti-HIV-1 therapeutic agents," *Science*, 247:1222–1225, 1990.

Satake, Furukawa, and Ito, "Biological activities of oligonucleotides spanning the f9 point mutation within the enhancer region of polyoma virus DNA," *J. Virology*, 62:970, 1988.

Scanlon et al., "Ribozyme-mediated cleavages of c-fos mRNA reduce gene expression of DNA synthesis enzymes and metallothionein," *Proc. Nat'l Acad. Sci. USA*, 88:10591–10595, 1991.

Schaffner, Schirm, Muller-Baden, Wever, and Schaffner, "Redundancy of Information in Enhancers as a Principle of Mammalian Transcription Control," *J. Mol. Biol.*, 201:81, 1988.

Searle, Stuart, and Palmiter, "Building a metal-responsive promoter with synthetic regulatory elements," *Mol. Cell. Biol.*, 5:1480, 1985.

Sebastiani, Durocher, Gros, Nemer, Malo, "Localization of the Catf1 transcription factor gene to mouse chromosome 19," *Mammalian Genome*, 6:147–148, 1995.

Sedmera, D., Pexieder, T., Vuillemin, M., Thompson, R. P., & Anderson, R. H., *Anat. Rec.* 258, 319–337, 2000.

Sharp and Marciniak, "HIV Tar: an RNA Enhancer?," *Cell*, 59:229, 1989.

Shaul and Ben-Levy, "Multiple Nuclear Proteins in Liver Cells are Bound to Hepatitis B Virus Enhancer Element and its Upstream Sequences," *EMBO J*, 6:1913, 1987.

Sherman, Basta, Moore, Brown, and Ting, "Class II Box Consensus Sequences in the HLA-DRα. Gene: Transcriptional Function and Interaction with Nuclear Proteins," *Mol. Cell. Biol.*, 9:50, 1989. Siomi and Dreyfuss, "RNA-binding proteins as regulators of gene expression," *Curr. Opinion Genetics Dev.*, 7:345–353, 1997.

Sleigh and Lockett, "SV40 Enhancer Activation During Retinoic-Acid-Induced Differentiation of F9 Embryonal Carcinoma Cells," *J EMBO*, 4:3831, 1985.

Sotiropoulos, A., Gineitis, D., Copeland, J. and Treisman, R., Signal-regulated activation of serum response factor is mediated by changes in actin dynamics. Cell, 98, 159–69, 1999.

Spalholz, Yang, and Howley, "Transactivation of a Bovine Papilloma Virus Transcriptional Regulatory Element by the E2 Gene Product," *Cell*, 42:183, 1985.

Spandau and Lee, "Trans-Activation of Viral Enhancers by the Hepatitis B Virus X Protein," *J. Virology*, 62:427, 1988.

Spandidos and Wilkie, "Host-Specificities of Papilloma Virus, Moloney Murine Sarcoma Virus and Simian Virus 40 Enhancer Sequences," *EMBO J*, 2:1193, 1983.

Srivastava, "HAND proteins: molecular mediators of cardiac development and congenital heart disease," *Trends in Cardiovascular Medicine*, 9:11–18, 1999.

Srivastava, Cserjesi, Olson, "A subclass of bHLH proteins required for cardiac morphogenesis, *Sciences*, 270:1995–1999, 1995.

Srivastava, Thomas, Lin, Kirby, Brown, Olson, "Regulation of cardiac mesodermal and neural crest development by the bHLH transcription factor, dHAND," *Nature Genetics*, 16:5477–5490, 1996.

Stephens and Hentschel, "The Bovine Papilloma Virus Genome and its Uses as a Eukaryotic Vector," *Biochem. J*, 248:1, 1987.

Stewart and Young, Solid Phase Peptide Synthesis, 2d. ed., Pierce Chemical Co., 1984.

Stratford-Perricaudet and Perricaudet, Gene transfer into animals: the promise of adenovirus. In: *Human Gene Transfer*, O. Cohen-Haguenauer et al., eds., John Libbey Eurotext, France, pp. 51–61, 1991.

Stratford-Perricaudet et al., "Evaluation of the transfer and expression in mice of an enzyme-encoding gene using a human adenovirus vector", *Hum. Gene. Ther.*, 1:241–256, 1990.

Stuart, Searle, and Palmiter, "Identification of Multiple Metal Regulatory Elements in Mouse Metallothionein-I Promoter by Assaying Synthetic Sequences," *Nature*, 317:828, 1985.

Sullivan and Peterlin, "Transcriptional Enhancers in the HLA-DQ Subregion," *Mol. Cell. Biol.*, 7:3315, 1987.

Swartzendruber and Lehman, "Neoplastic Differentiation: Interaction of Simian Virus 40 and Polyoma Virus with Murine Teratocarcinoma Cells," *J. Cell. Physiology*, 85:179, 1975. Takebe et al., *Mol. Cell. Biol.*, 8:466, 1988.

Tam et al., *J. Am. Chem. Soc.*, 105:6442, 1983.

Tang et al., "A novel Gonadotropin-regulated Testicular RNA Helicase," *J. Biol. Chem.* 274:37932–37940, 1999.

Tavernier, Gheysen, Duerinck, Can Der Heyden, and Fiers, "Deletion Mapping of the Inducible Promoter of Human IFN-beta Gene," *Nature*, 301:634, 1983.

Taylor and Kingston, "EIA Trans-Activation of Human HSP70 Gene Promoter Substitution Mutants is Independent of the Composition of Upstream and TATA Elements," *Mol. Cell. Biol.*, 10:176, 1990.

Taylor and Kingston, "Factor Substitution in a Human HSP70 Gene Promoter: TATA-Dependent and TATA-Independent Interactions," *Mol. Cell. Biol.*, 10:165, 1990a.

Taylor, Solomon, Weiner, Paucha, Bradley, and Kingston, "Stimulation of the Human Heat-Shock Protein 70 Promoter in vitro by Simian Virus 40 Large T Antigen," *J. Biol. Chem.*, 264:15160, 1989.

Temin, Retrovirus vectors for gene transfer: Efficient integration into and expression of exogenous DNA in vertebrate cell genome. In: *Gene Transfer*, Kucherlapati R, ed., New York, Plenum Press, pp. 149–188, 1986.

Thiesen, Bosze, Henry, and Charnay, "A DNA Element Responsible for the Different Tissue Specificities of Friend and Moloney Retroviral Enhancers," *J. Virology*, 62:614, 1988.

Thorburn, J., Xu, S. and Thorburn, A., MAP kinase- and Rho-dependent signals interact to regulate gene expression but not actin morphology in cardiac muscle cells. *EMBO J.*, 16, 1888–900, 1997.

Top et al., "Immunization with live types 7 and 4 adenovirus vaccines. II. Antibody response and protective effect against acute respiratory disease due to adenovirus type 7," *J. Infect. Dis.*, 124:155–160, 1971.

Treisman, "Transient Accumulation of c-fos RNA Following Serum Stimulation Requires a Conserved 5' Element and c-fos 3' Sequences," *Cell*, 42:889, 1986.

Treisman, R., Ternary complex factors: growth factor regulated transcriptional activators. *Curr. Opin. Genet. Dev.*, 4, 96–101, 1994.

Treisman, R., DNA-binding proteins. Inside the MADS box. *Nature*, 376, 468–9, 1995a.

Treisman, R., Journey to the surface of the cell: Fos regulation and the SRE. *EMBO J*, 14, 4905–13, 1995b.

Tronche, Rollier, Herbomel, Bach, Cereghini, Weiss, and Yaniv, "Anatomy of the Rat Albumin Promoter," *Mol. Biol. Med.*, 7:173, 1990.

Tur-Kaspa, Teicher, Levine, Skoultchi and Shafritz, "Use of electroporation to introduce biologically active foreign genes into primary rat hepatocytes," *Mol. Cell Biol.*, 6:716–718, 1986.

Tyndall, La Mantia, Thacker, Favaloro, and Kamen, "A Region of the Polyoma Virus Genome Between the Replication Origin and Late Protein-Coding Sequences is Required in cis for Both Early Gene Expression and Viral DNA Replication," *Nuc. Acids. Res.*, 9:6231, 1981.

Van Aelst, L. and D'Souza-Schorey, C., Rho GTPases and signaling networks. *Genes Dev.*, 11, 2295–322, 1997.

Van Etten, R. A., Jackson, P. K., Baltimore, D., Sanders, M. C., Matsudaira, P. T. and Janmey, P. A. (1994) The COOH terminus of the c-Abl tyrosine kinase contains distinct F- and G-actin binding domains with bundling activity. *J Cell Biol*, 124, 325–40.

Vannice and Levinson, "Properties of the Human Hepatitis B Virus Enhancer: Position Effects and Cell-Type Non-specificity," *J. Virology*, 62:1305, 1988.

Varmus et al., *Cell*, 25:23–36, 1981.

Vasseur, Kress, Montreau, and Blangy, "Isolation and Characterization of Polyoma Virus Mutants Able to Develop in Multipotential Murine Embryonal Carcinoma Cells," *Proc Nat'l Acad. Sci. U.S.A.*, 77:1068, 1980.

Von Harsdorf, R., Hauck, L., Mehrhof, F., Wegenka, U., Cardoso, M. C. & Deitz, R. *Cir. Res.* 85, 128–136, 1999.

Wada, A., Fukuda, M., Mishima, M. and Nishida, E., Nuclear export of actin: a novel mechanism regulating the subcellular localization of a major cytoskeletal protein. *EMBO J.*, 17, 1635–41, 1998.

Wagner, Zenke, Cotten, Beug, Birnstiel, "Transferrin-polycation conjugates as carriers for DNA uptake into cells," *Proc. Nat'l Acad. Sci. USA* 87(9):3410–3414, 1990.

Wang and Calame, "SV40 enhancer-binding factors are required at the establishment but not the maintenance step of enhancer-dependent transcriptional activation," *Cell*, 47:241, 1986.

Wang, D., Chang, P. S., Wang, Z., Sutherland, L., Richardson, J. A., Small, E., Krieg, P. A. and Olson, E. N., Activation of cardiac gene expression by myocardin, a transcriptional cofactor for serum response factor. *Cell*, 105, 851–62, 2001.

Weber, De Villiers, and Schaffner, "An SV40 'Enhancer Trap' Incorporates Exogenous Enhancers or Generates Enhancers From its Own Sequences," *Cell*, 36:983, 1984.

Wei, L., Wang, L., Carson, J. A., Agan, J. E., Imanaka-Yoshida, K. and Schwartz, R. J., Beta1 integrin and organized actin filaments facilitate cardiomyocyte-specific RhoA-dependent activation of the skeletal alpha-actin promoter. *FASEB J*, 15, 785–96, 2001.

Wei, L., Zhou, W., Croissant, J. D., Johansen, F. E., Prywes, R., Balasubramanyam, A. and Schwartz, R. J., RhoA signaling via serum response factor plays an obligatory role in myogenic differentiation. *J. Biol. Chem.*, 273, 30287–94, 1998.

Weinberger, Jat, and Sharp, "Localization of a Repressive Sequence Contributing to B-cell Specificity in the Immunoglobulin Heavy-Chain Enhancer," *Mol. Cell. Biol.*, 8:988, 1984.

Weng, Czaplinski, Peltz, "Genetic and biochemical characterization of mutations in the ATPase and helicase regions of the Upf1 protein," *Molecular Cellular Biol.*, 16:154–160, 1996.

Wilson-Rawls, Molkentin, Black, Olson, "Activated notch inhibits myogenic activity of the MADS-Box taqnscritpion factor myocyte enhancer factor 2C," *Molecular Cellular Biology*, 19:2853–2862, 1999.

Winoto and Baltimore, "αβ-lineage-specific Expression of the α T-Cell Receptor Gene by Nearby Silencers," *Cell*, 59:649, 1989.

WO 84/03564

WO 90/07641, 1990

Wong et al., "Appearance of b-lactamase activity in animal cells upon liposome mediated gene transfer", *Gene*, 10:87–94, 1980.

Wu and Wallace, "The ligation amplification reaction (LAR)—amplification of specific DNA sequences using sequential rounds of template-dependent ligation," *Genomics*, 4:560, 1989.

Wu and Wu, "Evidence for targeted gene delivery to HepG2 hepatoma cells in vitro" *Biochemistry*, 27:887–892, 1988.

Wu and Wu, "Receptor-mediated in vitro gene transfections by a soluble DNA carrier system", *J. Biol. Chem.*, 262: 4429–4432, 1987.

Wu and Wu, *Adv. Drug Delivery Rev.*, 12:159–167, 1993.

Yamamoto, M., Hilgemann, D. H., Feng, S., Bito, H., Ishihara, H., Shibasaki, Y. and Yin, H. L., Phosphatidylinositol 4,5-bisphosphate induces actin stress-fiber formation and inhibits membrane ruffling in CVI cells. *J. Cell. Biol.*, 152, 867–76, 2001.

Yamauchi-Takihara, Sole, Liew, Ing, Liew, "Characterization of human cardiac myosin heavy chain genes," *Proc. Nat'l Acad. Sci. USA*, 86(10):3504–8, 1989.

Yang, Burkholder, Roberts, Martinell and McCabe, "In vivo and in vitro gene transfer to mammalian somatic cells by particle bombardment," *Proc Nat'l Acad Sci. USA*, 87:9568–9572, 1990.

Yutzey, Kline, and Konieczny, "An Internal Regulatory Element Controls Troponin I Gene Expression," *Mol. Cell. Biol.*, 9:1397, 1989.

Zelenin et al., "High-velocity mechanical DNA transfer of the chloramphenicol acetyltransferase gene into rodent liver, kidney and mammary gland cells in organ explants and in vivo", *FEBS Lett.*, 280:94–96, 1991.

Zhang, Wang, Montalvo, "Smubp-2 represses the Epstein-Bar virus lytic switch promoter," *Virology*, 255:160–170, 1999.

Zhao, K., Wang, W., Rando, O. J., Xue, Y., Swiderek, K., Kuo, A. and Crabtree, G. R., Rapid and phosphoinositol-dependent binding of the SWI/SNF-like BAF complex to chromatin after T lymphocyte receptor signaling. *Cell*, 95, 625–36, 1998.

Ziober and Kramer, "Identification and characterization of the cell type-specific and developmentally regulated α7 integrin gene promoter," *J. Bio. Chem.*, 271(37):22915–22, 1996.

What is claimed is:

1. An isolated polynucleotide encoding a striated muscle activated of Rho signaling (STARS) polypeptide, wherein the STARS polypeptide comprises the amino acid sequence of SEQ ID NO: 2.

2. The isolated polynucleotide of claim 1, wherein said polynucleotide comprises the nucleic acid sequence of SEQ ID NO: 1.

3. The polynucleotide of claim 2, wherein said polynucleotide further comprises a promoter operable in eukaryotic cells.

4. The polynucleotide of claim 3, wherein said promoter is selected from the group consisting of hsp68, SV40, Cytomegalovirus (CMV), MKC, GAL4$_{UAS}$, Herpes Simplex Virus (HSV) and β-actin.

5. The polynucleotide of claim 4, wherein said promoter is a tissue specific promoter.

6. An expression construct comprising the polynucleotide of claim 1 operably linked to a regulatory sequence.

7. An the expression construct of claim 6, wherein the polynucleotide, wherein said polynucleotide comprises the nucleic acid sequence of SEQ ID NO: 1.

8. The expression construct of claim 7, wherein said regulatory sequence is a tissue specific promoter.

9. The expression construct of claim 8, wherein said promoter is a muscle specific promoter.

10. The expression construct of claim 9, wherein said muscle specific promoter is selected from the group consisting of myosin light chain-2 promoter, o actin promoter, troponin 1 promoter, $Na^+/Ca^{2+}$exchanger promoter, dystrophin promoter, creatine kinase promoter, α7 integrin promoter, brain natriuretic peptide promoter, αB-crystallin/small heat shock protein promoter, cx myosin heavy chain promoter and atrial natriuretic factor promoter.

11. The expression construct of claim 8, wherein said promoter is an inducible promoter.

12. The expression construct of claim 7, wherein said expression construct is contained in a viral vector.

13. The expression construct of claim 12, wherein said viral vector is selected from the group consisting of a retroviral vector, an adenoviral vector, an adeno-associated viral vector, a vaccinia viral vector, a herpesviral vector, a polyoma viral construct and a Sindbis viral vector.

14. The expression construct of claim 6, wherein said expression construct comprises a polyadenylation signal.

15. The expression construct of claim 6, wherein said expression construct comprises a second polynucleotide encoding a second polypeptide.

16. The expression construct of claim 15, wherein said second said second polynucleotide is under the control of a second regulatory sequence.

17. A method of producing a STARS polypeptide in a cell comprising:
  (a) transforming a cell with an expression cassette comprising the polynucleotide of claim 1 encoding STARS under the control of a promoter active in said cell;
  (b) culturing said cell under the conditions suitable for expression of STARS.

18. The method of claim 17, wherein said cell is a cardiomyocyte or a fibroblast, such as a cardiac fibroblast.

19. The method of claim 17, wherein said cell is located in an animal.

20. The method of claim 17, wherein transforming comprises infection with a viral vector.

21. The method of claim 17, wherein transforming comprises contacting of said cell with a liposome comprising said expression cassette.

22. The method of claim 17, wherein transforming comprises electroporation, calcium phosphate precipitation or protoplast fusion.

23. The method of claim 17, wherein said cell is a prokaryotic cell.

24. The method of claim 17, wherein said cell is a eukaryotic cell.

25. The method of claim 17, further comprising the step of purifying said STARS polypeptide away from other cellular components.

* * * * *

UNITED STATES PATENT AND TRADEMARK OFFICE
CERTIFICATE OF CORRECTION

PATENT NO. : 7,070,957 B2  
APPLICATION NO. : 10/644659  
DATED : July 4, 2006  
INVENTOR(S) : Olson et al.

It is certified that error appears in the above-identified patent and that said Letters Patent is hereby corrected as shown below:

Title page, item (57), lines 7-8, delete "sar comere" and insert --sarcomere-- therefor.

In claim 1, column 91, line 37, delete "activated" and insert/replace --activator-- therefor.

In claim 10, column 92, line 35, delete "cx mysoin" and insert --α myosin-- therefor.

In claim 21, column 93, lines 1-2, delete "compnses" and insert --comprises-- therefor.

In claim 16, column 92, line 53, after "second", delete --said second--therefor.

In claim 10, column 91, line 64, delete "o actin" and insert -- α actin--therefor.

In claim 17, column 92, line 60, after "under", delete --the--therefor.

Cancel claim 7.

In claim 12, column 92, line 39, delete "claim 7" and insert --claim 6-- therefor.

In claim 8, column 91, line 58, delete "claim 7" and insert --claim 6--therefor.

Signed and Sealed this

Twenty-eighth Day of November, 2006

JON W. DUDAS  
*Director of the United States Patent and Trademark Office*